(12) United States Patent
Barrett et al.

(10) Patent No.: US 9,522,165 B2
(45) Date of Patent: *Dec. 20, 2016

(54) FORMULATION AND METHOD FOR THE TREATMENT OF FUNGAL NAIL INFECTIONS

(71) Applicant: Institute of Technology Sligo, Sligo (IE)

(72) Inventors: John Reginald Barrett, Sligo (IE); James Joseph Brennan, Sligo (IE); Thomas Patrick Patton, Sligo (IE)

(73) Assignee: Institute of Technology Sligo, Sligo (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/732,509

(22) Filed: Jan. 2, 2013

(65) Prior Publication Data

US 2014/0154193 A1     Jun. 5, 2014

Related U.S. Application Data

(63) Continuation of application No. 12/570,344, filed on Sep. 30, 2009, now abandoned, which is a continuation of application No. 12/444,231, filed as application No. PCT/IE2007/000094 on Oct. 5, 2007, now abandoned.

(30) Foreign Application Priority Data

Oct. 6, 2006 (GB) .................................. 0619786.7

(51) Int. Cl.
*A61K 33/40* (2006.01)
*A61K 38/44* (2006.01)
*A61K 31/7004* (2006.01)

(52) U.S. Cl.
CPC ........... *A61K 33/40* (2013.01); *A61K 31/7004* (2013.01); *A61K 38/443* (2013.01)

(58) Field of Classification Search
None
See application file for complete search history.

(56) References Cited

U.S. PATENT DOCUMENTS

| | | | |
|---|---|---|---|
| 4,537,764 A | 8/1985 | Pellico et al. | |
| 4,576,817 A | 3/1986 | Montgomery et al. | |
| 4,578,265 A | 3/1986 | Pellico et al. | |
| 4,839,156 A | 6/1989 | Ng et al. | |
| 4,844,898 A * | 7/1989 | Komori et al. | 424/672 |
| 4,950,475 A | 8/1990 | Vishnupad et al. | |
| 5,098,303 A | 3/1992 | Fischer | |
| 5,262,151 A * | 11/1993 | Montgomery | A61Q 11/00 424/50 |
| 5,336,494 A | 8/1994 | Pellico | |
| 5,453,284 A | 9/1995 | Pellico | |
| 5,607,681 A * | 3/1997 | Galley et al. | 424/405 |
| 2003/0228264 A1 | 12/2003 | Perna | |
| 2006/0034816 A1* | 2/2006 | Davis et al. | 424/94.4 |

FOREIGN PATENT DOCUMENTS

| | | | |
|---|---|---|---|
| WO | WO-8802600 A1 | 4/1988 | |
| WO | WO-9638548 A1 | 12/1996 | |
| WO | WO-9965538 A1 | 12/1999 | |
| WO | WO-02080861 A1 | 10/2002 | |
| WO | WO-03090800 A1 | 11/2003 | |
| WO | WO 03092650 A1 * | 11/2003 | ........... A61K 9/0034 |

OTHER PUBLICATIONS

N. F. Brady. P. C. Molan and C. G. Harfoot. The Sensitivity of Dermatophytes to the Antimicrobial Activity of Manuka Honey and Other Honey. Pharmaceutical Sciences 1996.2: 471-473.*
Katrina Brudzynski. Effect of hydrogen peroxide on antibacterial activities of Canadian honeys. Can. J. Microbiol. 52: 1228-1237 (2006).*
David W. Ball. The Chemical Composition of Honey. Journal of Chemical Education. vol. 84 No. 10 Oct. 2007. 1643-1646.*
J. W. White, Jr. and Landis W. Doner. Beekeeping in the United States Agriculture Handbook No. 335 Revised Oct. 1980 pp. 1-12.*
Aditya K. Gupta, Thomas R. Einarson, Richard C. Summerbell, and Neil H. Shear.An Overview of Topical Antifungal Therapy in Dermatomycoses. Drugs May 1998; 55 (5): 645-674.*
Brudzynski, K., Effect of hydrogen peroxide on antibacterial activities of Canadian honeys, Canadian Journal of Microbiology, 52: 1228-1237(2006).
French et al., The antibacterial activity of honey against coagulase-negative staphylococci, Journal of Antimicrobial Chemotherapy, 56: 228-231 (2005).
International Preliminary Report on Patentability for PCT/IE2007/000094, mailed on Jan. 19, 2009.
International Search Report for PCT/IE2007/000094, mailed Mar. 10, 2008.
Molan, The antibacterial activity of honey 1. The nature of the antibacterial activity, Bee World, 1-2: 5-29 (1992).
pH table of bases downloaded Jun. 12, 2012 from http://www.engineeringtoolbox.com/bases-ph-d_402.html.
UKIPO Search Report for priority application GB0619786.7, Feb. 12, 2007.
Wahdan, Causes of the Antimicrobial Activity of Honey, Infection, 26(1): 30/26-35/31 (1998).

(Continued)

*Primary Examiner* — Frederick Krass
*Assistant Examiner* — Michael P Cohen
(74) *Attorney, Agent, or Firm* — VLP Law Group LLP; Richard G. A. Bone

(57) ABSTRACT

The present invention relates to a formulation and method for the treatment of fungal nail infections, such as those caused by *Trichophyton rubrum* and/or *Aspergillus niger*. The formulation of the invention comprises glucose oxidase, D-glucose and hydrogen peroxide in an aqueous solution. Advantageously, the formulation of the invention provides a two-stage hydrogen peroxide release for the treatment of the fungal nail infections.

16 Claims, 58 Drawing Sheets

(56) References Cited

OTHER PUBLICATIONS

White et al., The identification of inhibine, the antibacterial factor in honey, as hydrogen peroxide and its origin in a honey glucose-oxidase system, Biochim Biophys Acta, 73: 57-70 (1963).

White, J.W. and Doner, L.W., Honey Composition and Properties, Beekeeping in the United States: Agriculture Handbook, 335: 82-91 (Oct. 1980).

Bang, L. M., et al., "The Effect of Dilution on the Rate of Hydrogen Peroxide Production in Honey and Its Implications for Wound Healing", The Journal of Alternative and Complementary Medicine, 9:267-273 (2003).

* cited by examiner

FORMULATION AND METHOD FOR THE TREATMENT OF FUNGAL NAIL INFECTIONS

RELATED APPLICATIONS

This application is a continuation of U.S. patent application Ser. No. 12/570,344, filed Sep. 30, 2009, which is a continuation-in part of U.S. patent application Ser. No. 12/444,231, filed Jan. 19, 2010, which claims the benefit under 35 U.S.C. §317 of International Application No. PCT/IE2007/000094 (PCT Publication No. WO 2008/041218), filed Oct. 5, 2007, which claims priority to United Kingdom Patent Application No. 0619786.7, filed Oct. 6, 2006, the entire contents of each of which is hereby incorporated herein by reference.

FIELD OF THE INVENTION

The present invention relates to a formulation and method for the treatment of fungal nail infections. Ideally, the fungal nail infections are caused by *Trichophyton rubrum* and/or *Aspergillus niger*.

BACKGROUND TO THE INVENTION

Well-known antimicrobial compositions include conventional treatments such as antiseptics and antibiotics. Other treatments include silver-containing gels, compounds containing heavy metals and solutions of hydrogen peroxide and natural and synthetic pharmaceutically active substances. However, treatments such as antibiotics have disadvantages because of the emergence of antibiotic resistance. Furthermore, high levels of hydrogen peroxide have a toxic and irritant effect. In addition, hydrogen peroxide in solution is typically unstable and it is difficult to provide a sustained delivery system for this material. Additionally, there are a number of naturally occurring antimicrobial systems known which rely on the ability of certain oxidising agents to disrupt metabolic processes of bacteria, fungi and viruses. Thus, for a wide variety of different reasons, conventional antimicrobial treatments have many drawbacks.

Onychomycosis is a fungal nail infection that accounts for approximately 50% of all nail disorders and affects toenails substantially more than fingernails. The prevalence of onychomycosis has been estimated at around 3% in Western countries and has continued to increase in recent decades.

Onychomycosis may be caused by several causal agents including dermatophytes, yeasts or moulds. It is accepted that dermatophytes are by far the predominant pathogens and probably account for more than 85% of all cases of fungal nail infections. Of the dermatophytes the most common cause of onychomycosis is *Trichophyton rubrum*. *Aspergillus niger* has also been found to be another causal agent of onychomycosis. Causative fungi include *Scopulariopsis brevicaulis* and *Scytaldium dimidiatum*.

Distal and lateral subungual onychomycosis (DLSO) is the commonest type of onychomycosis. Infection is initially a disease of the hyponychium, resulting in hyperkeratosis of the distal nail bed. It generally begins at the lateral edge of the nail rather than the central portion and spreads progressively proximally down the nail bed producing hyperkeratosis and thus onycholysis. Ultimately the underside of the nail is involved which results in thickening of the nail. The nail may become friable and crumbles away. Sometimes the fungus proliferates in the space between the nail plate and nail bed (known as a dermatophytoma) and is often the cause of treatment failure.

It is important to treat onychomycosis, as it is an infection and does not resolve spontaneously. The infection may worsen, spread to other uninfected locations (other nails or to the surrounding skin) or infect other people. Infections of the fingernails may be cosmetically unacceptable. Infections of the toenail can greatly affect the quality of life of patients and cause pain and morbidity.

Current treatments for onychomycosis include topical or oral treatments. There are four main oral therapies available for the treatment of onychomycosis. These are Griseofulvin (Grisovin®, Glaxo Wellcome) Ketoconazole (Nizoral®, Janssen-Cilag), Itraconazole (Sporanox®, Janssen-Cilag) and Terbinafine (Lamisil®, Novartis). Griseofulvin has been available since the 1950's and due to its fungistatic activity against dermatophytes requires long treatment periods, approximately 9 to 12 months for toenail infections, with low cure rates and high relapse rates. Ketoconazole was the first imidazole introduced for the treatment of onychomycosis in the 1980's. However, due to hepatotoxicity its use is now restricted to fingernail infections that have failed to respond to other therapies. The newer antifungals, Itraconazole and Terbinafine, are highly effective in the treatment of onychomycosis with mycological cure rates of 70-80% and treatment periods of 12 to 16 weeks. Topical therapies include Amorolfine (Loceryl®, Galderma) and Ciclopirox (Penlac®, Dermik). Probably as a result of the poor drug penetration from these products through the nail, treatment times are long, approximately 12 months for toenail infections, and cure rates are low, Thus, alternative drugs and formulations to improve delivery are being sought.

Drug delivery to the nail (ungual delivery) is complicated by the physical structure of the nail. The nail apparatus is composed of the nail folds, nail matrix, nail bed and the nail plate. The nail plate, produced mainly by the matrix, emerges via the proximal nail fold and is held in place by the lateral nail folds. It overlays the nail bed and detaches from the latter at the hyponychium.

The nail plate is a thin, hard, yet slightly elastic, translucent convex structure and is made up of approximately 25 layers of dead keratinised cells which are tightly bound to one another by numerous intercellular links. Chemically, the nail plate consists mainly of the fibrous proteins, keratin, 80% of which is the 'hard' hair-type keratin, the remainder comprising the 'soft' skin-type keratin. The keratin fibres are oriented into three layers, which are associated with the dorsal, intermediate and ventral nail layers. The hair like keratin filaments are only present in the intermediate nail layer and are oriented perpendicular to the growth axis. The nail plate is formed by the nail matrix, which is a highly proliferative epidermal tissue. Cell division of the nail matrix results in the continuous formation of the plate, which grows throughout life. The growth rate is highly variable among individuals; with average values of 3 µm per month for finger nails and 1 µm per month for toe nails. The growth is also highly affected by age, gender, climate, trauma, disease and drug intake. As well as growing in length, nail plates also grow thicker as they progress from the lunula to the free margin.

The table below shows a comparison of the chemical composition of the nail plate and the Stratum corneum (outer layer of the epidermis).

| Characteristic | Nail | Stratum corneum |
| --- | --- | --- |
| Thickness | 50-1000 m | 10-40 m |
| Di-sulphide linkage | 10.60% | 1.20% |
| Lipid content | 0.1-1% | 10-20% |
| Water content | 9-35% | 25% |
| Maximum swelling | 25% | 200-300% |
| Water loss | 1.94 mg/cm2/h | 0.56 mg/cm2/h |

In comparison to the thin Stratum corneum, the much thicker nail plate means a much longer diffusional pathway for drug delivery. In addition, in contrast with the elastic and pliable Stratum corneum, the nail plate is dense and hard. When the thickness difference is taken into consideration, the water permeation rate of the nail is approximately 10 times higher than that of the Stratum corneum. As such it would be expected that the permeation characteristics of the nail are very different from the Stratum corneum, the main differences being detailed below:

- The nail does not act like a lipoidal barrier but like a hydrophilic gel membrane;
- Disulphide bonds are responsible for toughness of nail and its barrier properties;
- Aqueous pathways play a more dominant role in drug permeation across the nail; and
- Penetration enhancers (e.g. keratolytic and mucolytic agents) are generally required and are different for the nail.

These differences between the nail and Stratum corneum, both physical and chemical, are probably the reasons for the lack of efficacy of topical nail antifungal formulations presently on the market. Thus, when designing topical formulations for perungual drug absorption, it is essential to consider the physicochemical properties of the drug molecule (e.g. size, shape, charge log P etc), the formulation characteristics (e.g. vehicle, drug concentration), possible penetration enhancers, as well as any possible interactions between the drug and keratin.

To date, conventional topical treatments for fungal nail infections all have significant limitations and have largely been unsuccessful.

In addition, designing alternative treatments has been problematic due to the chemical composition of the nail.

Thus, the present invention is directed to providing an alternative treatment for fungal nail infections.

STATEMENT OF THE INVENTION

According to a first aspect of the invention, there is provided a storage-stable antimicrobial formulation for the treatment of fungal nail infections, comprising;
- glucose oxidase at an activity of at least 10 U per 100 g of the formulation;
- D-glucose from 20 to 85% by weight based on the weight of the total formulation;
- additional sugars selected from one or more of sucrose, fructose and/or maltose from 5 to 70% by weight based on the weight of the total formulation;
- water from 10 to 20% by weight based on the weight of the total formulation;
- with a pH from approximately 4 to 8
- wherein the formulation provides a two-stage hydrogen peroxide release in which
  - (a) storage-stable endogenously produced hydrogen peroxide is bioavailable within the formulation at a level of at least 10 mg per liter for immediate release; and
  - (b) the sustained release of further hydrogen peroxide for at least a twenty-four hour period occurs upon rehydration of the formulation.

The formulation is used in the treatment of onchomycosis.

Ideally, the formulation has antifungal and sporocidal effects which penetrate into and through the nail plate.

According to a second aspect of the invention, there is provided a combined therapy for the treatment of fungal nail infections comprising (i) the formulation of the invention and (ii) an antimicrobial agent for the treatment of fungal nail infections.

According to a third aspect of the invention, there is provided a method for the treatment of fungal nail infections comprising the topical administration to an affected nail, or to an affected nail and surrounding skin, of an effective amount of the formulation of the invention, such that the formulation ideally penetrates into and through the nail plate.

DETAILED DESCRIPTION OF THE INVENTION

In the specification, it will be understood that the term "antimicrobial" or "antibacterial" are used interchangeably herein and cover biocidal or biostatic activity against various types of micro-organisms including but not limited to bacteria, fungi, viruses, yeasts, parasitic or pathogenic microorgansims and/or moulds.

In the specification, it will also be understood that the term "an antimicrobial agent" encompasses all chemotherapeutic antimicrobial drugs, preferably antibiotics or antifungal, antiviral and antiparasitic agents.

In the specification the term "by weight", "percentage by weight" or "w/w %" refers to the weight of the final composition or system. These w/w values are interchangeable with w/v.

According to the main aspect of the present invention, there is provided a storage-stable antimicrobial formulation for the treatment of fungal nail infections comprising;
- glucose oxidase at an activity of at least 10 U per 100 g of the formulation;
- D-glucose from 20 to 85% by weight based on the weight of the total formulation;
- additional sugars selected from one or more of sucrose, fructose and/or maltose from 5 to 70% by weight based on the weight of the total formulation;
- water from 10 to 20% by weight based on the weight of the total formulation;
- with a pH from approximately 4 to 8
- wherein the formulation provides a two-stage hydrogen peroxide release in which
  - (a) storage-stable endogenously produced hydrogen peroxide is bioavailable within the formulation at a level of at least 10 mg per liter for immediate release; and
  - (b) the sustained release of further hydrogen peroxide for at least a twenty-four hour period occurs upon rehydration of the formulation.

Ideally, the formulation has antifungal and sporocidal effects which penetrate into and through the nail plate.

It is well known that the nail/nail plate is an excellent barrier against the ingress of foreign material. Accordingly, the nail also prevents effective topical treatment of nail infections which has been a significant problem in the treatment of fungal nail infections.

However, we have surprisingly found the formulation of the invention, which has both antifungal and sporocidal effects, ensures the permeation of the antifungal and sporocidal activity into and through the nail plate to act as an effective fungal nail infection treatment. Accordingly, the formulation of the invention enables the antimicrobial effect to permeate into and through the nail plate to the nail bed. In this way, the antimicrobial effect can permeate into and through a nail plate of from approximately 5 µm thickness to a full thickness nail plate.

Furthermore, the formulation has antimicrobial effect beyond that of an antifungal treatment alone. This functionality as both an antimicrobial and antifungal agent provides for a more effective treatment.

Advantageously, the formulation is a storage stable, single component system which is ready for immediate use and is fast-acting. Thus, the formulation can be easily produced and delivered to an infected nail. The antimicrobial, antifungal and sporocidal effect of the formulation is mediated by the two-stage hydrogen peroxide release. Advantageously, the formulation provides this two-stage hydrogen peroxide release in a regulated, defined and reproducible manner. Firstly, the formulation provides storage-stable hydrogen peroxide for immediate release. This endogenous reservoir provides an immediately available hydrogen peroxide and an immediate antimicrobial effect. This is one of the significant advantages of the present invention. Secondly, after re-hydration, the formulation provides for a second tier of hydrogen peroxide activity involving the sustained release of hydrogen peroxide for at least a twenty-four or forty-eight hour period.

Furthermore, although the use of concentrated hydrogen peroxide for the treatment of fungal nail infections has been described anecdotally in the literature, to date hydrogen peroxide is not conventionally used in the treatment of infections such as fungal nail infections. In such instances a high concentration of hydrogen peroxide is required due the instability of aqueous hydrogen peroxide and the absence of an effective delivery system to the nail, Hydrogen peroxide is undesirable as at the high concentrations required for efficacy, it is both toxic and acts as a skin irritant. These are both significant and undesirable side-effects. Furthermore, hydrogen peroxide is chemically unstable and decays rapidly leading to a rapid decline in diffusion potential. The formulation of the present invention overcomes the inherent limitations associated with the conventional delivery of hydrogen peroxide in the following manner:

Firstly, the formulation of the invention overcomes the problems associated with the delivery of larger molecules, such as conventional antifungal agents, into and through the nail plate. Due to their size, it is difficult for such larger molecules to diffuse through the small pores between the keratin fibres in the nail plate. Advantageously, the formulation of the invention provides a two stage release of hydrogen peroxide which is able to readily penetrate the small pores between the keratin fibres in the nail plate. The sustained/two-stage delivery aspect of the formulation allows hydrogen peroxide to be used as an effective antifungal agent for the first time in the treatment of fungal nail infections. This sustained delivery mechanism provides a constant level of hydrogen peroxide at the source of application by providing a constant thermodynamic potential difference between the formulation and nail plate, thereby enhancing and facilitating the diffusion of hydrogen peroxide through the nail plate. The formulation is non-toxic and non-irritant, in direct contrast with the application of hydrogen peroxide per se.

Additionally and advantageously, the formulation of the invention is hydroscopic. The hydroscopic nature of the formulation ensures that the nail plate is hydrated at all times. This ensures that the keratin bundles present in the nail plate swell and this allows for easier penetration of the formulation and hydrogen peroxide into and through the nail plate. Due to the hydroscopic nature of the formulation, the application of an additional external source of water may not be necessary for the second tier of hydrogen peroxide release. This is a significant advantage of the present invention.

Many other treatments require penetration enhancers, however, for the above reasons the formulation of the invention does not require the use of a penetration enhancer.

Thus, the sustained release combined with the hydroscopic nature of the formulation, ensures that the formulation provides a very efficient transport mechanism for hydrogen peroxide from the formulation to the site of infection in the nail bed and/or in the nail plate.

There are other advantages associated with the formulation.

For example, catalase is secreted by fungi as a defence mechanism. Thus, when hydrogen peroxide is applied to a fungal nail infection, catalase is secreted which results in the breakdown of hydrogen peroxide, reducing the efficacy. We have found that by ensuring the pH of the formulation is low, ideally from 4 to 8, ideally 4 to 6, this provides a less than optimum environment for catalase activity and overcomes one of the infecting fungi defence mechanisms. Thus, the low pH of the formulation prevents the degradation of hydrogen peroxide applied to the site of fungal nail infection.

Accordingly, we have found that the formulation of the invention is a very effective fungal nail infection treatment. Ideally, the fungal nail infections is caused by *T. rubrum* and/or *A. niger*.

According to a preferred embodiment of this aspect of the invention, the storage-stable endogenously produced hydrogen peroxide is bioavailable within the system at a level of at least 10, preferably 75 mg hydrogen peroxide per liter or parts per million for immediate release. However, it will be understood that the level of endogenously produced hydrogen peroxide which is immediately bioavailable within the system will depend on the amount of oxidoreductase enzyme present in the formulation. Hence, the level could be much greater than 10 or 75 mg of hydrogen peroxide per liter of the formulation if the level of oxidoreductase enzyme used is high. Thus, if the concentration of oxidoreductase enzyme and/or substrate for the oxidoreductase enzyme is increased, then the pool of endogenous hydrogen peroxide increases. For example, we have found that approximately 175 U of oxidoreductase enzyme per 100 g formulation generates an endogenous pool of approximately 10 mg hydrogen peroxide per liter. Furthermore, approximately 1400 U of oxidoreductase enzyme per 100 g formulation generates an endogenous pool of approximately 25 mg hydrogen peroxide per liter This initial endogenous reservoir of hydrogen peroxide present is storage-stable and remains until the second tier of hydrogen peroxide is released. This storage-stability aspect is another advantage of the present invention. In the context of this application, storage-stable means that the endogenously produced hydrogen peroxide is maintained for a period of from approximately 3 months up to approximately 36 months. Furthermore, the formulation does not degrade, separate or lose activity during this time period. The expected shelf life under normal conditions is approximately 36 months or more. In addition, when subject to sterilisation, for example by irradiation, the formulation does not deteriorate in quality or activity.

Upon use or application of the formulation of the present invention, a second-tier of hydrogen peroxide is released where the level of sustained release hydrogen peroxide produced upon rehydration of the formulation is at least 10 mg, preferably 20 mg of hydrogen peroxide per liter or parts per million. Again, the level of sustained release hydrogen peroxide generated will depend on the amount of oxidoreductase enzyme and/or substrate for the oxidoreductase enzyme present in the system. Furthermore, we have advantageously found that the sustained release of further hydrogen peroxide occurs for at least a twenty-eight, if not a forty-eight hour period.

The formulation of the invention also has an immunostimulatory effect which is mediated by interleukin-1. IL-1 is a cytokine which is also secreted by macrophages, monocytes and dendritic cells. It is an important part of the inflammatory response of the body against infection. It increases the expression of adhesion factors on endothelial cells to enable transmigration of leukocytes to sites of infection. It also acts on the thermoregulation centre of the brain leading to an increased body temperature in the form of a fever. It is therefore called an endogenous pyrogen. The increased body temperature helps the body's immune system to fight infection. This is the initial phase of an inflammatory immune response which augments the antimicrobial activity of the system. The inflammatory response plays a central role in wound healing through its defence against possible infection and by participating in cell and tissue repair and re-growth. Thus, the antimicrobial effect of the formulation is aided and complemented by the immunostimulatory effect which aids the regrowth and repair of damaged tissues and/or cells.

The formulation advantageously utilises these new and unexpected findings and provides a system which gives a regulated, defined and reproducible level of antimicrobial activity against fungal nail infections.

An additional benefit from the formulation is the ability to alter the quantity of active and excipient ingredients thereby permitting the production of a range of formulations of various strengths and properties. This includes the ability to optimise the pH for the required target site. Thus, the formulation of the invention is readily reproducible. This allows a high level of quality control with respect to safety and efficacy, batch consistency, potency determination, and a greater control of impurities, in keeping with current Good Manufacturing Practice (cGMP) requirements.

It is a still further advantage of the formulation that it will not cause any allergic reactions, due to its defined composition. It is non-toxic and non-irritant. Advantageously, this allows for precise labelling instructions as required by the US/EU legislation for pharmacologically active products.

Ideally, water is present at a level from approximately 10% to approximately 20% by weight based on the weight of the total formulation. More preferably, water may be present a level from approximately 10% to approximately 15% by weight based on the weight of the total formulation. The amount of water present initially is an important aspect of the invention. The addition of excess water can lead to instability, as excess water may give rise to hydrolysis of the glucose oxidase, so it is important that water is only initially present within defined parameters. In addition, the formulation requires sufficient water to permit generation of $H_2O_2$, ease of application and to prevent precipitation of sugars during storage.

Ideally, the oxidoreductase enzyme is present at an activity of at least 10 U per 100 g of the system. Generally speaking, one unit (U) is that amount of enzyme causing the oxidation of one micromole of glucose per minute at 25° C. and pH 7.0. It will be understood that there must be sufficient oxidoreductase enzyme present to catalyze the substrate and form hydrogen peroxide as needed. Preferably, the oxidoreductase enzyme is present at an activity of at least 100 U, 1400 U, 5600 U or even 260,000 U per 100 g of the system.

Ideally, the formulation has a pH from approximately 4 to 8, preferably from 5 to 7, more preferably approximately 5.5. The pH is important because it plays a critical role in many therapeutic aspects of the present invention, for example wound healing and also ensures that the glucose oxidase has the correct conditions needed for optimal activity. Thus, the ability to manipulate pH is highly desirable and a significant advantage of the present invention. Advantageously, the pH may be set at a pH as required for the particular application. Buffering agents may be used to manipulate the pH. Optionally, the formulation further comprises a buffering agent, preferably carbonic acid-bicarbonate and/or phosphoric acid/disodium hydrogen phosphate. Preferably, the buffering agent is pre-dissolved in and replaces part of the water of the formulation. Different concentrations of buffering agent can be used depending on the desired pH.

The formulation comprises additional sugars. By the term "additional sugars" we mean sugars other than D-glucose. The additional sugars are chosen from sucrose, fructose and/or maltose. Ideally, the additional sugars are sucrose, fructose and maltose. The additional sugars may be present from 5% to 80%, preferably 10 to 70%, by weight based on the weight of the total formulation.

According to a preferred embodiment of the present invention,

D-glucose is present from 20 to 85 w/w %, preferably from 10 to 85% w/w, more preferably from 26 to 43 w/w %, even more preferably from 33 to 43 w/w %;

the additional sugarssucrose, fructose and/or maltose are present from 5 to 70 w/w %, preferably from 10 to 70 w/w %, and water is present from 10 to 20 w/w %, more preferably from 10 to 15% w/w %.

The additional sugars may be present in the follow ranges (based on the weight of the formulation):

| Additional Sugars | Range (w/w %) |
| --- | --- |
| Fructose | 8 to 50, preferably from 30 to 40 |
| Maltose | 4 to 15, preferably from 5 to 15 |
| Sucrose | 0.5 to 3, preferably from 0.5 to 2.5 |

The glucose oxidase is present at an activity of at least 10 U per 100 g of the formulation. The amount of glucose oxidase to be used will depend on the activity of the enzyme used and the amount of substrate, i.e. sugars, present in the formulation.

Ideally, the ratio of fructose:glucose:maltose:sucrose is approximately 3.7:4:1.05:0.16.

According to another embodiment of this aspect of the invention, the formulation may further comprise at least one viscosity modifying ingredient. Ideally, the viscosity modifying ingredient is selected from the following:

Methyl cellulose

Carboxymethyl cellulose

Hydroxypropyl methyl cellulose
Hydroxyethyl cellulose
Hydroxypropyl cellulose
Carbopol
Polyvinyl alcohol
Polyvinyl pyrrolidone
Hydrogenated vegetable oils
Xanthan Gum and other natural gums
Polytheylene Glycols (low and high molecular weight)
Paraffin (liquid, semisolid and solid) and/or
Glycerol.

Other conventional viscosity modifying ingredients may also be used.

Optionally, the additional sugars as defined before may act as the viscosity modifying ingredient. For example, a change in ratios of the additional sugars may result is a corresponding increase or decrease in the viscosity of the system. Thus, a separate viscosity modifying ingredient may not necessarily be required.

It will be understood that the additional sugars and/or the viscosity modifying ingredients are added to provide the necessary physical properties needed for the specific application of the formulation. For example, when the formulation is used topically, it must have sufficient viscosity to adhere to the applied surface. In this situation it may be desirable to use an additional viscosity modifying ingredient and/or modify the ratios of additional sugars present.

According to a preferred embodiment of this aspect of the present invention, there is provided a formulation comprising glucose oxidase, D-glucose and hydrogen peroxide in an aqueous solution; wherein D-glucose is present up to 85% by weight and water is present up to 20% by weight based on the weight of the total formulation; the formulation has a pH from approximately 4 to 8; and the formulation provides a two-stage hydrogen peroxide release in which (a) storage-stable endogenously produced hydrogen peroxide is bioavailable within the formulation at a level of at least 10 mg per liter for immediate release; and (b) the sustained release of further hydrogen peroxide for at least a twenty-four hour period occurs upon rehydration of the formulation.

According to another embodiment of this aspect of the invention, there is provided a formulation comprising a saturated solution of sugars, including glucose, and water at a ratio of from approximately 10:1 to approximately 5:1, wherein water is present up to 20% by weight based on the total formulation; and the weight of glucose oxidase can vary depending on the activity, for example from approximately 0.01% to 1%; and endogenously derived hydrogen peroxide for immediate release; wherein the formulation has a pH of from approximately 4 to 8, the bioavailability of hydrogen peroxide is maintained in the formulation and sustained release of further hydrogen peroxide occurs upon rehydration.

The formulation may be in many different physical forms, including but not limited to liquid preparations, solid or semi-solid preparations. In order to prepare solid or semi-solid formulations, the ingredients of the formulation should be manipulated to lower the water content and increase the content of the other components.

The formulation may be in the form of a liquid preparation. Liquid preparations include but are not limited to a syrup, paste, spray, drop, ointments, creams, lotions, oils, liniments and/or gels. A typical gel includes an alcoholic gel such as isopropanol, ethanol, or propanol and/or a hydrogel.

Alternatively, the formulation may be in the form of a solid or semi-solid preparation. Solid or semi-solid preparations include but are not limited to capsules, pellets, gel caps, hydrogels, pillules and/or globules.

According to a preferred embodiment of this aspect of the invention, there is provided a pharmaceutical composition comprising the formulation together with at least one pharmaceutically acceptable excipient or adjuvant.

According to another embodiment, there is provided a dressing comprising the formulation or pharmaceutical composition of the invention. Such dressings include gauzes, bandages, films, gels, foams—Lyofoam®, hydrocolloids—Granuflex®, alginates—Kaltostat® (Comvita), hydrogels—Intrasite Gel® and polysaccharide pastes, granules and beads, Chitosan® and Nano-Fibre® containing dressings.

According to a particular embodiment, the formulation may be provided with a wound-dressing matrix. Ideally, the ratio of the system to wound-dressing matrix may be approximately 1:1, although other ratios are contemplated. The wound-dressing matrix may be a collagen or collagen-GAG (glycosaminoglycan) matrix.

It will be understood that the formulation or pharmaceutical composition of the invention, may be present in many different administration forms. These forms include but are not limited to forms adapted for topical, enteral or parenteral administration.

Forms suitable for topical administration include a topical ointment, cream, lotion, oil, liniment, liquid and/or gel. For example, the system of the present invention may be applied epicutaneously. Further compositions may be adapted as tissues, bandages or dressings.

Another form suitable for topical administration includes the formulation or pharmaceutical composition of the invention wherein the formulation or composition is in a form adapted for delivery via a dissolvable film strip or strips. In this situation the formulation is soluble upon application.

Parenteral administration forms include, but are not limited to forms suitable for injection.

According to a further general aspect of the invention, there is provided a method for the treatment of fungal nail infections comprising the topical administration to an affected nail, or to an affected nail and surrounding skin of an effective amount of the formulation of the invention, such that the formulation penetrates into and through the nail plate. Furthermore, the formulation of the invention may also be used in the prophylactic prevention of such microbial, i.e. fungal nail, infections.

According to a further general aspect of the invention, there is provided a combined therapy for the treatment of fungal nail infections comprising (i) the formulation of the invention and (ii) an antimicrobial agent for the treatment of fungal nail infections.

The antimicrobial agent may be selected from one or more of Griseofulvin (Grisovin®), Ketoconazole (Nizoral®), Itraconazole (Sporanox®), Clotrimazole, Terbinafine (Lamisil®), Amorolfine (Loceryl®) and/or Ciclopirox (Penlac®).

In this specification the term "combination therapy" is used broadly. The combination therapy may be produced in one pharmaceutical form comprising both active ingredients or in two separate forms including tablets, capsules, powders, mixtures or solutions. Hence, the term "combination therapy" covers both the simultaneous, sequential and/or separate administration of the hydrogen peroxide source and the antimicrobial agent or agents. Accordingly, the active ingredients of the combination therapy may be administered at substantially the same time or at different times.

Thus, the term "combination therapy" covers the combination of the antimicrobial agent or agents and the formulation of the invention as a single entity, i.e. a combined preparation. In this way, the formulation of the invention may be combined, integrated or sequestered with the antimicrobial agent or agents either during or after manufacture.

Alternatively, the antimicrobial agent or agents may be packaged separately to the formulation of the invention for co-administration. In this situation a set of instructions for co-administration can also be provided. For example, the invention also provides a means by which the systemic use of antimicrobial agents for treating topical infection may be augmented by the simultaneous topical treatment of the infection with the invention.

The invention will now be illustrated by the following non-limiting examples with reference to the following figures, in which:

FIG. 1a shows a microbial inhibition profile of Manuka honey on Staphylococcus aureus. Manuka honey demonstrates a two tier inhibition profile. The first tier of microbial inhibition activity occurs between dilutions 50% to approximately 6.25% and the second tier of microbial inhibition activity occurs at dilutions 3.125% to approximately 0.195%;

FIG. 1b shows a microbial inhibition profile of pH adjusted Manuka honey on Staphylococcus aureus. Adjusting the pH of Manuka honey from its natural pH of approximately 4.0 to a pH of 6.8 does not affect the microbial inhibition profile;

FIG. 1c shows a microbial inhibition profile of pH adjusted Manuka honey to which an excess of catalase has been added on Staphylococcus aureus. Manuka honey pH adjusted to near a neutral pH followed by the addition of catalase in excess alters the microbial inhibition profile of the honey. The first tier of microbial inhibition is only slighted affected but the second tier is significantly affected indicating that the antibacterial effect in the second tier is primarily the result of hydrogen peroxide liberation;

FIG. 2 shows a microbial inhibition profile of Manuka honey and a prototype formulation on Staphylococcus aureus. The prototype formulation demonstrates greater activity compared to that of the Manuka honey;

FIG. 3a shows the results of a microbial inhibition assay using gel based prototype formulations on Staphylococcus aureus, E. coli and Candida Albicans. Both cellulose based gels demonstrate a decrease in stability and neither cellulose based gel formulation is as active as the prototype formulation as evidenced by the smaller zones of inhibition in diffusion assays (compare FIG. 3a (gels) with FIG. 3b (prototype formulation));

FIG. 3b shows the results of a microbial inhibition assay of the prototype formulations on Staphylococcus aureus. Large zones of inhibition are evident indicating activity;

FIG. 4a shows the results of microbial inhibition assay of Glucose//glucose oxidase only formulations on different bacteria. Microbial inhibition assays of 4 replicate of 75% D-glucose with 0.5% GOX 5600 U/g in wells and their antimicrobial activity against a number of different bacteria. These formulations demonstrate a limited degree of antibacterial activity. This activity is below that observed with the prototype antimicrobial formulation described in Example 2 as evidenced by the smaller zones of inhibition in Well/Disc diffusion assays (compare FIG. 4a (gels) with FIG. 4b (prototype));

FIG. 4b shows the results of microbial inhibition assay of the prototype formulation against a number of different bacteria;

FIG. 5a shows the activity of A³IS containing different GOX (5600 U/g) enzyme concentrations against S. aureus. Varying the glucose oxidase content in A³IS and its affect on the inhibition profile was measured. The antibacterial activity of A³IS increases proportionally to the concentration of glucose oxidase. A substantial antibacterial effect is attained at an enzyme concentration of 0.05%;

FIG. 5b shows $H_2O_2$ generation over time by A³IS containing 0.5% sigma Aldrich GOX enzyme 5600 U/g diluted 50% (C1), 25% (C2), 12.5% (C3) or 6.25% in de-ionised water (DI). A³IS generates significantly increased levels of hydrogen peroxide compared to Manuka honey diluted at 50% in DI water;

FIG. 5c shows $H_2O_2$ generation over time by A³IS. Production of $H_2O_2$ by A³IS with 0.5% sigma Aldrich GOX enzyme 5600 U/g and diluted 25% in DI water) is maintained for a period of at least 48 h;

FIG. 5d shows that A³IS—antimicrobial activity increases with increased glucose oxidase concentration. Potency/efficacy is dependant on the concentration of glucose oxidase in A³IS formulations. Results show an increase in efficacy with increasing glucose oxidase concentration when tested on Staphylococcus aureus, Pseudomonas aeruginosa and Escherichia coli;

FIG. 6 shows the stability results and retention of $H_2O_2$ reservoir by A³IS over a ten month period. The available $H_2O_2$ reservoir produced by A³IS is storage stable. The level of available $H_2O_2$ present was initially determined immediately after being placed into tubes and again after a period of 7 and 10 months had elapsed. There is no evidence of a loss of available $H_2O_2$ within the A³IS formulation, thus, indicating stability. Similar results have been obtained with several other batches.

FIG. 7a shows antimicrobial activity in an A³IS formulation on Staphylococcus aureus over 3 months. The antimicrobial activity in an A³IS formulation on Staphylococcus aureus demonstrates a consistent level of antimicrobial activity over time as determined by zones of inhibition measured at each sampling time point and the results graphed using 95% confidence limits during a period of 3 months;

FIG. 7b shows the antimicrobial activity in an A³IS formulation on Staphylococcus aureus over 14 months. The antimicrobial activity in an A³IS formulation on Staphylococcus aureus demonstrates a consistent level of antimicrobial activity over time as determined by zones of inhibition measured at each sampling time point and the results graphed using 95% confidence limits during a period of 14 months;

FIG. 8a shows the A³IS antimicrobial activity against Staphylococcus aureus, NCCLS kill curve method. Antimicrobial activity of A³IS against Staphylococcus aureus, as determined by an NCCLS kill curve method. A³IS has increased efficacy compared with Manuka honey and comparable efficacy to silver dressing;

FIG. 8b shows the A³IS antimicrobial activity against Staphylococcus aureus, a Medical Device Manufacturer's Specific Method. Antimicrobial activity of A³IS against Staphylococcus aureus, as determined by a Medical device manufacturer's specific protocol. A³IS has increased efficacy compared with Manuka honey and comparable efficacy to silver dressing;

FIG. 8c shows the A³IS—antimicrobial activity against beta haemolytic Streptococci Group A. Results of an inhibition assay (3 day repeats) for A³IS, Medihoney® and a 10% phenol gel tested against 5 clinical isolates of the Beta haemolytic Streptococci Group A. A³IS is at normal pH 5.5 (test material A) and pH 7 (test material B), a negative control of A³IS containing no GOX is included. Formulation A³IS demonstrates comparable in vitro efficacy to a 10% phenol gel and is superior to Medihoney®;

FIG. 8d shows the A³IS—antimicrobial activity against *Campylobacter*. Results of an inhibition assay (3 day repeats) for A³IS, Manuka honey and a 10% phenol gel when tested against 5 clinical isolates of *Campylobacter* spp. Formulation A³IS is at normal pH 5.5 (test material A) and pH 7 (test material B), a negative control A³IS containing no GOX is included. Results indicate significant anti-*Campylobacter* in-vitro efficacy and the superiority of A³IS over Manuka honey;

FIG. 9a shows the A³IS—antimicrobial activity against *P. acnes*. A³IS activity against *P. acnes* under varying incubation conditions: light and dark aerobic, light and dark anaerobic. A³IS demonstrates a high level of activity against *P. acnes*, indicating the materials potential for topical acne application;

FIG. 9b shows the A³IS—antimicrobial activity against *P. acnes*. Antimicrobial activity of A³IS and currently available anti-acne commercial products including some commercial products which incorporate antibiotics are shown. A³IS demonstrates a high level of comparable activity to commercially available anti acne products indicating the materials potential for topical acne application;

FIG. 10 shows the A³IS antimicrobial activity against 8 strains of MRSA on three different days and compared to a 10% phenol standard and to Manuka honey. Formulation A³IS is at normal pH 5.5 (test material A) and pH 7 (test material B), a negative control A³IS containing no GOX is included. The results demonstrate significant in vitro anti-MRSA efficacy and the superiority of A³IS over Manuka honey and a 10% phenol gel control;

FIG. 11a shows A³IS antimicrobial activity against MRSA compared to a 10% phenol standard and to Manuka honey. Formulation A³IS is at normal pH 5.5 (test material A) and pH 7 (test material B), a negative control A³IS containing no GOX is included. The results demonstrate significant in vitro anti-MRSA efficacy and the superiority of A³IS over Manuka honey and a 10% phenol gel control;

FIG. 11b shows the A³IS antimicrobial activity against clinical isolates of Mastitis compared to Antibiotics. A³IS inhibition assay (3 day repeats) compared to four antibiotics (Vancomycin, Streptomycin, Tetracycline and Chloramphenicol) when tested against 22 clinical isolates of Mastitis causing *Staphylococcus aureus* organisms. A³IS demonstrates superior in vitro efficacy to all of these antibiotics. Clinical isolate number 15 is resistant to Vancomycin, Streptomycin and Tetracycline and shows only mild sensitivity to Chloramphenicol, however, it demonstrates sensitivity to A³IS;

FIG. 11c shows the A³IS antimicrobial activity against clinical isolates of Mastitis compared to commercially available anti Mastitis products. A³IS inhibition assay (3 day repeats) compared to four of the leading commercially available anti mastitis multi antibiotic products when tested against 22 clinical isolates of Mastitis causing *Staphylococcus aureus* organisms. Formulation A³IS demonstrates comparable in vitro efficacy compared to three of the leading commercial products and is superior to one of these products;

FIG. 11d shows the A³IS antimicrobial activity against clinical isolates of Mastitis compared to a 2% Nisin Solution. A³IS inhibition assay (3 day repeats) compared to a 2% Nisin solution on 21 clinical isolates of Mastitis causing *Staphylococcus aureus* organisms. Formulation A³IS demonstrates superior in vitro efficacy to the 2% Nisin solution. Note: Clinical isolate number 15 of FIG. 11b was unrecoverable from storage and is not included in this assay;

FIG. 11e shows the development of Nisin Resistance. A 2% Nisin resistant colony (indicated by the arrow) within the zone of inhibition during a Nisin efficacy study. A³IS resistant colonies have never been observed;

FIG. 12a shows A³IS MTT toxicity assessment on NHFs (Normal Human Fibroblasts. Included in the assay are a 50% concentration of A³IS, a range of concentrations of commercial silver containing gel and a commercial zinc containing gel product, compared to sodium azide (positive control). A³IS demonstrates less toxicity than either the commercial silver containing gel or the commercial zinc containing gel product;

FIG. 12b shows A³IS MTT toxicity assessment on NHKs (Normal Human Keratinocytes). Included in the assay are a 50% concentration of A³IS, a range of concentrations of a commercial silver containing gel and a commercial zinc containing gel product, compared to sodium azide (positive control). A³IS demonstrates less toxicity than either the commercial silver containing gel or the commercial zinc containing gel product;

FIG. 12c shows A³IS agar overlay cytotoxicity assessment on L929 cells. Included in the assay are a 50% concentration of A³IS, a range of concentrations of a commercial silver containing gel and a commercial zinc containing gel product, compared to sodium azide (positive control). A³IS demonstrates less toxicity than either the commercial silver containing gel or the commercial zinc containing gel product;

Figure 13A:
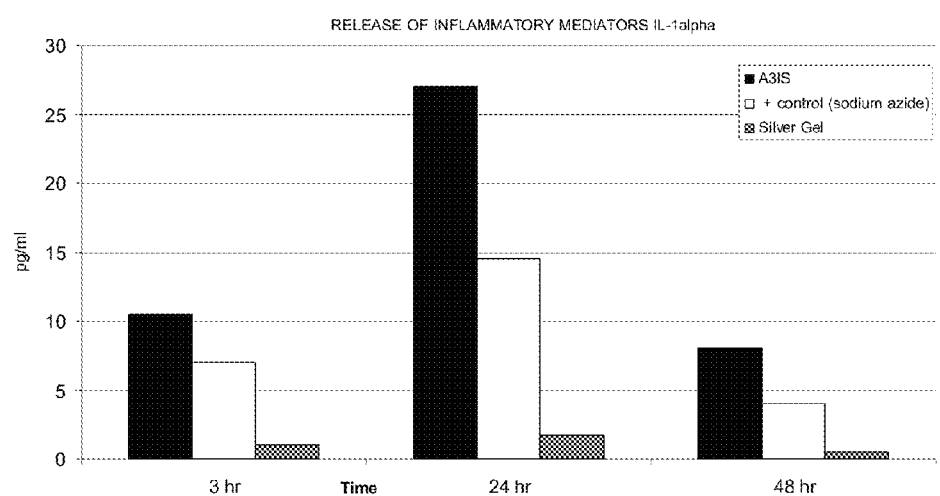
Figure 13B:
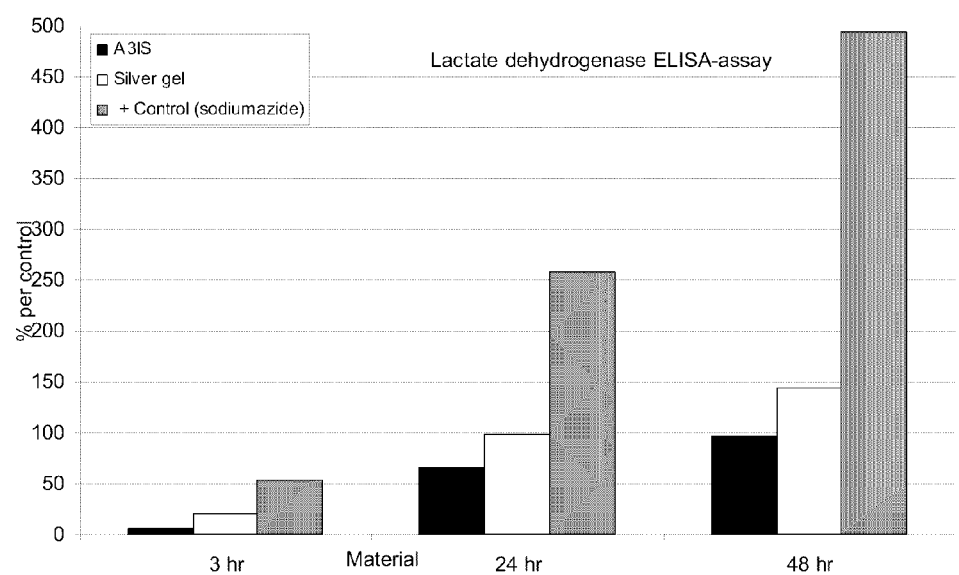
Figure 14:
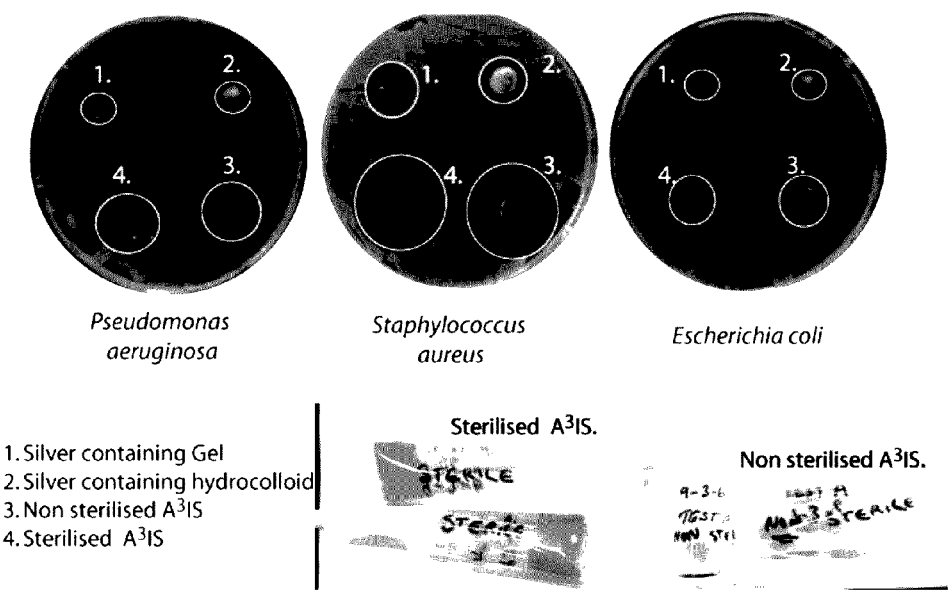
Figure 15A:
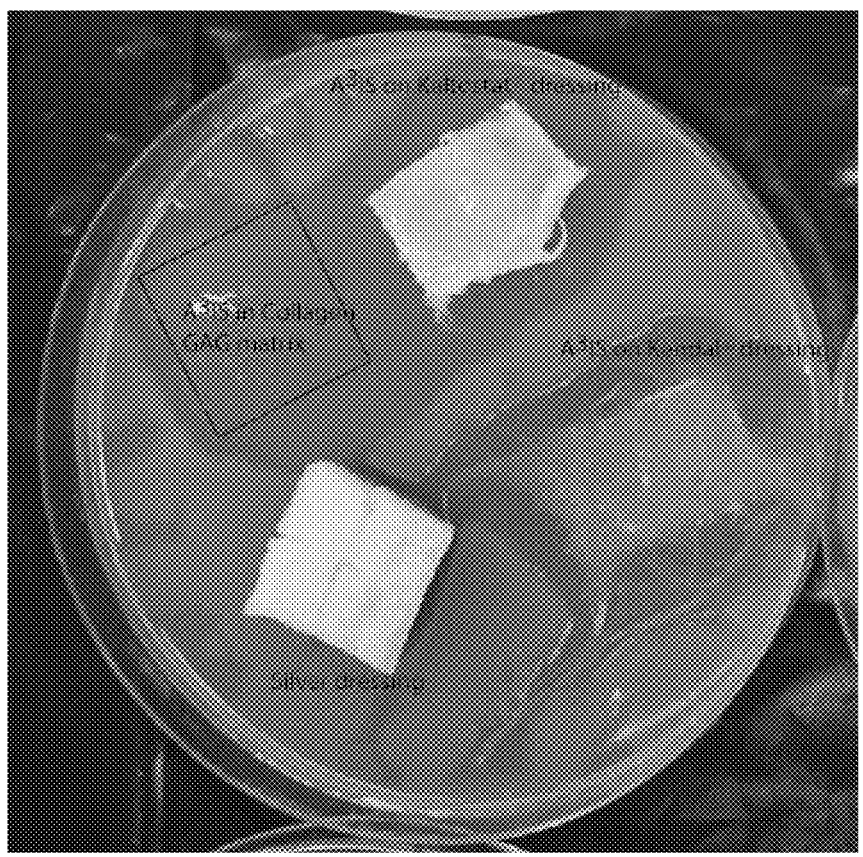
Figure 15B:
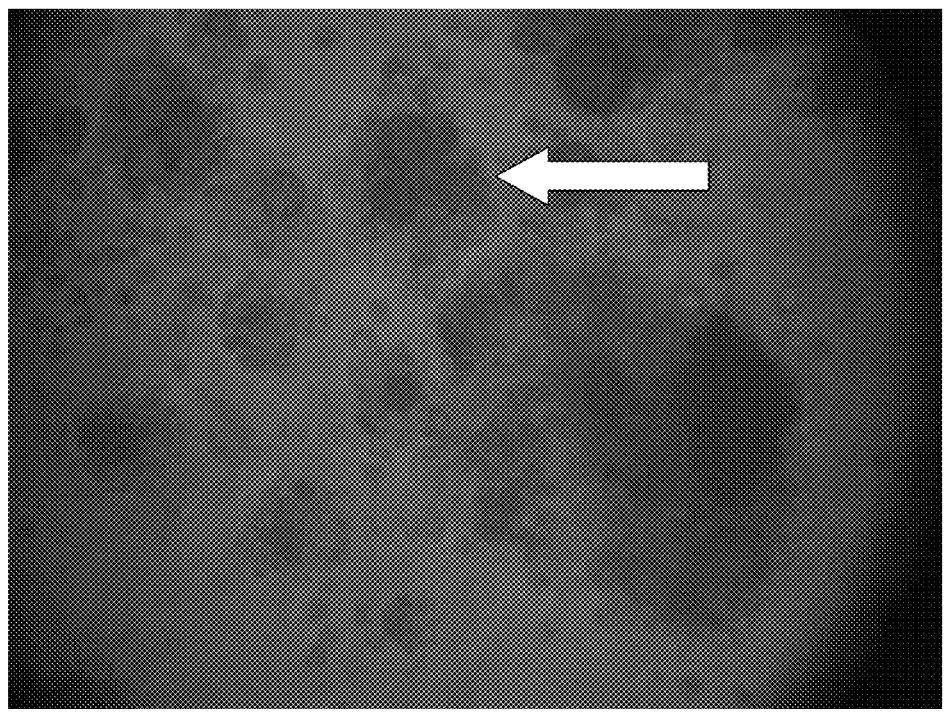
Figure 15C:
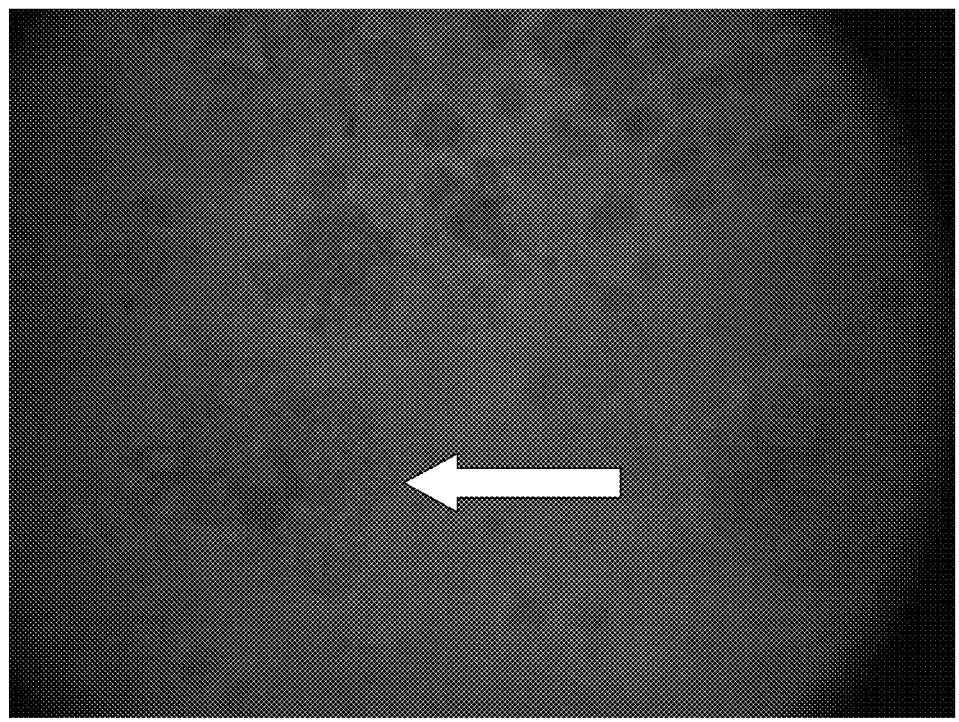

FIG. 13a shows induction of IL-1 release by A³IS. ELISA assay of the supernatant from a 3D irritancy assay over a 48 hour period, measuring and comparing the release of IL-1 when exposed to A³IS formulation, to a sodium azide positive control, and a commercial silver containing gel product. The results indicate that IL-1 is released from the skin cells exposed to the A³IS formulation;

FIG. 13b shows the induction of LDH release by A³IS. ELISA assay of the supernatant from a 3D irritancy assay over a 48 hour period, measuring and comparing the release of Lactate Dehydrogenase (LDH) when exposed to A³IS, a sodium azide positive control, and a commercially available silver containing gel product. Lactate dehydrogenase is released by cells exposed to destructive compounds. The results indicate that the A³IS formulation is less toxic than commercially available silver containing gel products;

FIG. 14 shows A³IS before and after sterilisation by Gamma irradiation. Gamma irradiation does not reduce activity as shown by zone of inhibition assays on *S. aureus*, *E. coli* and *Pseudomonas aeruginosa*;

FIG. 15a shows A³IS in a Collagen-GAG matrix and in commercial wound dressings tested for antibacterial activity against *S. aureus*. A³IS demonstrates antibacterial activity which is superior to that observed with a commercially available silver dressing used as a control;

FIGS. 15b and 15c show collagen-GAG matrix infiltration by NHFs. Infiltration by NHFs of the Collagen-GAG matrices. Over a 4 day period following addition of test sections NHFs are observed to attach to and grow within and along the Collagen-GAG matrices as indicated by the arrow.

Figure 16A:
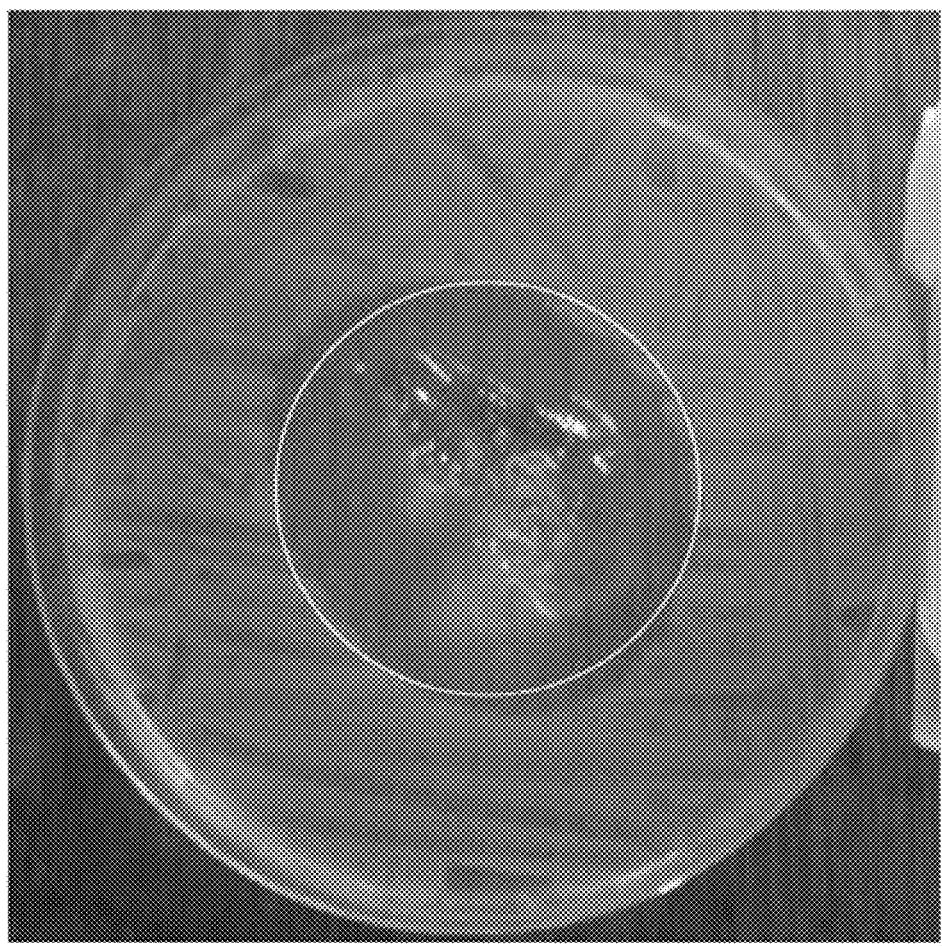
Figure 16B:
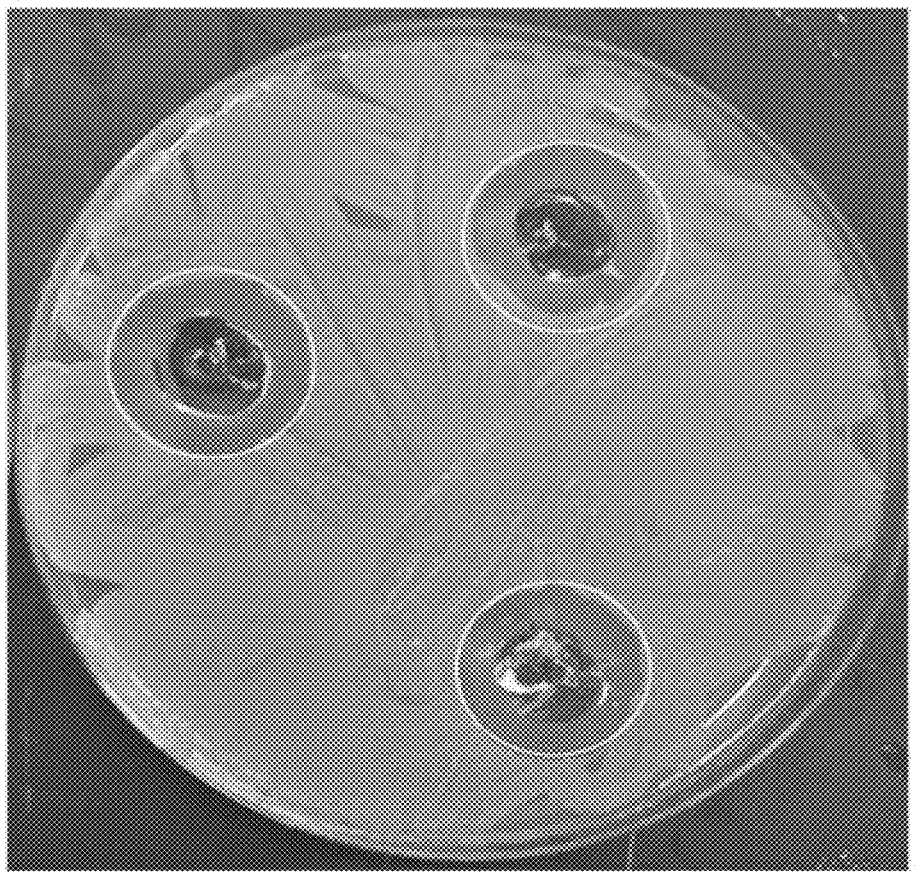
Figure 17:
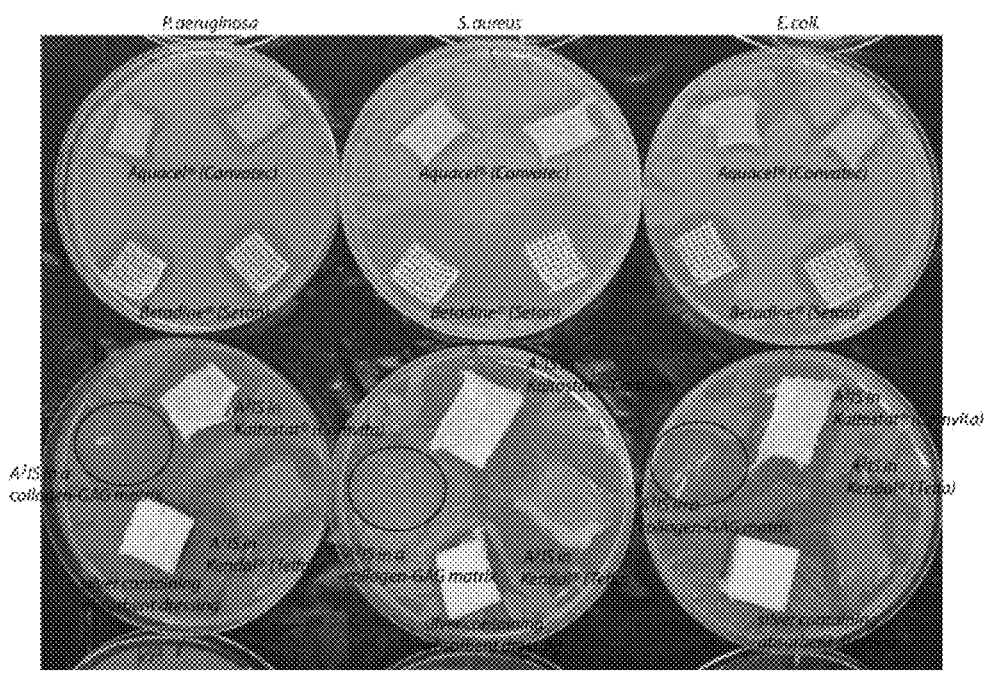
Figure 18A:
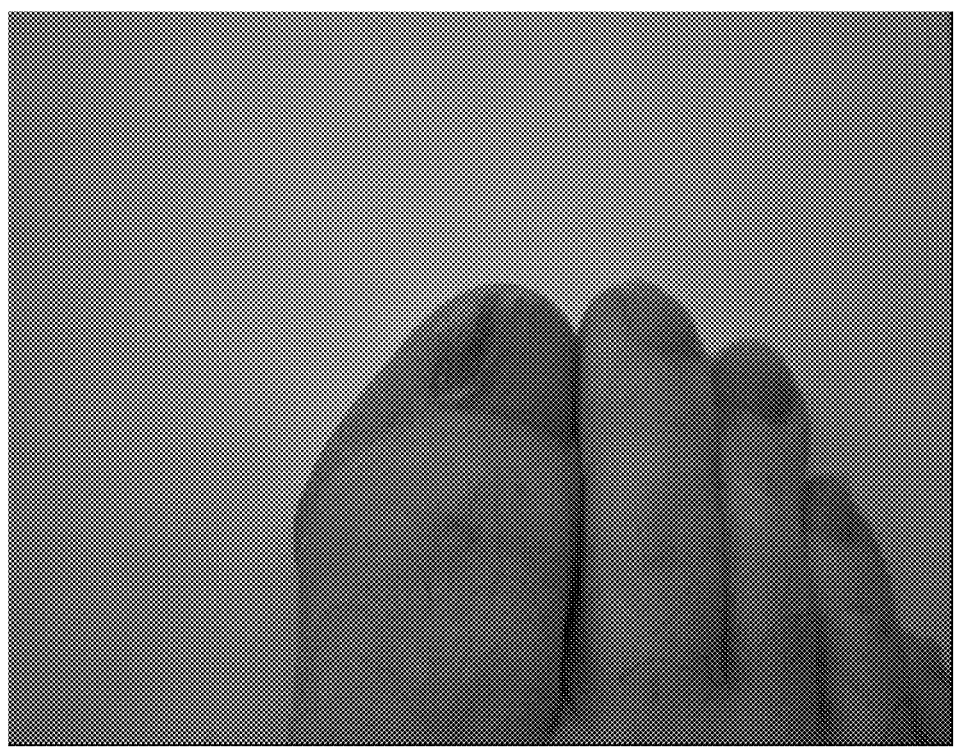
Figure 18B:
Figure 18C:
Figure 18D:
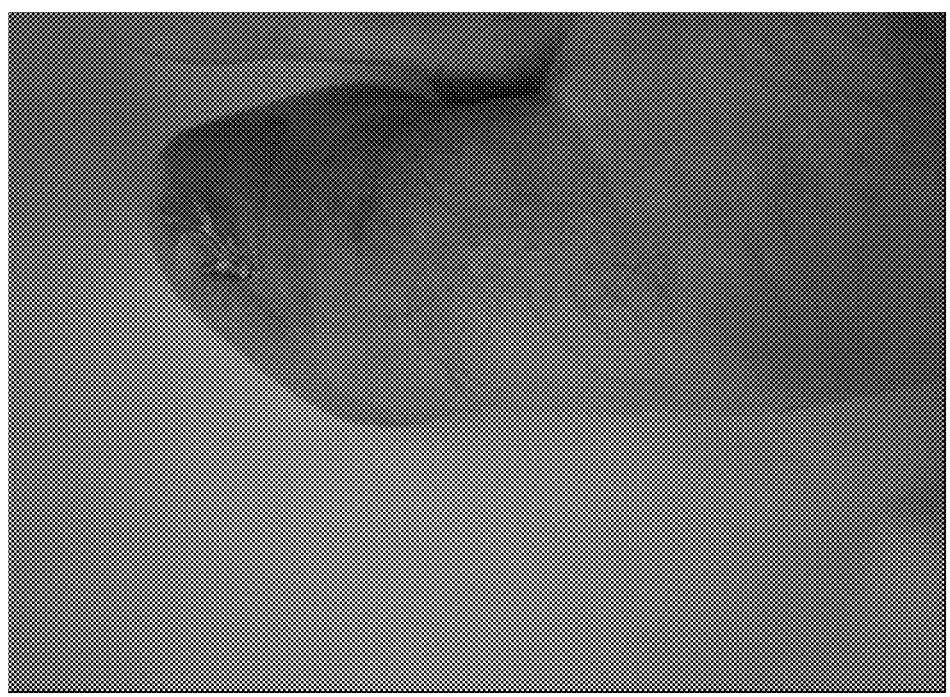

FIG. 16a shows A³IS in an alcoholic gel tested using the surface diffusion bio assay to determine zones of inhibition against *S. aureus*. Zones of inhibition are small due to the absorptive property of the gel matrix, but there is a clear zone around the gel matrix;

FIG. 16b shows A³IS—stability in an alcoholic gel. The A³IS in an alcoholic gel formulation was put on a short term stability study of 6 weeks, including a freeze thaw cycle and tested using the surface diffusion bio assay to determine zones of inhibition against *S. aureus*. Results indicated that the gel formulation maintained stability throughout the test period;

FIG. 17 shows a comparative investigation of A³IS efficacy. A³IS was poured onto the surface of a range of commercially available dressings Kaltostat® (Comvita), Kendal® (Telfa) and a Collagen-GAG (glycosaminoglycan) matrix as previously described and allowed to diffuse into the dressing for several hours. Sections were cut and placed onto agar plates, previously inoculated with *S. aureus*, *E. coli* and *P. aeruginosa*. The antibacterial efficacy of A³IS impregnated dressings was then compared to Aquacel® (Convatec) and Betadine® (Seton) commercially available dressings that contain elemental silver and iodine. A³IS dressings are as effective antimicrobially as Aquacel® (Convatec) and Betadine® (Seton) and a commercially available dressing that use elemental silver and iodine;

FIG. 18a shows A³IS—antimicrobial activity against Onychomycosis. Onychomycosis present in a toenail prior to treatment with A³IS;

FIG. 18b shows A³IS—antimicrobial activity against Onychomycosis. A³IS covered with a bandage whose wadding is moistened using water. The nail is therefore covered in an occlusive dressing;

FIG. 18c shows A³IS—antimicrobial activity against Onychomycosis. Photograph 48 hours after initiation of A³IS treatment. It is evident that the nail has changed appearance in that it is now darker in colour; and FIG. 18d shows A³IS—antimicrobial activity against Onychomycosis. Photograph 8 weeks after initiation of A³IS treatment. In this the band of uninfected nail is clearly visible, indicating that the dermatophytes have been eliminated.

Figure 19:
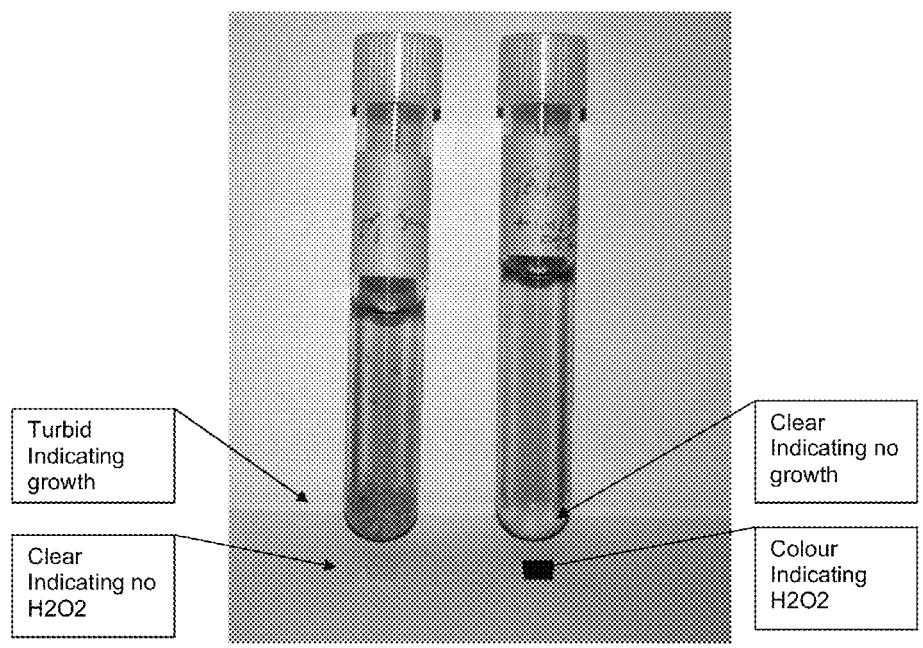

FIG. 19 shows the results of Example 19. The test tube on the left of FIG. 19 is the control and it is evident that there is significant growth of the organism as indicated by the clearly visible turbidity. The solution is not turbid in the test tube on the right of FIG. 19, thus, no *T. Rubrum* growth is evident. On this basis, we conclude that A3IS kills *T. Rubrum*. Thus, we have demonstrated that A3IS has both fungicidal and sporicidal activity.

Figure 20:
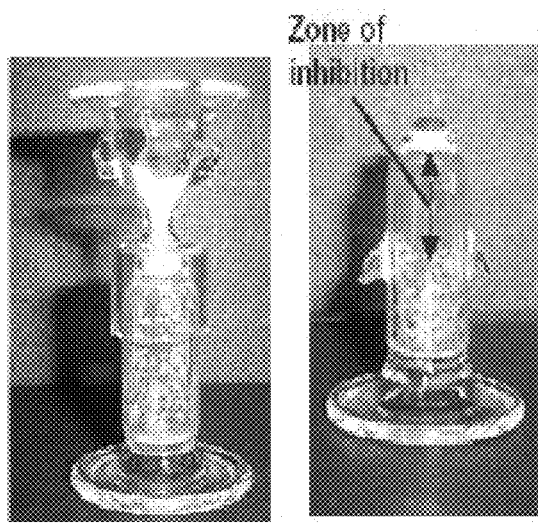

FIG. 20 shows modified Franz cells known as TurChub®.

Figure 21:
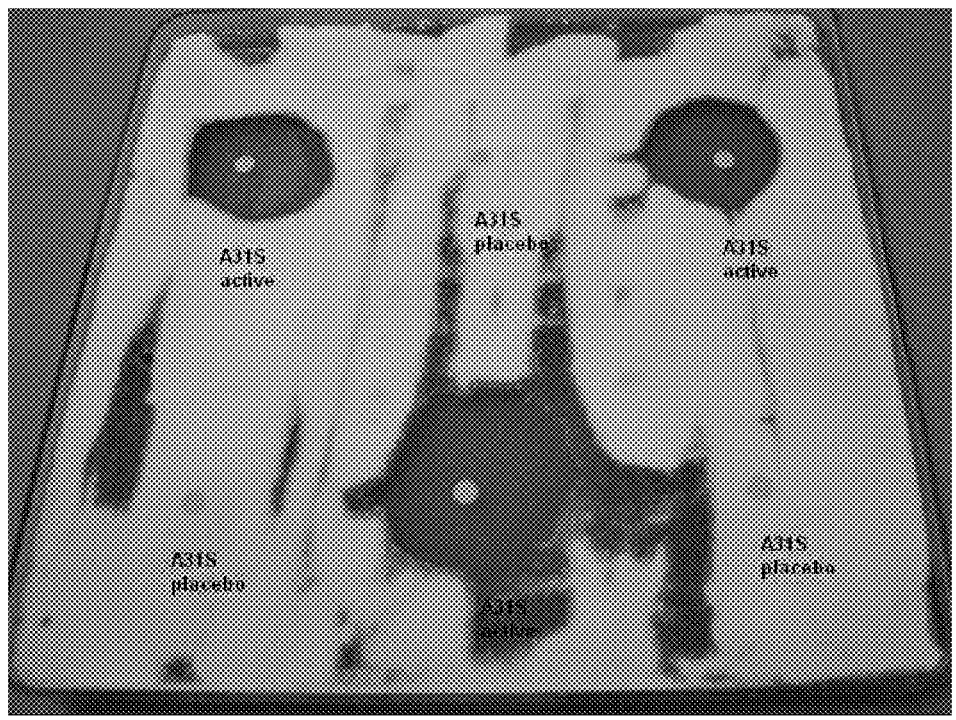

FIG. 21 depicts Disc diffusion Zone of Inhibition assay on SDA against *T. rubrum* with A³IS active and A³IS Placebo in accordance with Example 20. A large zone of inhibition indicates efficacy.

Figure 22:
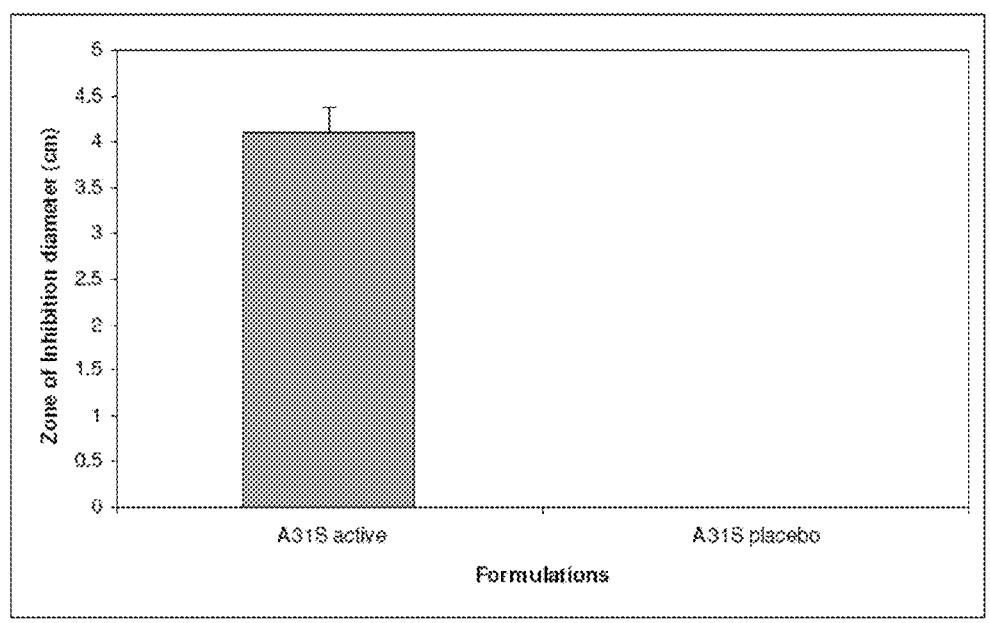

FIG. 22 shows the results of a comparison of the diameter (cm) of the ZOI using a standard disc diffusion assay of the A³IS active formulation and placebo with the organism *T. rubrum*, (245 mm square assay plate) (n=2).

Figure 23:
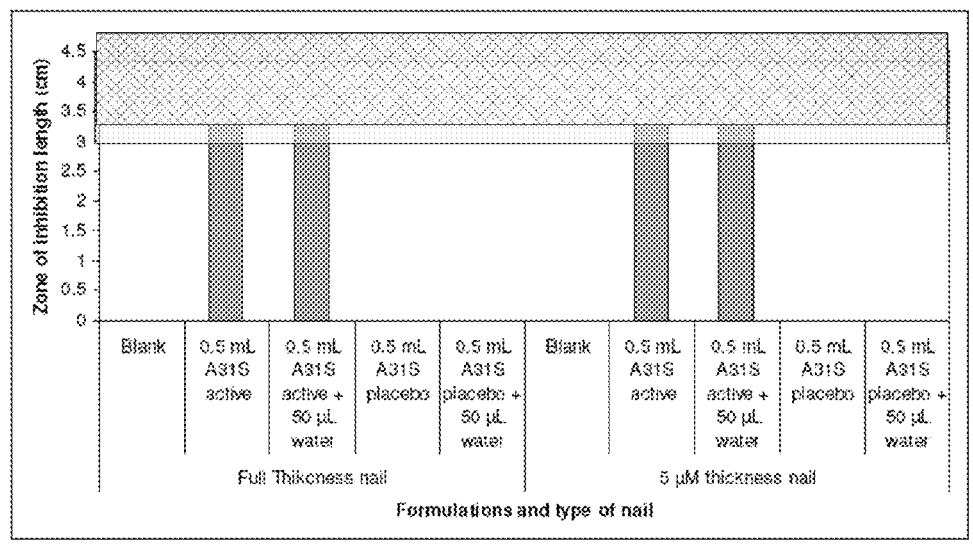

FIG. 23 and onwards show the results of Example 21.

FIG. 23 shows the results of a comparison of the average length of ZOI using the TurChub® test cell system with the organism *T. rubrum*, after applying 0.5 mL of the A³IS formulations to 5 μm thickness and full thickness (distal) human nail, (n=3). The hatched zone indicates that the maximum zone of inhibition for the cell has been reached (e.g. total kill). Included are blank cells, whereby no formulations were added to the surface of the respective nail samples.

Figure 24:
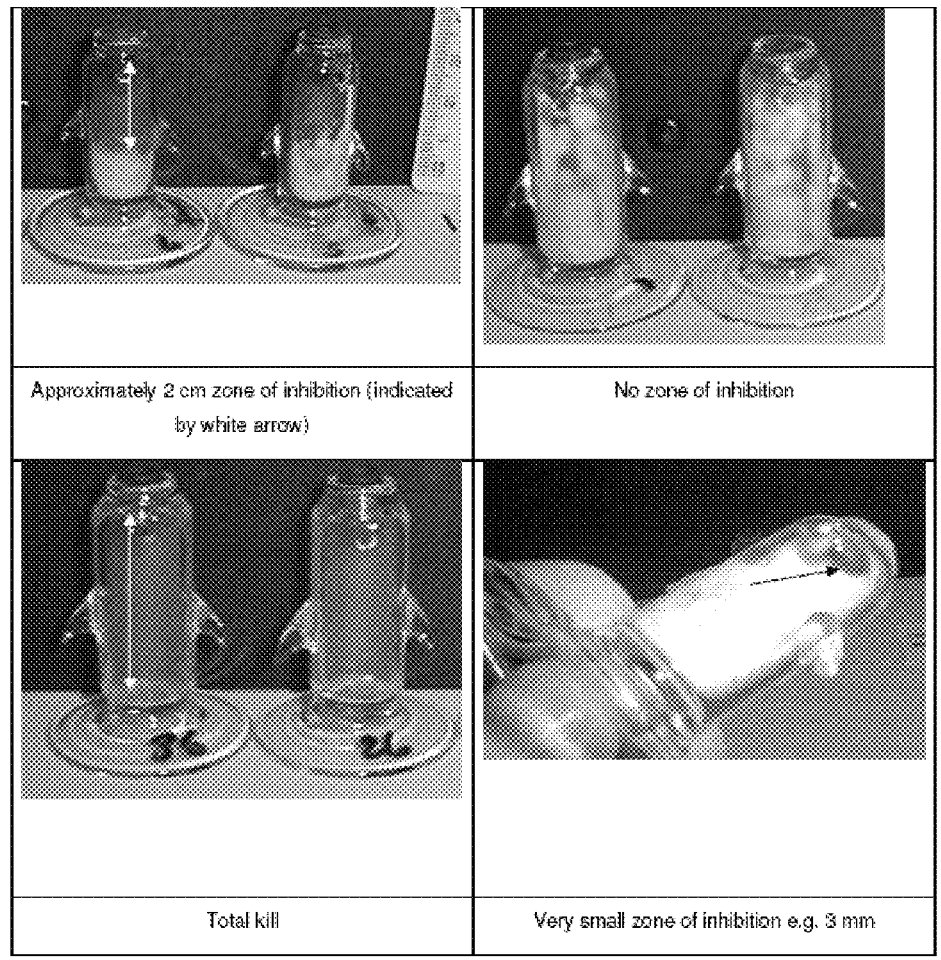

FIG. 24 shows four examples of typical zone of inhibition results observed in the TurChub® cell test system. In this assay inhibition is indicated by an inability of the organism to grow in the agar. From top left there is a zone of inhibition (clear agar) of approximately 2 cm. Top right indicates no zone of inhibition there is growth throughout the agar (cloudy). Bottom left indicates complete inhibition i.e. no growth of organism (the agar is clear). Bottom right indicates a very small zone of inhibition i.e. a 3 mm clear agar.

Figure 25:
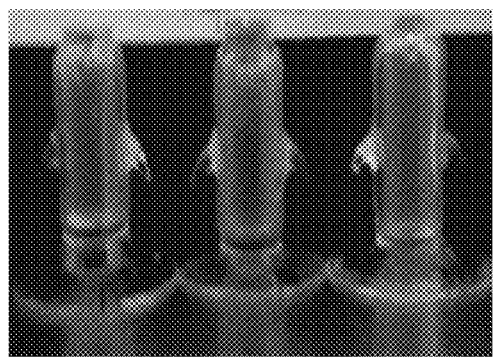

FIG. 25 shows 0.5 mL application of the formulation A3IS active at (T=0, 48 and 96 h) applied to the TurChub® test system with full thickness distal human nail with the organism *T. rubrum*.

Figure 26:
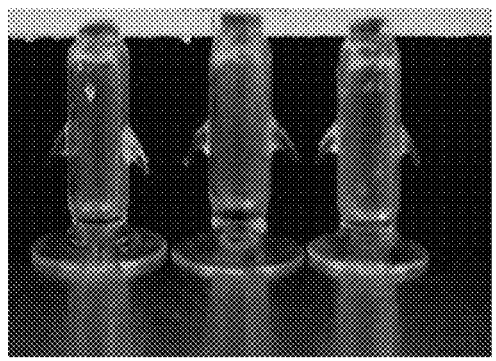

FIG. 26 shows 0.5 mL application of the formulation A3IS active+water at (T=0, 48 and 96 h) applied to the TurChub® test system with full thickness distal human nail with the organism *T. rubrum*.

Figure 27:
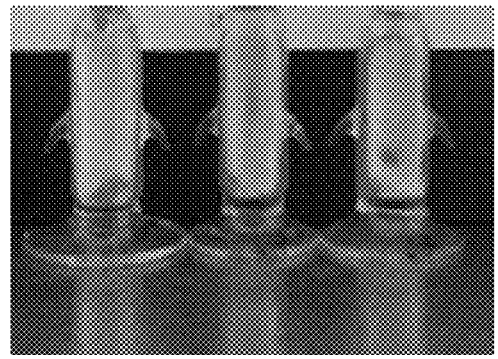

FIG. 27 shows 0.5 mL application of the formulation A3IS placebo at (T=0, 48 and 96 h) applied to the TurChub® test system with full thickness distal human nail with the organism *T. rubrum*.

Figure 28:
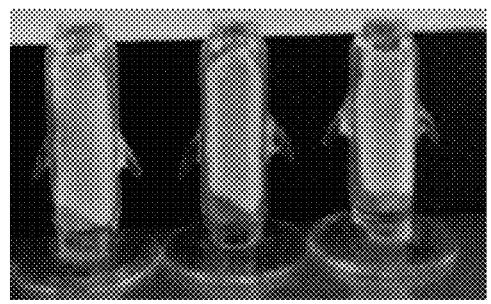

FIG. 28 shows 0.5 mL application of the formulation A3IS placebo+water at (T=0, 48 and 96 h) applied to the TurChub® test system with full thickness distal human nail with the organism *T. rubrum*.

Figure 29:
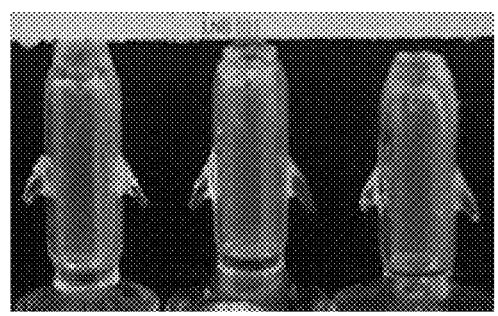

FIG. 29 shows 0.5 mL application of the formulation A3IS active at (T=0, 48 and 96 h) applied to the TurChub® test system with 5 μM human nail with the organism *T. rubrum*.

Figure 30:
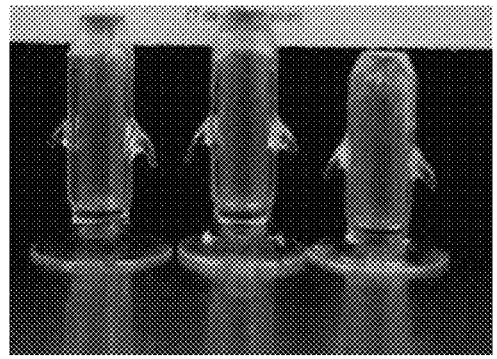

FIG. 30 shows 0.5 mL application of the formulation A3IS active+water at (T=0, 48 and 96 h) applied to the TurChub® test system with 5 μM human nail with the organism *T. rubrum*.

Figure 31:
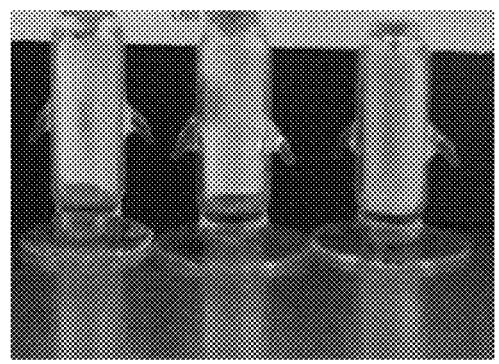

FIG. 31 shows 0.5 mL application of the formulation A3IS placebo at (T=0, 48 and 96 h) applied to the TurChub® test system with 5 μM human nail with the organism *T. rubrum*.

Figure 32:
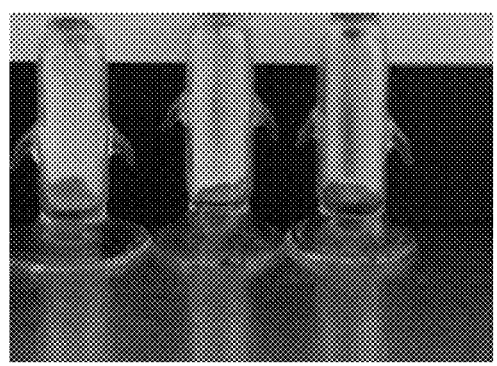

FIG. 32 shows 0.5 mL application of the formulation A3IS placebo+water at (T=0, 48 and 96 h) applied to the TurChub® test system with 5 μM human nail with the organism *T. rubrum*.

Figure 33:
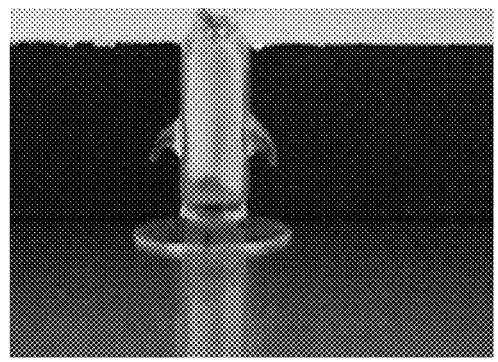

FIG. 33 shows untreated control—TurChub® test system with full thickness distal human nail with the organism *T. rubrum*.

Figure 34:
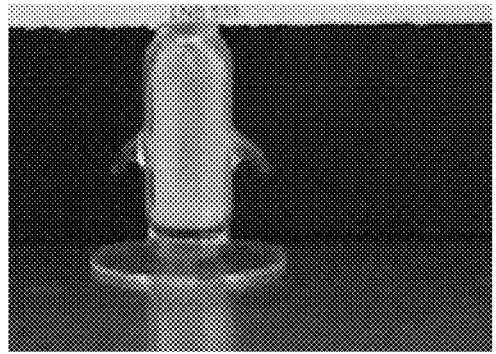

FIG. 34 shows untreated control—TurChub® test system with 5 μM human nail with the organism *T. rubrum*.

EXAMPLES

General Materials and Methods

Manuka Honey:

Manuka Care 18+® (Comvita) or Medihoney® was prepared as a 50% v/v in nutrient broth. 11 serial 1 in 2 dilutions of the 50% v/v preparation were made in nutrient broth and used for microbial inhibition testing, giving a lowest concentration of 0.01%.

Sugars:

(D+) glucose, (D−) fructose, (D+) maltose and (D+) sucrose (Sigma Aldrich)

Glucose Oxidase 0.5% glucose oxidase powder (5600 U/100 g) was used in the manufacture of $A^3IS$.

Glucose Oxidase 240 U/mg (Biozyme UK) (1 U is that amount of enzyme causing the oxidation of one micromole of glucose per minute at 25° C. and pH 7.0) and Glucose Oxidase 100 U/mg to 250 U/mg (Sigma Aldrich) (1 U will oxidize 1.0 mole of D-glucose to D-gluconolactone and $H_2O_2$ per min at pH 5.1 at 35° C.) were also used in the following Examples.

pH Adjustment:

A 50% v/v solution of Manuka honey was pH adjusted to pH6.5 with 1M NaOH and a sample of the sugar mix without glucose oxidase was pH adjusted to pH 3.8 with 1M HCl. pH was measured with a pH meter (Hanna Instruments HI 931410).

Single Sugar Preparations:

50% w/v solutions of glucose only, fructose only, and sucrose only were prepared and serially diluted in a similar manner to the Manuka honey.

Measurement of Moisture Content and Available Water (Aw):

Determination of moisture content was made using a Carl Fisher Titration apparatus (Switzerland). Determination of Aw was made using an Aqua Lab Aw meter, model series 3TE, Decagon Devices Inc. Pullman, Wash., (Kind permission Glanbia Innovation Centre, Kilkenny).

$H_2O_2$ Assay:

Hydrogen peroxide was determined following the method of (Kerkyliet 1996 and Serrano et al., 2004), using Merckoquant test strip (no. 10011; Merck, Germany).

Removal of $H_2O_2$:

Catalase (Sigma Chemical Co., from bovine liver, cat. No. C-30. 12,800 U/mg) was added to normal pH Manuka honey dilutions (initial pH 4) and to pH adjusted Manuka honey dilutions (initial pH 6.8) at the same concentrations used by Taormina et. al., Allen et. al., and Molan et. al. 1988). Typically the concentration added is 100 times greater than the measured amount of $H_2O_2$ present.

Heat Treatment of Manuka Honey:

A 50% solution of Manuka honey in nutrient broth was heat treated to a temperature of 85+/−5° C. in a water bath, this temperature was maintained for a period of 60 minutes or 120 minutes. A 50% solution of Manuka honey in nutrient broth was autoclaved at 121 psi for 15 minutes. From these heat treated honey preparations dilutions were prepared for assay.

Microbial Strains:

*Escherichia coli* (NCIMB 8545), *Staphylococcus aureus* (NCIMB 9518) and *Pseudomonas aeruginosa* (NCIMB 8626) are grown on nutrient agar or in nutrient broth for 24 hrs at 37° C.

*Candida albicans* (NCIMB 3179) and *Saccharomyces cerevisiae* are grown on sabaroud dextrose agar or in sabaroud dextrose broth for 24 hrs at 37° C.

*Propionibacterium acnes* (*P. acnes* ATCC/NTC 11827) is grown anaerobically on blood agar or in nutrient broth for 72 hrs at 37° C.

22 isolates of *Staphylococcus aureus* from clinical mastitis obtained from Sligo regional Veterinary Laboratories are grown on nutrient agar or in nutrient broth for 24 hrs at 37° C.

For testing conducted in the Sligo Regional General Hospital; five Beta haemolytic Streptococci Group A clinical isolates are grown on blood agar or in nutrient broth for 24 hrs at 37° C.

*Campylobacter coli* (NCTC 11366) is grown on brain heart infusion agar or in brain heart infusion broth for 72 hrs at 37° C.

*Campylobacter jejuni* (NCTC 11322) and three clinical isolates are grown on brain heart infusion agar or in brain heart infusion broth for 72 hrs at 37° C.

MRSA (ATCC 43300) and seven clinical isolates are grown on nutrient agar or in brain heart infusion broth for 72 hrs at 37° C.

Laboratory mould isolates are grown on sabaroud dextrose agar or in sabaroud dextrose broth for 48 hrs at 25° C.

*Botrytis cinerea* is grown on sabaroud dextrose agar or in sabaroud dextrose broth for 48 hrs at 25° C.

Bacterial growth is monitored by measuring the culture optical density (OD) in a spectrophotometer (Anthos 2010) at a wavelength of 620 nm.

*Trichophyton rubrum* ATCC 28188, grown on sabaroud dextrose agar (SDA)

Well/Disc Diffusion Methods—for Measurement of Microbial Inhibition

Agar plates are inoculated by swabbing overnight culture onto the plate surface. Plates are allowed to stand at room temperature for 15 minutes before use. Wells 8.2 mm diameter are bored into the surface of the agar. One hundred and eighty µl of sample is placed into each well. The samples diffuse into the agar around the well and are assayed for an ability to produce a zone of inhibition. Plates are incubated for 24, 48 or 72 hrs and zones of inhibition are measured using an Autodata automatic zone reader. The diameter of zones, including the diameter of the well (8.2 mm), is recorded.

For disc assays, sterile absorbent discs (8.2 mm diameter) are placed into sample dilutions for 10 minutes before being applied directly to inoculated agar plates. The samples diffuse from the disc into the agar and are assayed for an ability to produce a zone of inhibition. Plates are incubated for 24, 48 or 72 hrs and zones of inhibition are measured using an Autodata automatic zone reader. The diameter of zones, including the diameter of the disc (8.2 mm), is recorded.

Honey Bactericidal Quantifications

The agar diffusion assay (ADA) is generally the preferred method for honey bactericidal quantifications and determining biological potency for compounds/actives—antibiotics, and is used for Manuka honey production batch analysis and release procedures (Gribbles Analytical Laboratories Kerkyliet, J. D., 1996. Screening method for the determination of peroxide accumulation in honey and relation with UMF content (*Journal of Apiculture Research*. 35, 3, pp. 110-117). However, the subjective nature of this assay limits the interpretation of results. It is also time consuming and laborious, requiring preparation and cooling of plates, boring of test wells in agar and manual measuring of inhibition zones after 24 hrs of incubation. The quality of results depend largely on technique and judgment, and the suggested precision cannot be obtained when the inhibition zone is unclear or not perfectly circular.

Other Methods—for Measurement of Microbial Inhibition

Microbial growth, or inhibition of growth, can be detected using a variety of biological methods, including, direct microscopic counts, absorbance, bioluminescence, assays that incorporate a colorimetric, and fluorometric growth indicator, turbidity, dry weight and zones of inhibition.

Spectrophotometric Assay

We developed a spectrophotometric assay using 96 well microtiter plates (Patton T. et al Journal of Microbiological Methods (2006) pages 84-95) and compared this method to the standard methods of well/disc diffusion in order to evaluate the potential advantages of this bioassay for evaluation of the antibacterial properties of Manuka honey. Increased automation and throughput (efficiency) were achieved using the spectrophotometric assay which can rapidly generate large amounts of data making possible a detailed statistical analysis of results. The method is more sensitive, and more amenable to statistical analysis than the assays currently employed, permitting extensive kinetic studies even in the presence of low honey concentrations (Table 1). The assay is capable of detecting inhibitory levels below that recorded for well or disc diffusion assays. This assay provides a quick and sensitive method for elucidating the activity of Manuka honey.

TABLE 1

MIC50 values indicate percent Manuka honey present resulting in a 50% inhibition in growth of a test micro-organism.

| Microbial species | Disc Assay MIC50 | Well Assay MIC50 | Spectro-photometric Assay MIC50 |
|---|---|---|---|
| Escherichia coli | 22.4% | 24.5% | 5.6% |
| Staphylococcus aureus | 25.7% | 22.6% | 0.78% |
| Bacillus cereus | 24% | 21.9% | 2.00% |
| Candida albicans | No inhibition | No inhibition | 40% |

Honey dilutions are inoculated with a 5% v/v of overnight test culture. Two hundred microliters of each dilution, using 8 replicates per dilution, are applied to wells of a flat bottom 96 well microtiter plates with lid to prevent cross contamination (Costar, Corning Ltd. NY). Control wells received 200 microliters of 5% culture inoculated broth. Optical density is determined in a spectrophotometer at 620 nm prior to incubation, ($T_0$). Plates are incubated for 24 hrs in the dark on a Certomat MO orbital shaker at 100 rpm to prevent adherence and clumping. After 24 hrs plates are again read in a spectrophotometer at 620 nm, ($T_{24}$). Results shown are averages from eight determinations repeated five times on three separate days.

The OD for each replicate at $T_0$ is subtracted from the OD for each replicate at $T_{24}$. The adjusted OD of each control well is then assigned a value of 100% growth. The growth inhibition for the test wells at each dilution is determined using the formula:

Percent Inhibition=1−(OD test well/OD of corresponding control well)×100 for each row of the 96 well plate e.g. OD row 1, column 1, well 1 (test) is divided by the OD value of Row 1, column 12, well 12 (control).

This yields eight replicate inhibition values for each honey dilution. All assays are repeated a minimum of three times on three different days using a minimum of three plates per test, i.e. each data point reported is an average from a minimum of 72 point determinations.

The standard deviation associated with the average calculated inhibition values for replicate wells is determined and is plotted as associated error bars for each data point on graphs. Where the resulting measurement recorded a negative inhibition value (growth promotion) this is reported as stimulation using the formula:

Percent Growth=(OD test/OD control)×100.

Example 1

Figure 1A:
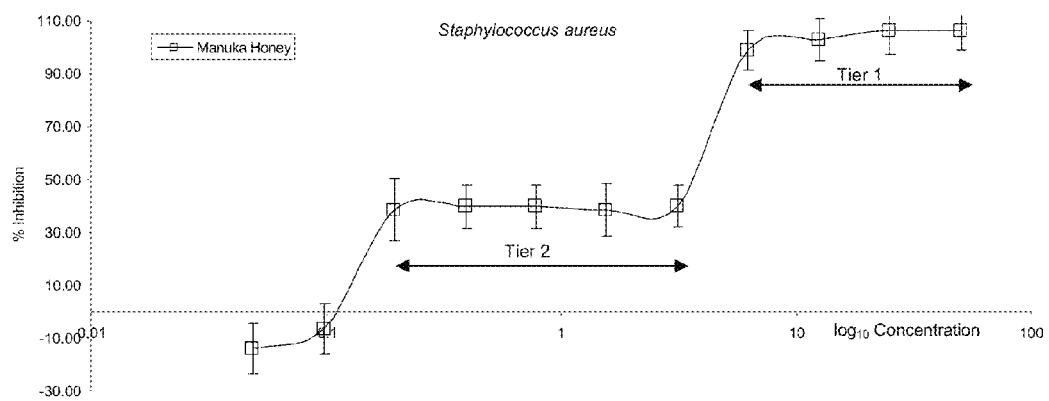

Characterisation of Antimicrobial Activities in Manuka Honey—Absence of Endogenous Hydrogen Peroxide Using the Spectrophotometric bioassay described, antimicrobial activity of commercially available Manuka honey is determined, using several samples to ensure consistency. Results shown in FIG. 1a demonstrate that Manuka honey provides a first tier of microbial inhibition activity at dilutions 50% to approximately 6.25% and a second tier of microbial inhibition activity at dilutions 3.125% to approximately 0.195%

This two tier effect is shown to be produced by separate mechanisms. Initial microbial inhibition on low honey dilution (50%-6.25%) results from a combination of low pH and growth limiting Aw (Available Water) and a very minor role by hydrogen peroxide, which is only produced de-novo upon dilution and after a considerable period of time has elapsed. There is no detectable endogenous hydrogen peroxide present in diluted or undiluted Manuka honey, as shown in Table 2

TABLE 2

Manuka honey $H_2O_2$ generation profile

| % Dilution | 50.00 | 25.00 | 12.50 | 6.25 |
|---|---|---|---|---|
| Manuka honey | pH 3.89 | pH 4.35 | pH 4.96 | pH 5.95 |
| $H_2O_2$ mg/L (Time 0 hrs) | 0 | 0 | 0 | 0 |
| Manuka honey | pH 3.89 | pH 4.35 | pH 4.96 | pH 5.95 |
| $H_2O_2$ mg/L (Time 3 hrs) | 0 | 35 | 35 | 65 |

As the concentration of the honey is diluted, and after a period of time has elapsed, hydrogen peroxide is produced and further contributes to the antimicrobial effect.

Figure 1B:
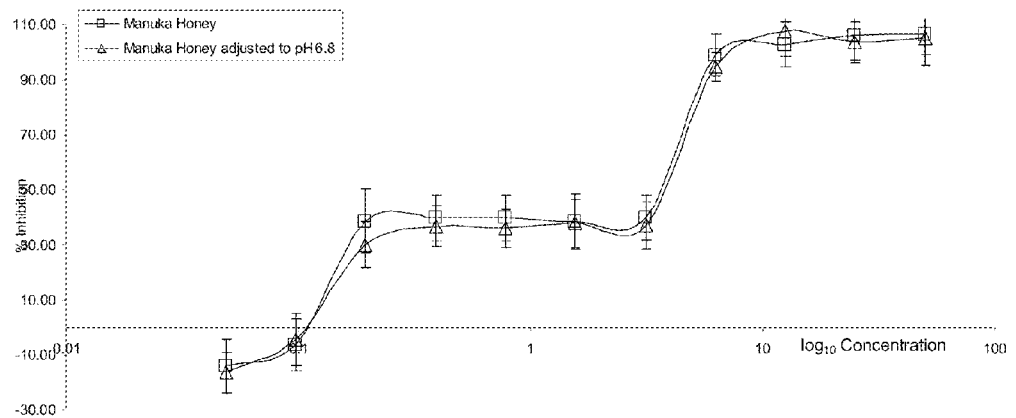
Figure 1C:
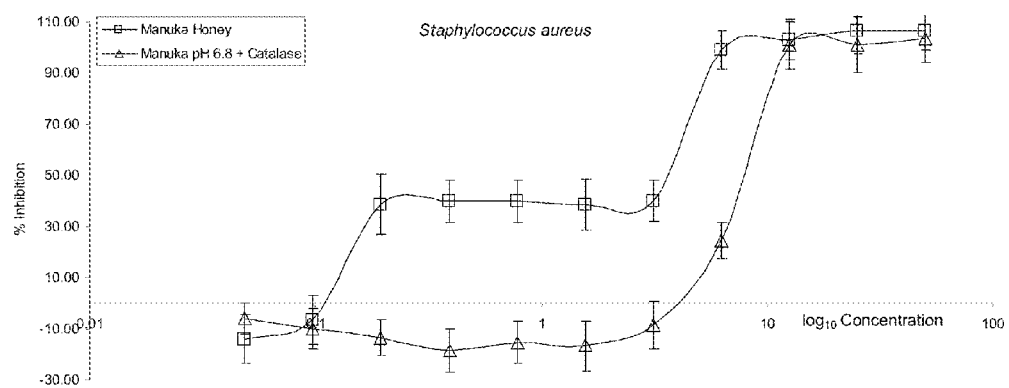

Adjusting the pH of Manuka honey from its natural pH of approximately 4.0 to a near neutral pH of 7.0 does not significantly affect the antimicrobial profile FIG. 1b. When Manuka honey dilutions are pH adjusted to near neutral followed by the addition of catalase in excess, the antimicrobial profile of the honey is altered FIG. 1c. The first tier of antimicrobial inhibition is only slighted affected but the second tier is significantly affected indicating that the antibacterial effect in the second tier is primarily the result of hydrogen peroxide liberation.

The belief that a non peroxide activity also referred to as Unique Manuka Factor (UMF) exists is due to an experimental procedural oversight. Specifically, the failure by other research groups to neutralise the pH of Manuka honey prior to catalase addition essentially renders the added catalase ineffective as the honey pH is too acidic for catalase activity. As honey to which excess catalase has been added still retains antimicrobial activity the belief that a UMF exists has persisted. As FIG. 1b shows, adjusting the pH of Manuka honey to pH 6.80 does not affect the antimicrobial activity. A pH of 6.80 is close to the optimum pH for catalase activity and under this condition the added catalase does neutralise the hydrogen peroxide activity thereby altering the antimicrobial activity profile of the honey.

Surprisingly, we also found that this glucose oxidase pathway is not operational immediately on application of Manuka honey and is only operational following dilution of the honey and after a period of time has elapsed.

Example 2

A Prototype Antimicrobial Endogenous and Sustained Release Hydrogen Peroxide Generating System A prototype formulation containing 31+/−5 g glucose: 35+/−5 g fructose: 7+/−2 g maltose: 1.5+/−1 g sucrose is made by mixing the ingredients, making the mixture up to a final volume of 100 ml in distilled deionized (DI) water; the mixture is sterilized by autoclaving. Glucose oxidase at 0.05% by weight, which is a similar concentration to that contained in Manuka honey, is added.

Figure 2:
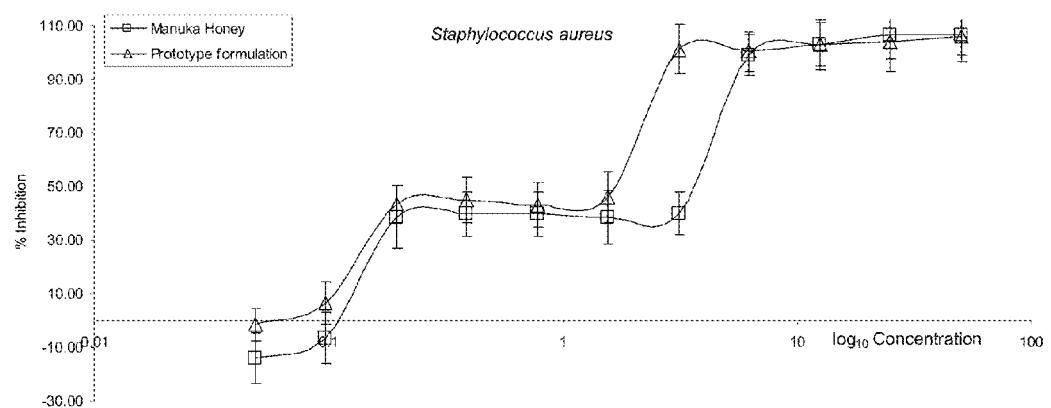

FIG. 2 shows the results of an antimicrobial assay on *S. aureus* using this prototype formulation. The prototype formulation of this example demonstrated a greater activity compared to Manuka honey. It is probable that the critical role played by the glucose oxidase enzymatic pathway in the antibacterial effect is enhanced once free from impurities and reaction limiting compounds (such as catalase) present in honey. This prototype demonstrates very effective bactericidal activity.

Example 2.1

Figure 3A:
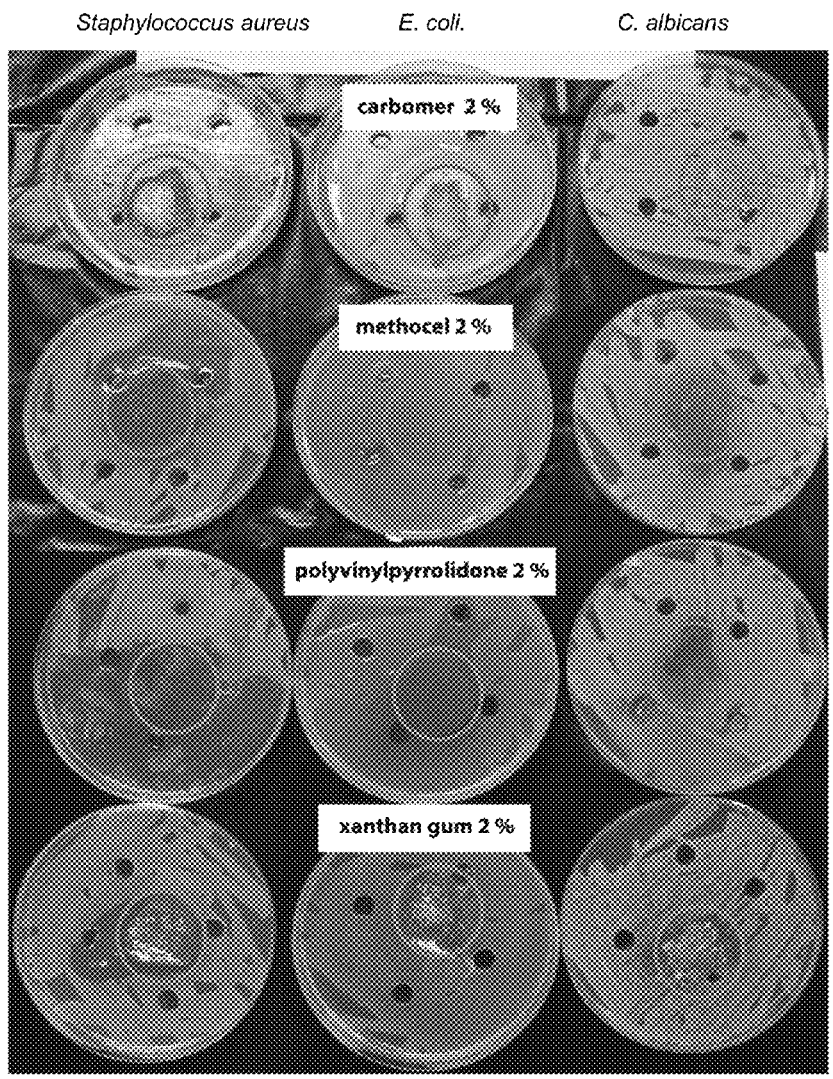
Figure 3B:
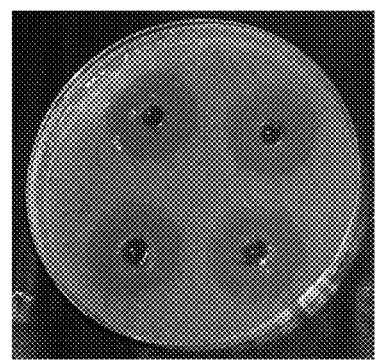

A Gel Prototype Antimicrobial Endogenous and Sustained Release Hydrogen Peroxide Generating System Gelling agents that are common ingredients in topical pharmaceutical formulations are added to the prototype formulation and tested. Gels tested include water reconstituted cellulose and alcohol reconstituted cellulose agents (1. carbomer, 2. methocel, 3. polyvinylpyrrolidone and 4. xanthan gum at 2% in a hydrogel incorporating the prototype formulation). Both cellulose based gels demonstrate a decrease in stability. It is possible that steric hindrance and hydrolysis of the glucose oxidase result in loss of antibacterial activity. Even before loss of activity, due to decreased stability, neither gel formulations is as active as the prototype formulation, as evidenced by the smaller zones of inhibition in diffusion assays (compare FIG. 3a (gels) with FIG. 3b (prototype formulation)).

Example 2.2

Figure 4A:
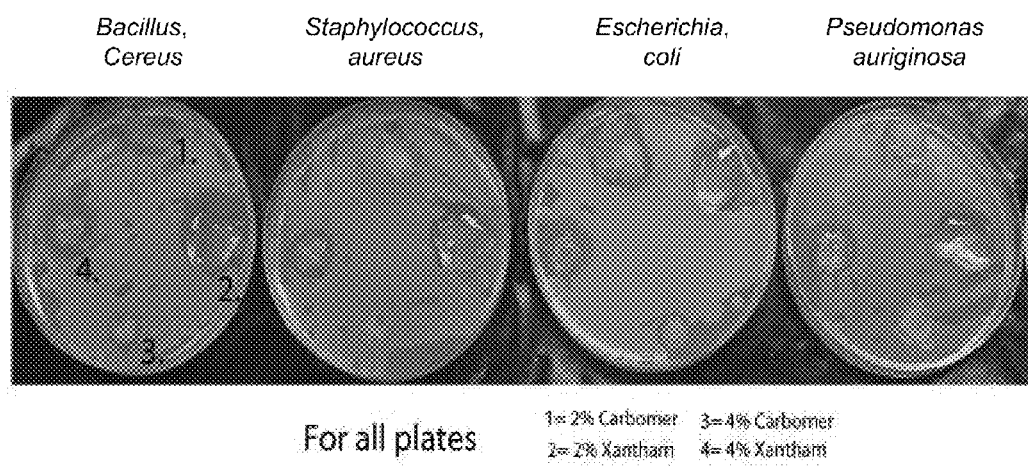

A Prototype Antimicrobial Endogenous and Sustained Release Hydrogen Peroxide Generating System—Single Sugar & Enzyme Gel Formulation In an attempt to resolve the gel stability described in Example 2.1, formulations containing glucose and glucose oxidase only are made. Glucose formulations ranging from 30%-80% glucose in water are autoclaved or warmed slowly to boiling point to aid in dissolution of the sugar. During dissolution by boiling, various gelling agents are added and when cooled to below 40° C. 0.1% glucose oxidase is added. These formulations are tested for antibacterial activity (FIG. 4a).

Figure 4B:
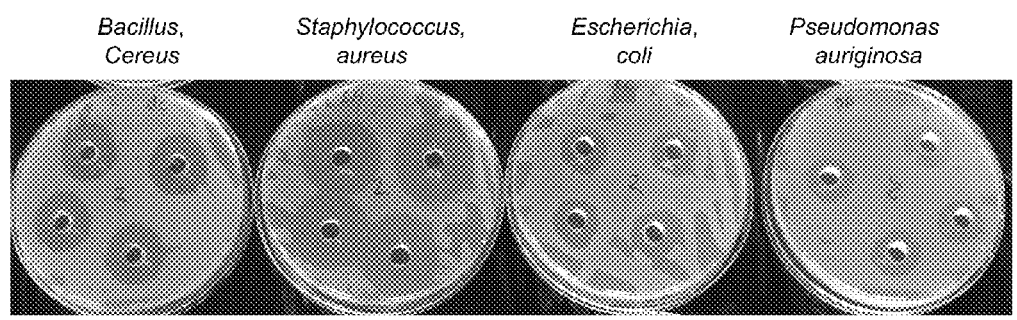

These formulations demonstrate only a limited degree of antibacterial activity and this activity is below that observed with the prototype antimicrobial formulation described in Example 2 as evidenced by the smaller zones of inhibition in Well/Disc diffusion assays (compare FIG. 4a (gels) with FIG. 4b (prototype)).

In addition to the reduced activity, the formulations containing the high glucose concentrations, when placed into aluminium tubes, solidify making the formulations unusable. The tubes containing formulations with lower concentrations of glucose demonstrate a lack of stability as evidenced by a decrease in antimicrobial activity over time.

Example 2.3

Improved Formulation Characteristics of Antimicrobial Endogenous and Sustained Release Hydrogen Peroxide Generating System—Varying the Carbohydrate and Water Concentration This example describes attempts to minimise the quantity of water present in formulations according to the invention, to minimise problems relating to stability as excess water may give rise to hydrolysis of the glucose oxidase. The formulations still require sufficient water to permit generation of $H_2O_2$, ease of application and to prevent precipitation of sugars during storage. Varying concentrations of sugars are mixed and heated as described in example 2.2 to determine the primary source for the precipitation and granular texture observed in earlier formulations. From this analysis, sugar concentrations are adjusted to reduce this effect. Following the addition of enzyme, suitable formulations are tested to determine antibacterial activity.

It is found that the concentration of water could be reduced from 20% to 10% which is the minimum concentration permitting enzyme activity, ease of application and prevention of sugar precipitation.

Uncontrolled heat treatment of sugars tends to produce carmelisation resulting in a formulation that acquires a yellow to brown colouration. To eliminate carmelisation, and thereby produce a clear material, a manufacturing process is developed in which the order of addition of sugars and their dissolution by heating is carefully selected to circumvent the carmelisation process. Glucose oxidase enzyme is added to this formulation and antibacterial activity, stability and suitability for application were assessed. These improvements to the Prototype formulation form the basis for all future formulations/systems described herein.

Example 3

Single Component Antimicrobial System, having an Endogenous Hydrogen Peroxide Reservoir and Sustained Release A formulation for a single component antimicrobial system (hereafter referred to as 'Antimicrobial System' or $A^3IS$ or A3IS is made in accordance with Table 3.

TABLE 3

| Ingredient | Percentage by weight |
|---|---|
| Purified water | 13.5 adjusted to make 100% |
| Fructose Powder | 35% +/− 5 |
| Glucose Powder | 38% +/− 5 |
| Maltose Powder | 10% +/− 5 |

TABLE 3-continued

| Ingredient | Percentage by weight |
|---|---|
| Sucrose Powder | 1.5% +/− 1 |
| Glucose Oxidase Powder | 0.5% enzyme (5600 U/g) pre-dissolved in 1.5% of purified water |
| TOTAL | 100% |

The pH of $A^3IS$ is set at pH 5.5. This low pH is within the glucose oxidase range of activity (pH 4.0-7.0 optimum pH of 5.5). If needed, a buffer can be added to obtain the desired pH, as illustrated in Table 4. The buffer is pre-dissolved in purified water and replaces part of the purified water from the formulation above.

TABLE 4

| Optional Buffering Ingredients for pH 5.5 | Percentage by weight |
|---|---|
| Citric Acid/Sodium Citrate | 0.918% pre-dissolved in 2% of purified water for pH 5.5 |
| Phosphoric Acid/Disodium hydrogen phosphate | 1.598% pre-dissolved in 2% of purified water for pH 5.5 |

It will be understood that different ratios of buffering ingredients can be used depending on the desired pH.

It will be understood that Prototype, described in Example 2 and $A^3IS$ described here give formulations suitable for use according to the invention. The subsequent Examples show analysis of various characteristics of $A^3IS$.

The sugars described in Table 3 are added in the following sequence: fructose, glucose, maltose and sucrose. Each carbohydrate is dissolved fully in the water by heating to approximately 90° C. before the next carbohydrate is added. Alternatively the sugars can be prepared as above but under a vacuum at −0.5 Bar, which reduces the boiling point of the sugars to a temperature of less than 90° C. preventing discoloration.

When the carbohydrates are fully dissolved and clear, the mixture is allowed to cool to below 60° C. and optional buffering ingredients pre-dissolved in water are added to the main mixture.

When the base mixture is at a temperature below 40° C., a temperature which allows retention of enzyme activity, the glucose oxidase enzyme which is pre-dissolved in water is added and dispersed into the mixture. The mixture is allowed to cool to room temperature. When cool, the mixture is dispensed into aluminium tubes which are then sealed. Tubes are stored at room temperature.

Example 3.1

A Prototype Antimicrobial Endogenous and Sustained Release Hydrogen Peroxide Generating System—Varying the Enzyme Concentration and Type Honey is known to contain several enzymes in addition to glucose oxidase, including diastase and invertase. Diastase and invertase enzymes are incorporated into the prototype formulation of Example 2 to determine if they can enhance overall antibacterial activity by allowing for a slower but sustained release of $H_2O_2$ by acting on different carbohydrates in the formula.

We investigate several combinations and concentrations of enzyme to determine this potentially enhanced antibacterial activity. Diastase and invertase in differing combinations are added to the $A^3IS$ and compared to $A^3IS$ containing glucose oxidase only. We find no improvement in antibacterial activity in any of the formulations containing multi enzymes.

Figure 5A:
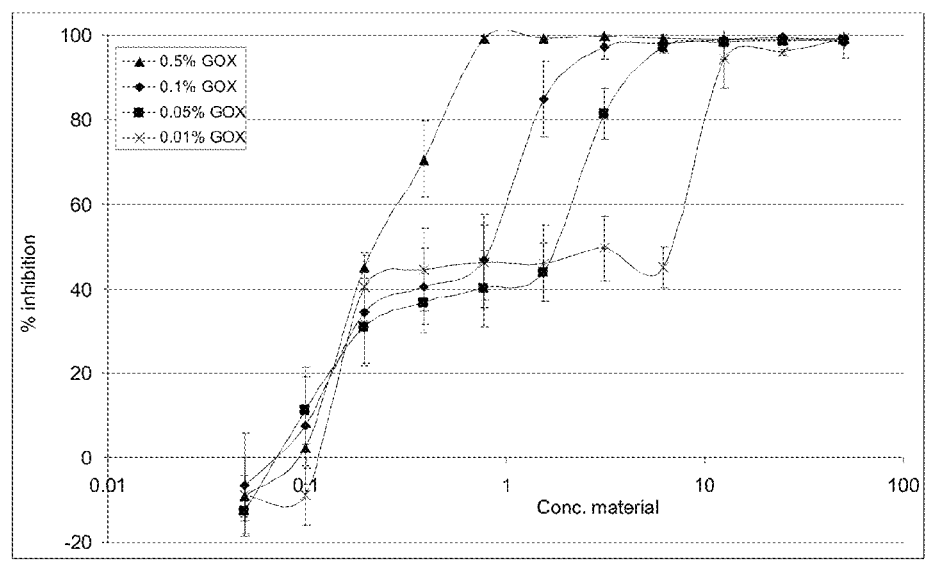

Different concentrations of glucose oxidase are also incorporated and compared by spectrophotometric assay to determine their quantity/activity relationship. The antibacterial activity of $A^3IS$ increases proportionally to the concentration of glucose oxidase. A substantial antibacterial effect is attained at an enzyme concentration of 0.05% (FIG. 5a).

This shows that a range of antibacterial activity can be achieved by varying the concentration of glucose oxidase. The enzyme can be dispersed with ease throughout the material during mixing.

Example 4

$A^3IS$—An Innovative and Augmented Hydrogen Peroxide Generating System

Hydrogen peroxide is quantified following the method of (Kerkyliet 1996 and Serrano et al., 2004), using Merckoquant test strip (no. 10011; Merck, Germany). Results are expressed in milligrammes $H_2O_2$ per liter. The suitability of the method for hydrogen peroxide determination is verified by spiking freshly prepared Manuka honey dilutions with liquid $H_2O_2$ and verifying that the assay could accurately detect the quantity of $H_2O_2$ present.

Figure 5B:
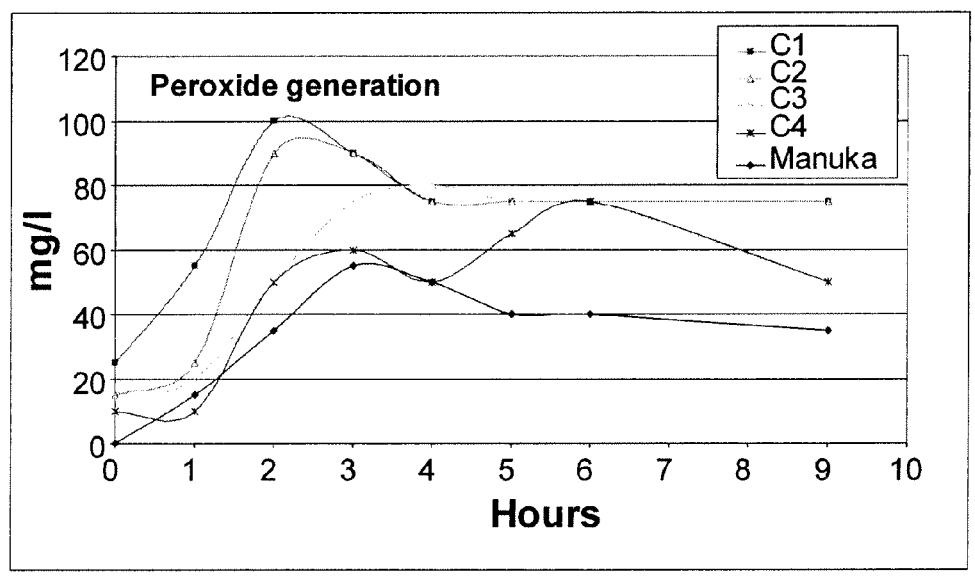

Table 5 and FIG. 5b show that $A^3IS$, with 0.5% sigma Aldrich GOX enzyme 5600 U/g and diluted 50% (C1), 25% (C2), 12.5% (C3) or 6.25% in de-ionised water (DI) generate significantly increased levels of hydrogen peroxide compared with Manuka honey diluted at 50% in DI water.

TABLE 5

| | Sample/ mg H2O2/l | | | | |
|---|---|---|---|---|---|
| Time hr. | C1 | C2 | C3 | C4 | Manuka |
| 0 | 25 | 15 | 15 | 10 | 0 |
| 1 | 55 | 25 | 20 | 10 | 15 |
| 2 | 100 | 90 | 50 | 50 | 35 |
| 3 | 90 | 90 | 75 | 60 | 55 |
| 4 | 75 | 75 | 80 | 50 | 50 |
| 5 | 75 | 75 | 75 | 65 | 40 |
| 6 | 75 | 75 | 75 | 75 | 40 |
| 9 | 75 | 75 | 50 | 50 | 35 |

Figure 5C:
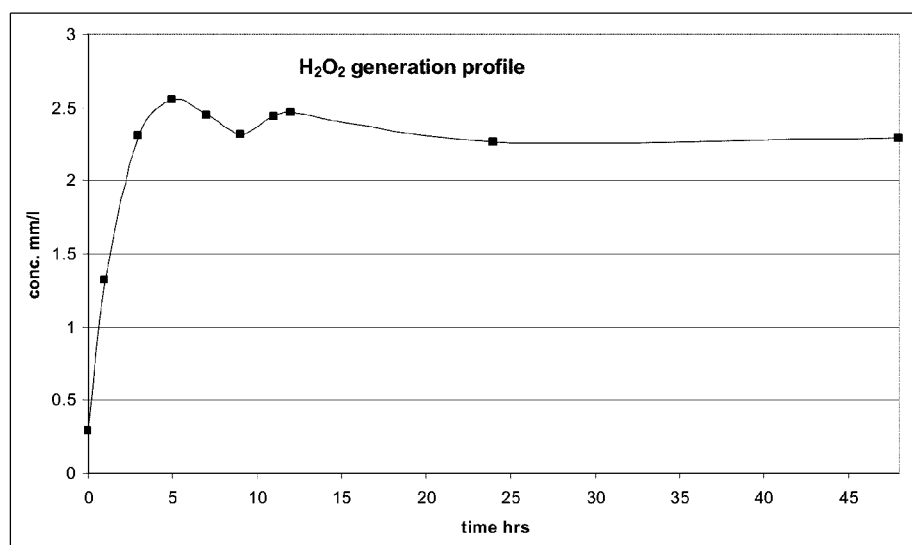

FIG. 5c shows this increased production of hydrogen peroxide ($A^3IS$ diluted 25% in DI water) is maintained for a period of at least 48 h.

Example 4.1

Figure 5D:
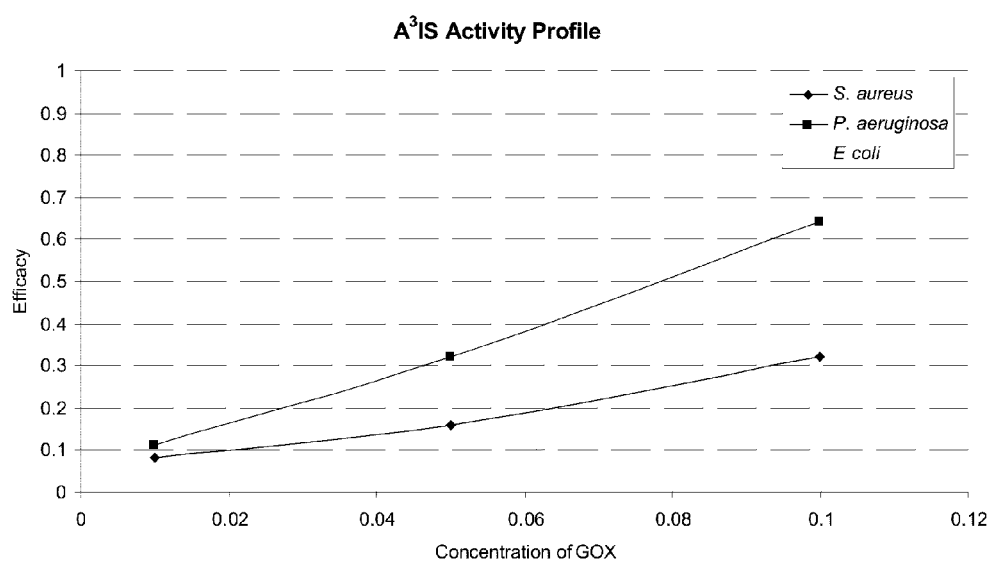

$A^3IS$—Antimicrobial Activity Increased with Increased Glucose Oxidase Concentration FIG. 5d shows a dose response relationship between the concentration range of glucose oxidase and antimicrobial effect on S. aureus, as measured using a spectrophotometric inhibition bioassay.

FIG. 5d further demonstrates that it is possible to address the issue of potency/efficacy, as the formulations produced may be adjusted by variations of the concentration of glucose oxidase which is incorporated during manufacture, results shown on *Staphylococcus aureus*, *Pseudomonas aeruginosa* and *Escherichia coli*.

Example 5

A³IS—Endogenous Hydrogen Peroxide Reservoir

When A³IS is mixed with water within the dilution range 50% to 0.1% the liberation of hydrogen peroxide is detected immediately. Table 6 shows that up to 75 mg/L hydrogen peroxide is detected at T=0. This is in contrast to Manuka honey which fails to register any liberation of peroxide at time zero (See Example 1 Table 2) and demonstrates the presence of a significant endogenous reservoir of hydrogen peroxide generated during the formulation process.

Also, after three hours of incubation of diluted samples the amount of peroxide detected in A³IS significantly exceeds that detected in the natural honey, Table 6.

TABLE 6

| % Dilution | 50.00 | 25.00 | 12.50 | 6.25 | 3.13 | 1.56 | 0.78 | 0.39 | 0.20 | 0.10 | 0.05 | 0.025 |
|---|---|---|---|---|---|---|---|---|---|---|---|---|
| Manuka | | | | | | | | | | | | |
| Normal pH | 3.89 | 4.35 | 4.96 | 5.95 | 6.60 | 6.87 | 7.03 | 7.11 | 7.12 | 7.14 | 7.15 | 7.15 |
| Normal pH Aw | 0.908 | 0.970 | 0.985 | 0.994 | 0.994 | 0.995 | 0.996 | 0.996 | 0.996 | 0.996 | 0.996 | 0.997 |
| % water | 53.0 | 74.7 | 84.5 | 91.3 | N/A | N/A | N/A | N/A | N/A | N/A | N/A | N/A |
| $H_2O_2$ mg/L (T = 0 hours) | 0 | 0 | 0 | 0 | 0 | 0 | | | | | | |
| $H_2O_2$ mg/L (T = 3 hours) | 0 | 35 | 35 | 65 | 55 | 40 | 40 | 35 | 30 | 0 | 0 | 0 |
| Adjusted pH | 6.6 | 6.6 | 6.88 | 7.02 | 7.10 | 7.13 | 7.18 | 7.20 | 7.20 | 7.21 | 7.21 | 7.21 |
| Adjusted pH Aw | 0.906 | 0.966 | 0.983 | 0.990 | N/A | N/A | N/A | N/A | N/A | N/A | N/A | N/A |
| A³IS | | | | | | | | | | | | |
| Normal pH | 5.5 | 6.0 | 6.96 | 7.05 | 7.13 | 7.17 | 7.17 | 7.19 | 7.2 | 7.21 | 7.21 | 7.19 |
| Normal pH Aw | 0.906 | 0.964 | 0.983 | 0.990 | 0.995 | 0.996 | 0.997 | 0.997 | 0.997 | 0.997 | 0.997 | 0.997 |
| % water | 52.4 | 71.8 | 83.9 | 90.7 | N/A | N/A | N/A | N/A | N/A | N/A | N/A | N/A |
| $H_2O_2$ mg/L (T = 0 hours) | 75.0 | 75.0 | 75.0 | 75.0 | 70.0 | 60.0 | 55 | 55 | 45 | 5 | 0 | 0 |
| $H_2O_2$ mg/L (T = 3 hours) | 90 | 90 | 75 | 80 | — | — | — | — | — | — | — | — |
| Adjusted pH | 3.8 | 5.6 | 6.55 | 6.9 | 7.03 | 7.12 | 7.17 | 7.19 | 7.20 | 7.21 | 7.21 | 7.21 |
| Adjusted pH Aw | 0.904 | 0.964 | 0.982 | 0.991 | N/A | N/A | N/A | N/A | N/A | N/A | N/A | N/A |

This endogenous reservoir, shown here ranging between 10 and 75 mg/l hydrogen peroxide depending on the quantity of GOX present in the A³IS, is shown in FIG. 5a, FIG. 5b and Table 6. Such a reservoir advantageously provides hydrogen peroxide, and its antimicrobial activity, for immediate effect upon application of A³IS. Combined with higher level of hydrogen peroxide produced upon dilution, this would be expected to contribute to a significantly increased antimicrobial effect compared with other systems such as Manuka honey.

Example 6

A³IS—Endogenous Hydrogen Peroxide Reservoir is Storage Stable

Figure 6:
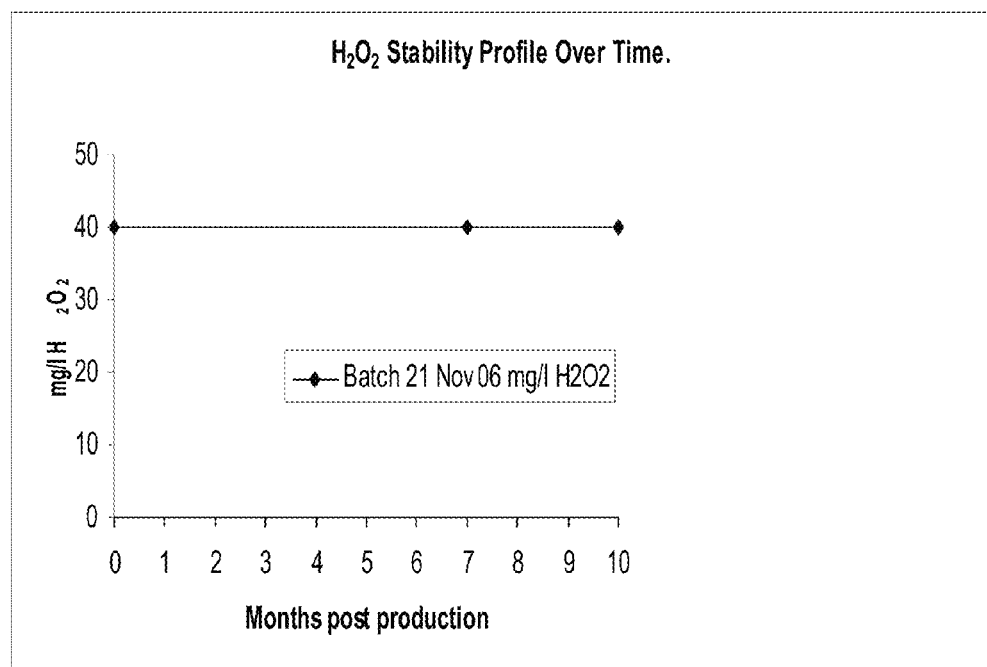

A surprising and advantageous feature of A³IS is the retention of both antimicrobial activity and the hydrogen reservoir over time as shown in FIG. 6.

Figure 7A:
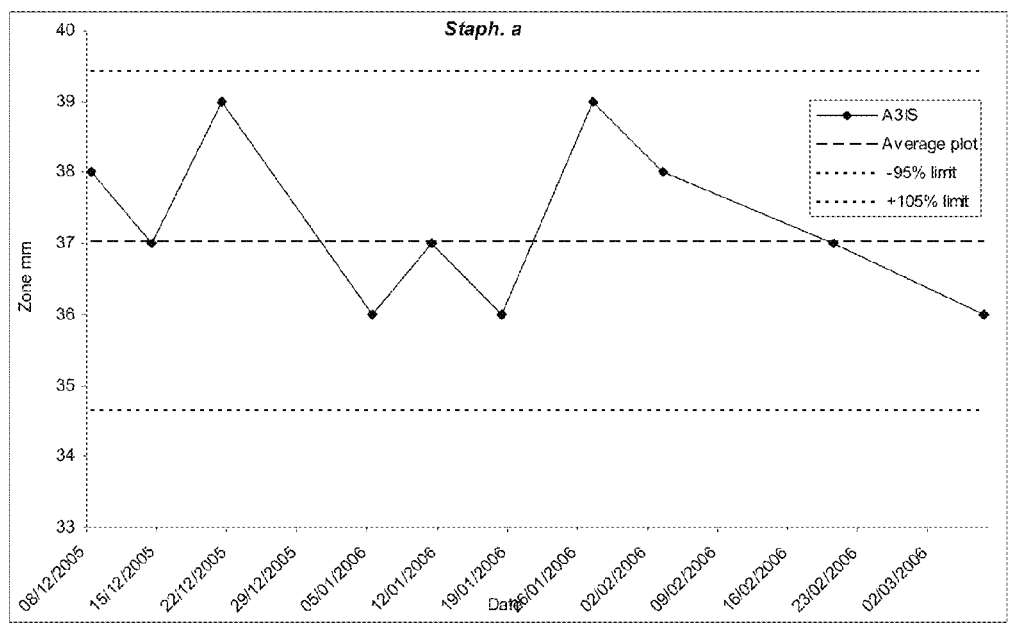
Figure 7B:
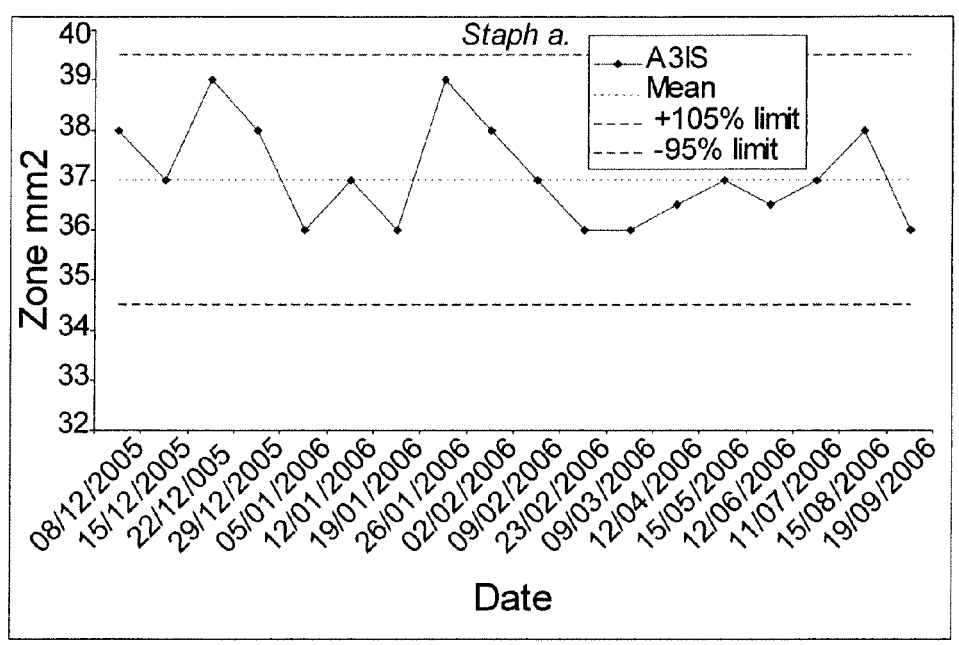

The available $H_2O_2$ reservoir produced by A³IS is storage stable as batches placed on stability retain the same levels of $H_2O_2$ as that detected when the batches are initially produced. Retention through stability of immediately available $H_2O_2$ is a unique feature of the A³IS formulations. Using the well diffusion assay to assess antimicrobial activity we demonstrate that a consistent level of antimicrobial activity is maintained over time. FIG. 7a shows the zones of inhibition measured at each sampling time point and the results graphed using 95% confidence limits during a period of three months. Similarly FIG. 7b shows extended stability of antimicrobial activity over a 9 month period. Extended stability data indicates that the A³IS formulation shows no loss of activity even after a period of 14 months.

Using the well diffusion assay to assess antimicrobial activity we demonstrate that a consistent level of antimicrobial activity over time. FIG. 7a shows the zones of inhibition measured at each sampling time point and the results graphed using 95% confidence limits during a period of three months. Similarly FIG. 7b shows extended stability of antimicrobial activity over a 9 month period. Extended stability data indicates that the A³IS formulation shows no loss of activity even after a period of 14 months.

Example 7

A³IS—Potent Antimicrobial Activity Against *Staphylococcus aureus*

Figure 8A:
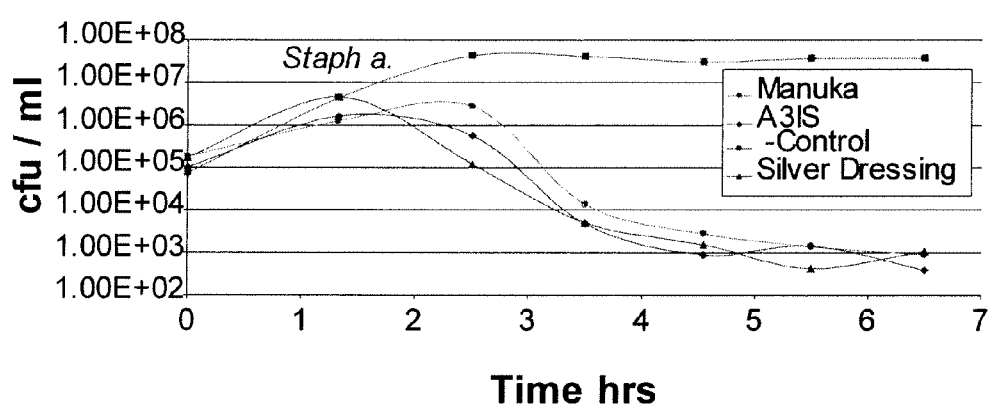
Figure 8B:
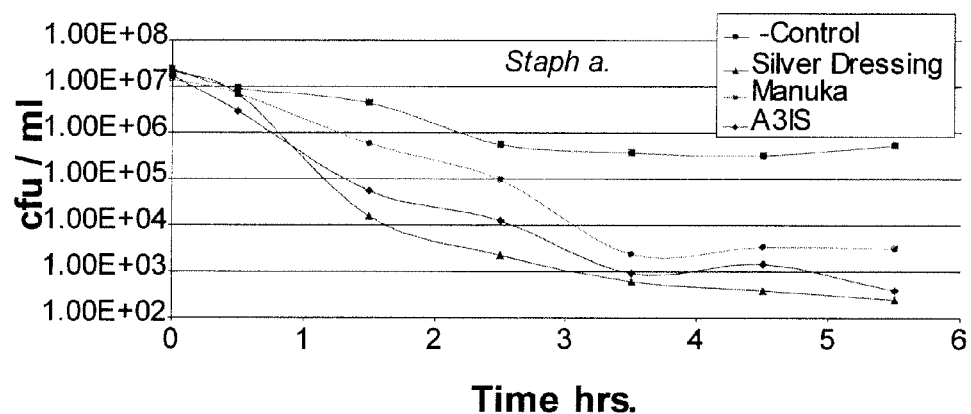

A³IS is shown to have antimicrobial activity against *Staphylococcus aureus*. FIG. 8a and FIG. 8b shows bacterial kill curves performed using two separate protocols, the NCCLS guidelines, method (FIG. 8a) and a Medical device manufacturer's specific protocol (FIG. 8b) over a 6.0 hour period. A³IS has increased efficacy compared with Manuka honey and comparable efficacy to silver dressing.

Figure 8C:
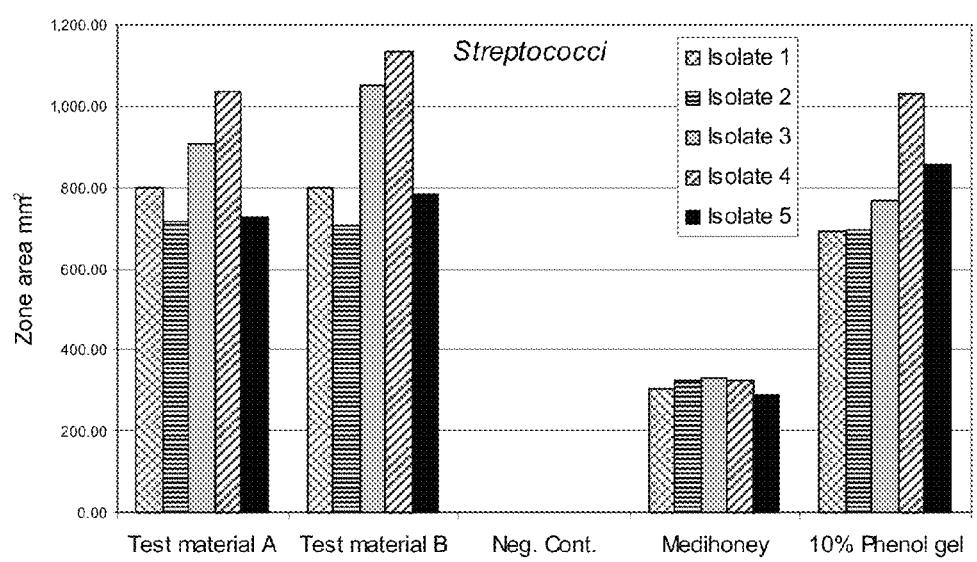

FIG. 8c shows the results of an inhibition assay (3 day repeats) for A³IS, Medihoney® and a 10% phenol gel when tested against 5 clinical isolates of the Beta haemolytic Streptococci Group A. A³IS is at normal pH 5.5 (test material A) and pH 7 (test material B), a negative control of A³IS containing no GOX is included. Formulation A³IS demonstrates comparable in vitro efficacy to a 10% phenol gel and is superior to Medihoney®.

Example 8

A³IS—Potent Antimicrobial Activity Against *Campylobacter*

Figure 8D:
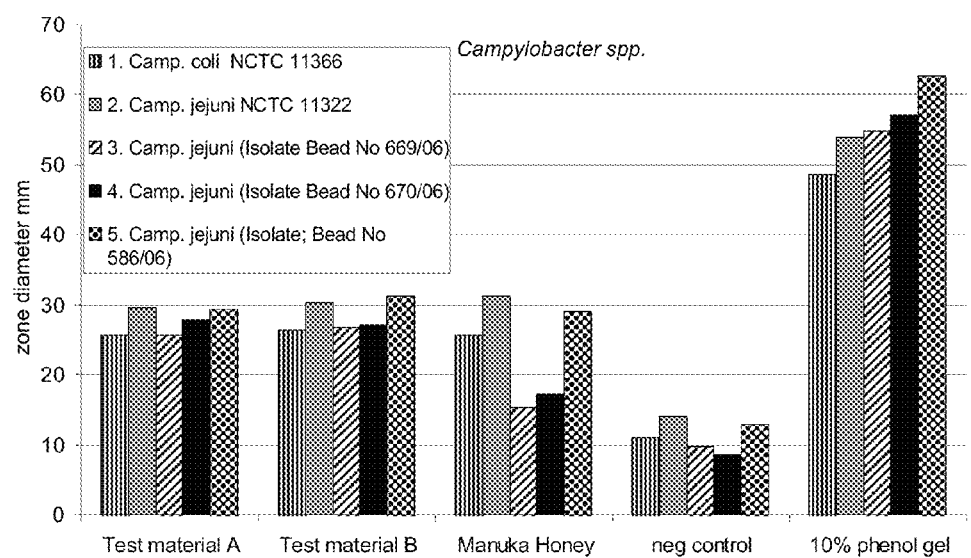

A³IS is shown to have antimicrobial activity against *Campylobacter*. FIG. 8d shows the results of an inhibition assay (3 day repeats) for formulation A³IS, Manuka honey and a 10% phenol gel when tested against 5 clinical isolates of the *Campylobacter* spp. Formulation A³IS is at normal pH 5.5 (test material A) and pH 7 (test material B), a negative control A³IS containing no GOX is included. Results indicate significant anti-*Campylobacter* in-vitro efficacy and the superiority of A³IS over Manuka honey.

Example 9

A³IS—Potent Antimicrobial Activity Against *Propionibacterium acnes*

A³IS is shown to have antimicrobial activity against *Propionibacterium acnes* (*P. acnes*).

Figure 9A:
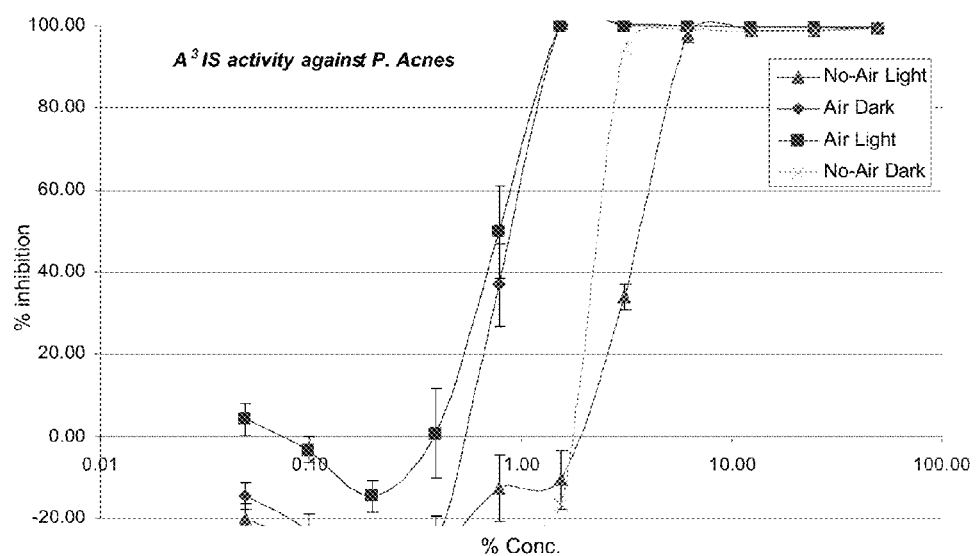
Figure 9B:
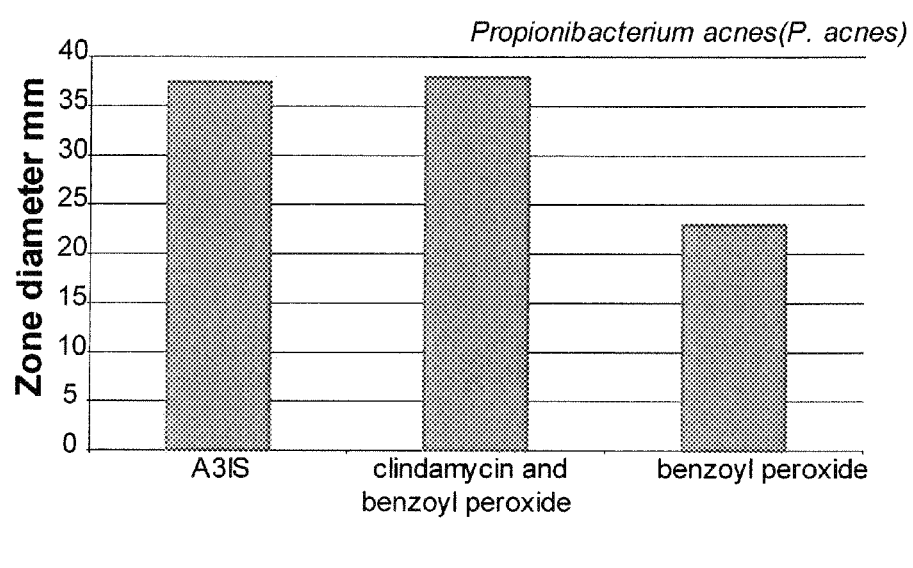

FIG. 9a. shows the inhibition results of A³IS against *P. acnes* under varying incubation conditions: light and dark aerobic, light and dark anaerobic. A³IS demonstrates a high level of activity against *P. acnes*, indicating the material may have potential for topical acne application. The results for A³IS and currently available anti-acne commercial products including some commercial products which incorporate antibiotics are shown in FIG. 9b. These results indicate that A³IS is comparable with 'respect to' in vitro anti-acne efficacy to commercially available anti-acne products containing Clindamycin and Benzoyl peroxide.

Example 10

A³IS—Potent Antimicrobial Activity Against MRSA

Figure 10:
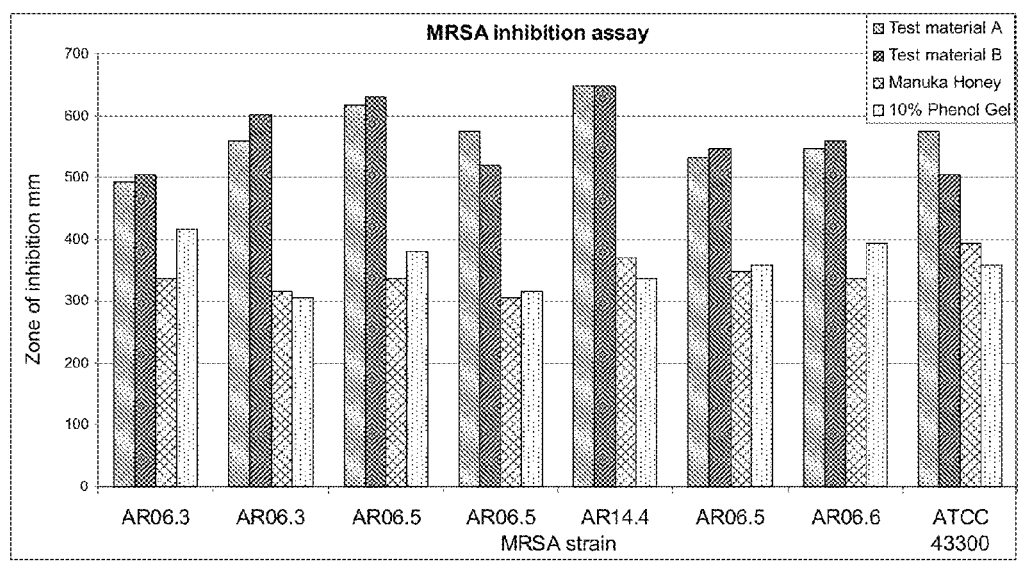
Figure 11A:
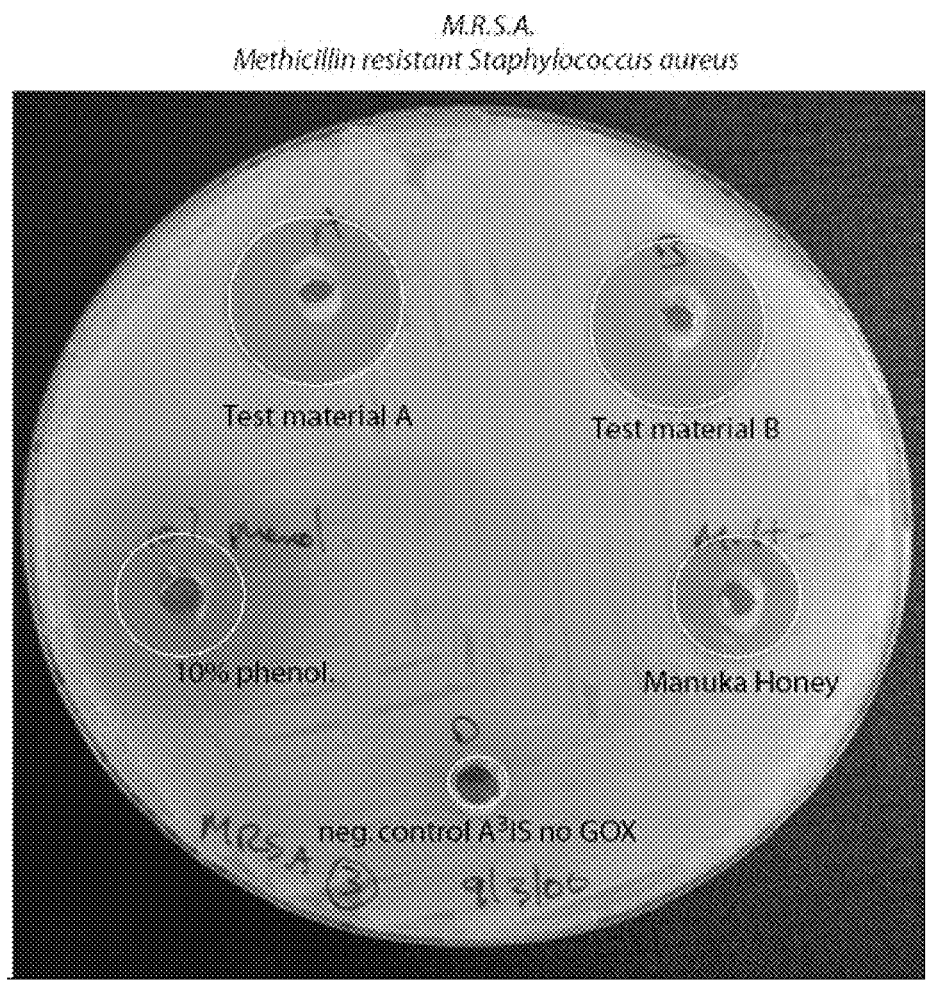

The Antimicrobial System formulation is shown to have antimicrobial activity against 8 strains of MRSA on three different days and compared to a 10% phenol standard and to Manuka honey FIG. 10. Formulation A³IS is at normal pH 5.5 (test material A) and pH 7 (test material B), a negative control A³IS containing no GOX is included. The results demonstrate significant in vitro anti-MRSA efficacy and the superiority of A³IS over Manuka honey and a 10% phenol gel control. Zones of inhibition are shown in FIG. 11a. Test material A is adjusted to pH 5.5 and test sample B is adjusted to pH 7. FIG. 11a shows the enhanced results of A³IS which is approximately 300% better than the Manuka honey. This clearly shows that the A³IS has superior and advantageous properties over and above Manuka honey.

Example 11

Figure 11B:
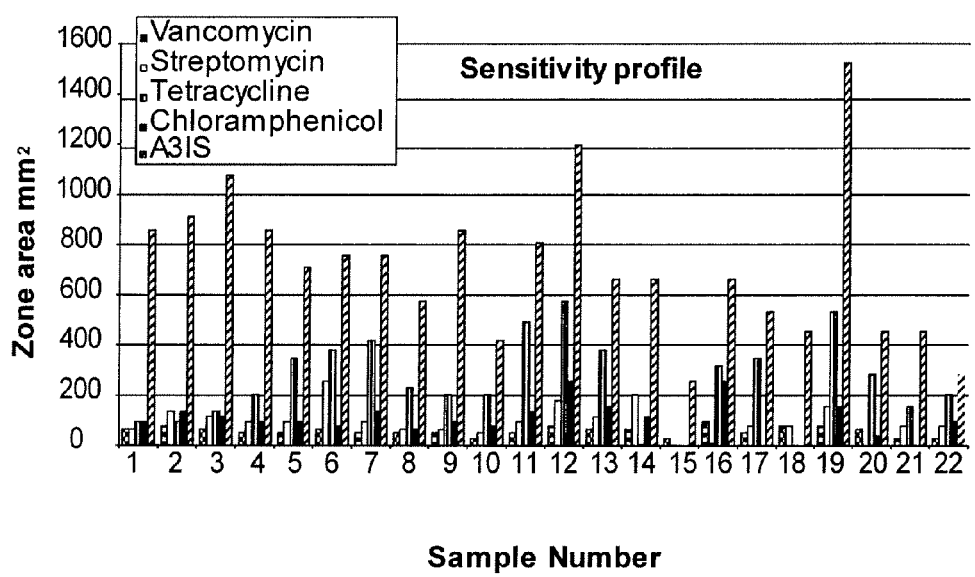

A³IS—Potent Antimicrobial Activity Against Clinical Isolates of Mastitis and Retention of Activity in Raw Milk FIG. 11b shows the results of an inhibition assay (3 day repeats) for A3IS and four antibiotics (Vancomycin, Streptomycin, Tetracycline and Chloramphenicol) when tested against 22 clinical isolates of Mastitis causing *Staphylococcus aureus* organisms. Formulation A³IS demonstrates superior in vitro efficacy to all of these antibiotics. Clinical isolate number 15 is resistant to Vancomycin, Streptomycin and Tetracycline and shows only mild sensitivity to Chloramphenicol, however, it demonstrates sensitivity to A3IS.

Figure 11C:
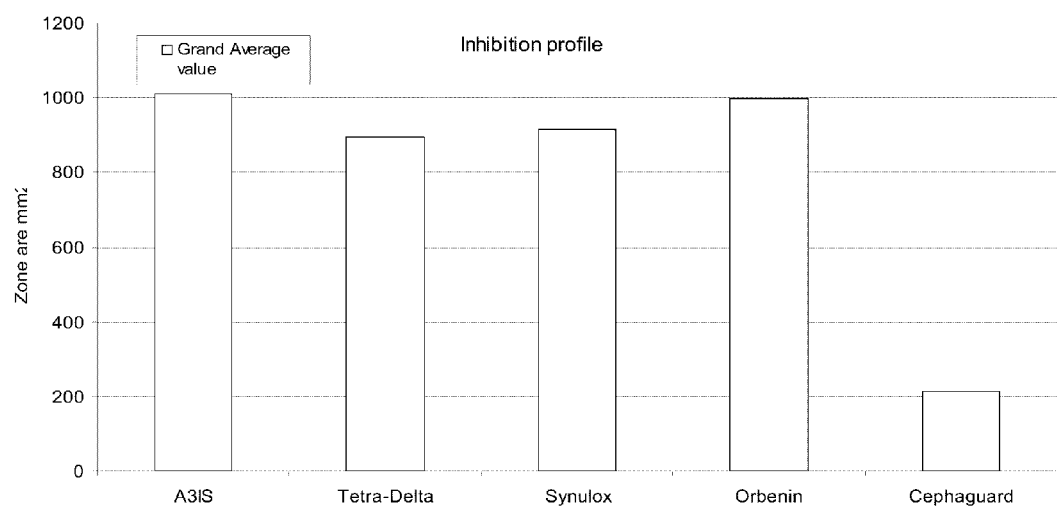

FIG. 11c shows the results of an inhibition assay (3 day repeats) for A³IS when tested against 22 clinical isolates of Mastitis causing *Staphylococcus aureus* organisms. Formulation A³IS demonstrates comparable in vitro efficacy to three of the leading commercially available multi antibiotic products for Mastitis and is superior to one of these products.

Figure 11D:
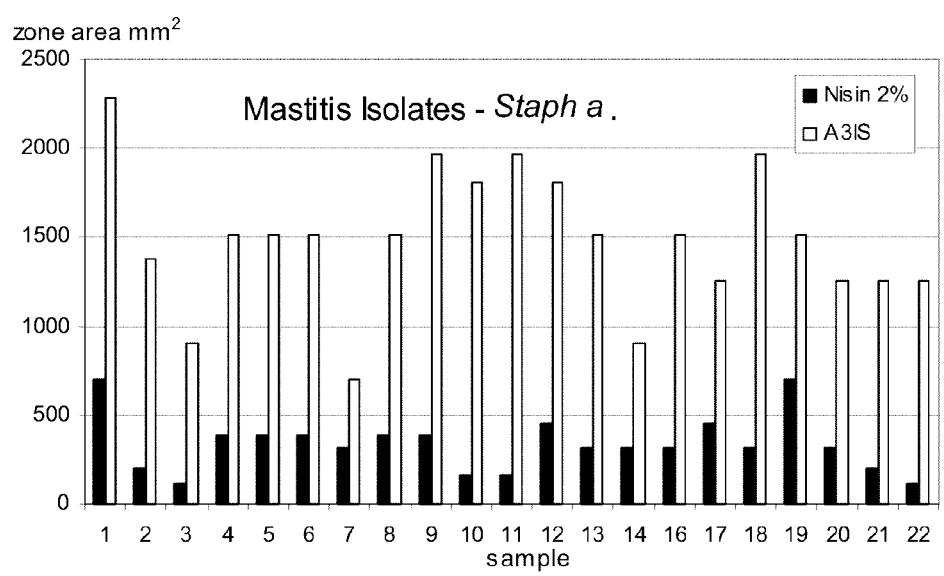

FIG. 11d shows the results of an inhibition assay (3 day repeats) for A³IS tested against a 2% Nisin solution on 21 clinical isolates of Mastitis causing *Staphylococcus aureus* organisms. Formulation A³IS demonstrates superior in vitro efficacy to the 2% Nisin solution. Note: Clinical isolate number 15 of FIG. 11b was unrecoverable from storage and is not included in this assay.

Figure 11E:
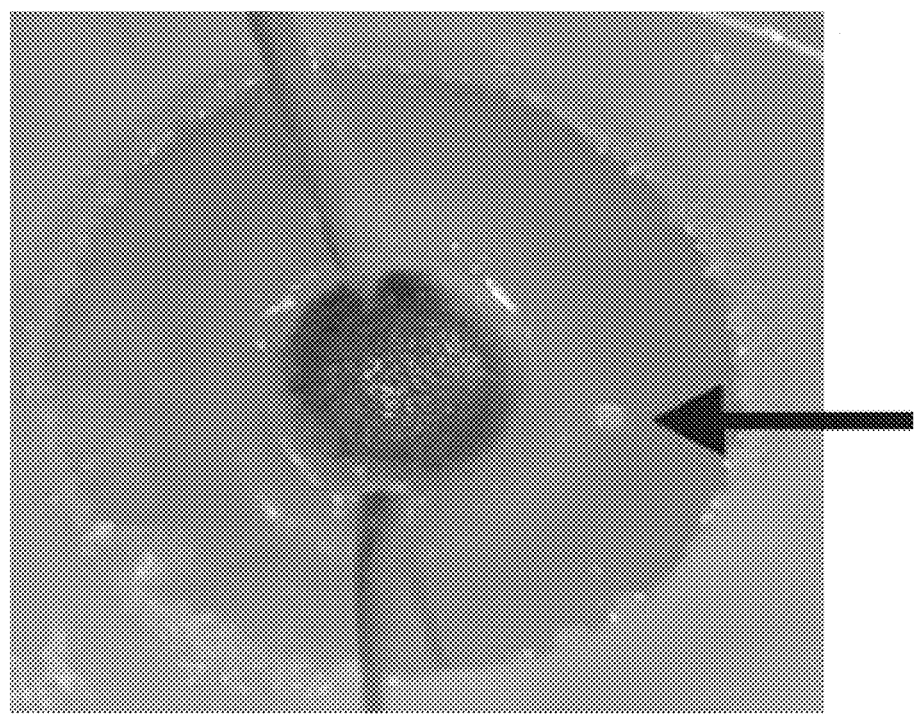
Figure 12A:
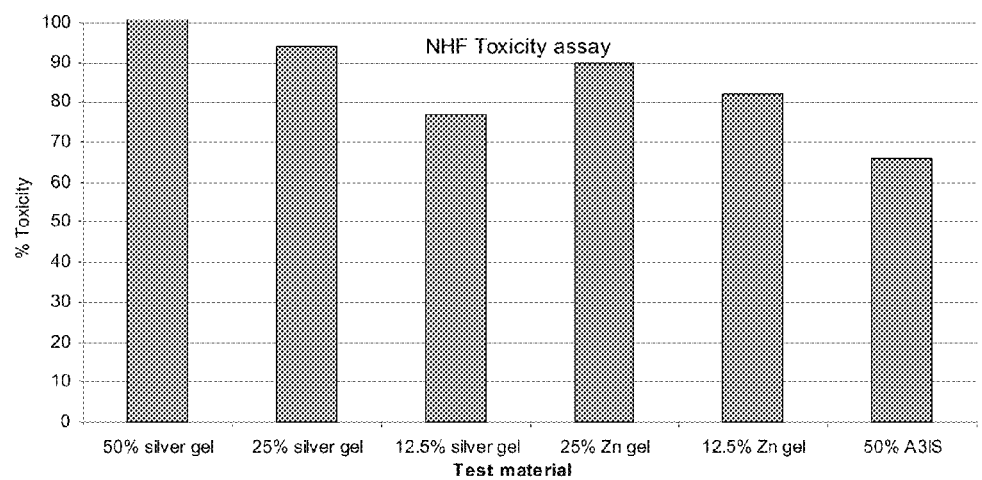
FIG. 12d shows A³IS and other test material MTT irritancy assay over a 24 hour period employing the Skinethic® 3D skin model. A³IS demonstrates less irritancy in this three dimensional assay than the commercially available products tested.
FIG. 12e shows Haematoxylin/Eosin (H&E) stained cross section of Skinethic® 3D skin exposed to the comparative silver containing gel product. Note that the silver formulation causes detachment of the epidermal layer from the basal layer.
FIG. 12f shows Haematoxylin/Eosin (H&E) stained cross section of Skinethic® 3D skin exposed to the comparative silver containing gel product. Note that the silver formulation causes detachment of the epidermal layer from the basal layer.
FIG. 12g shows Haematoxylin/Eosin (H&E) stained cross section of Skinethic® 3D skin exposed to A³IS. Note that A³IS does not cause detachment of the epidermal layer from the basal layer.
FIG. 12h shows Haematoxylin/Eosin (H&E) stained cross section of Skinethic® 3D skin exposed to A³IS. Note that A³IS does not cause detachment of the epidermal layer from the basal layer.
Figure 12B:
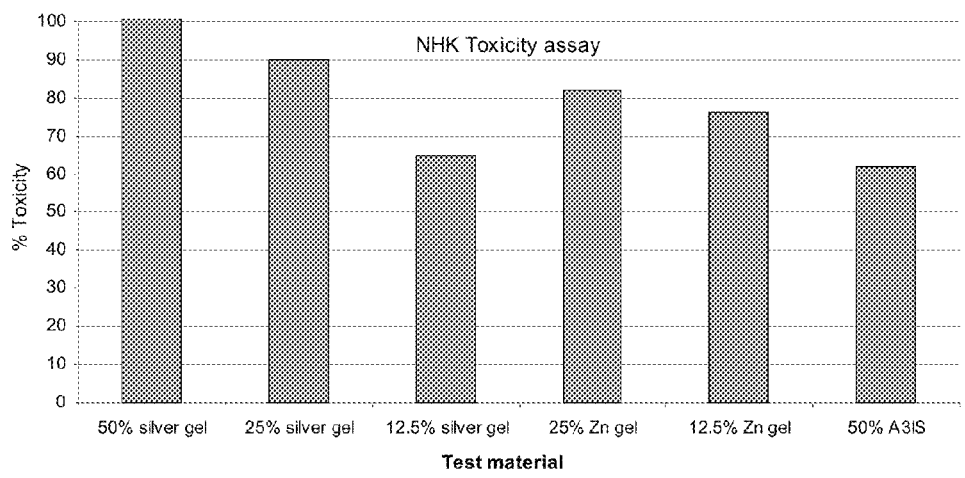
Figure 12C:
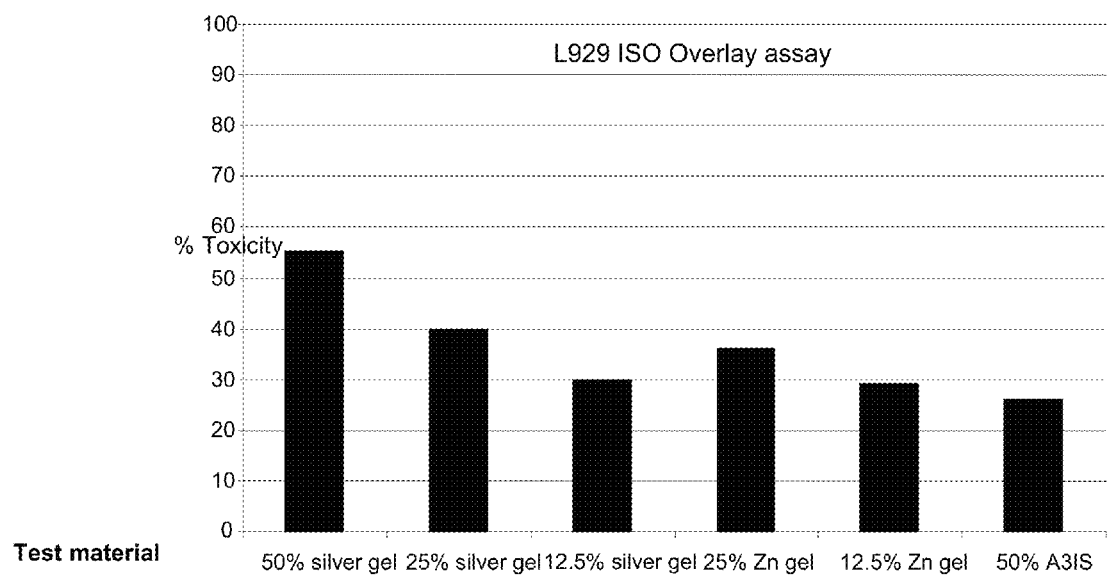
Figure 12D:
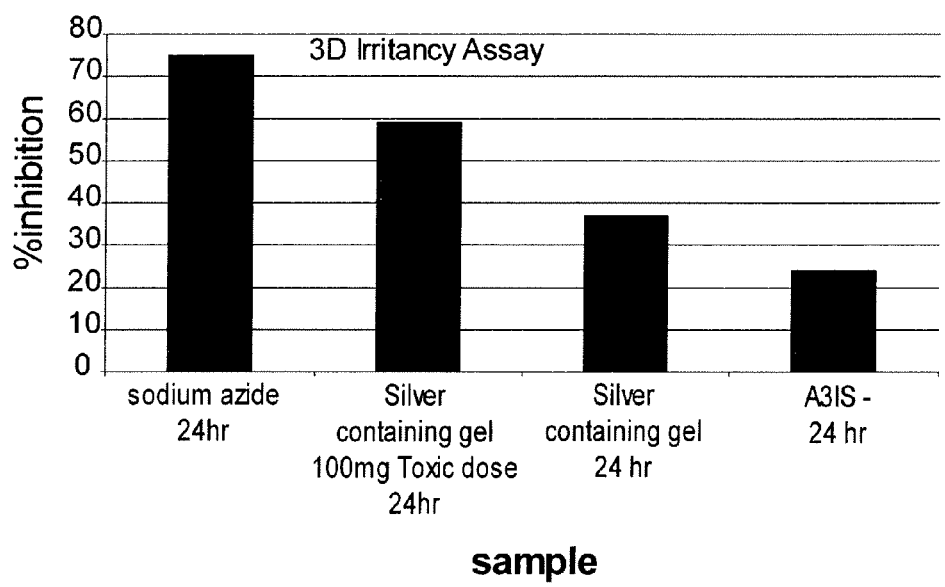
Figure 12E:
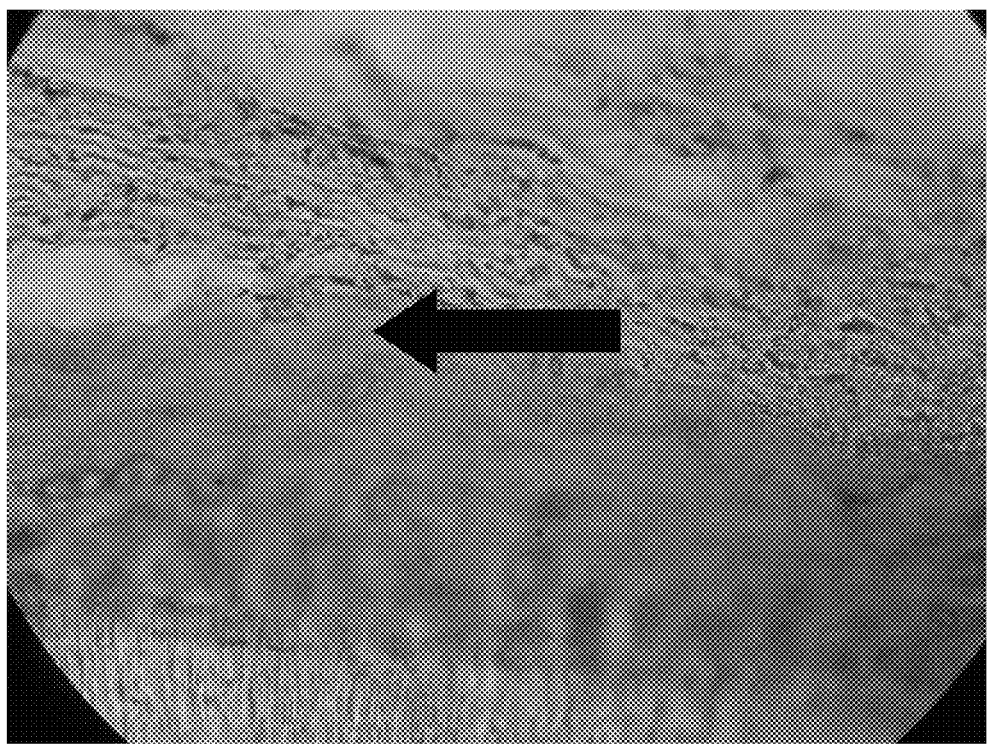
Figure 12F:
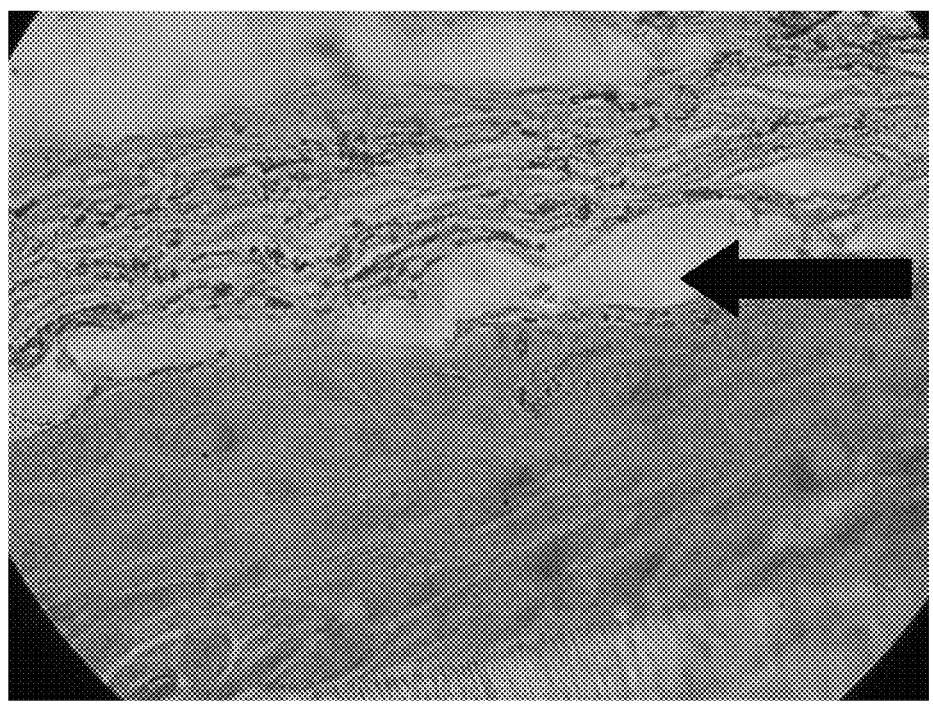
Figure 12G:
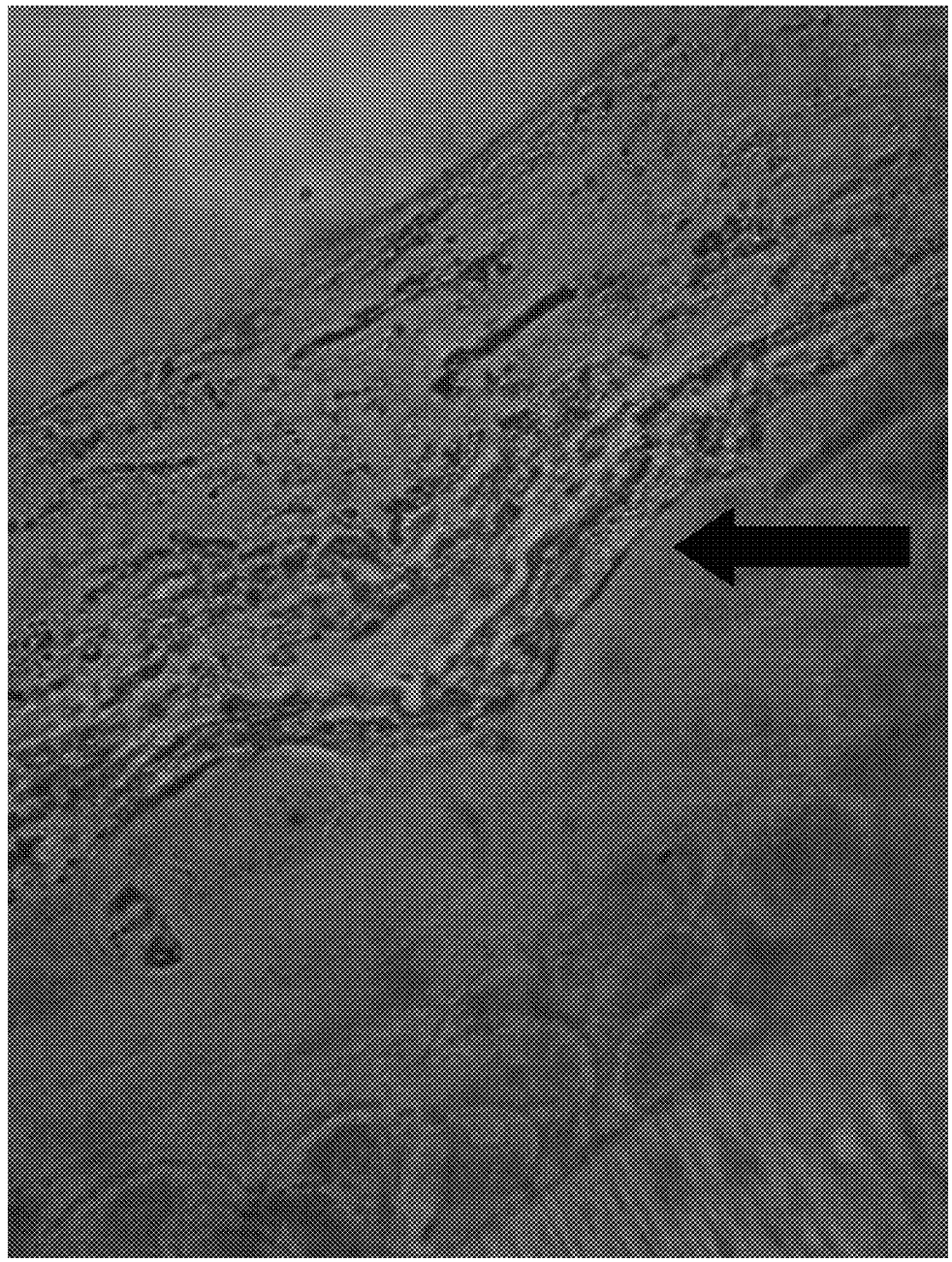
Figure 12H:
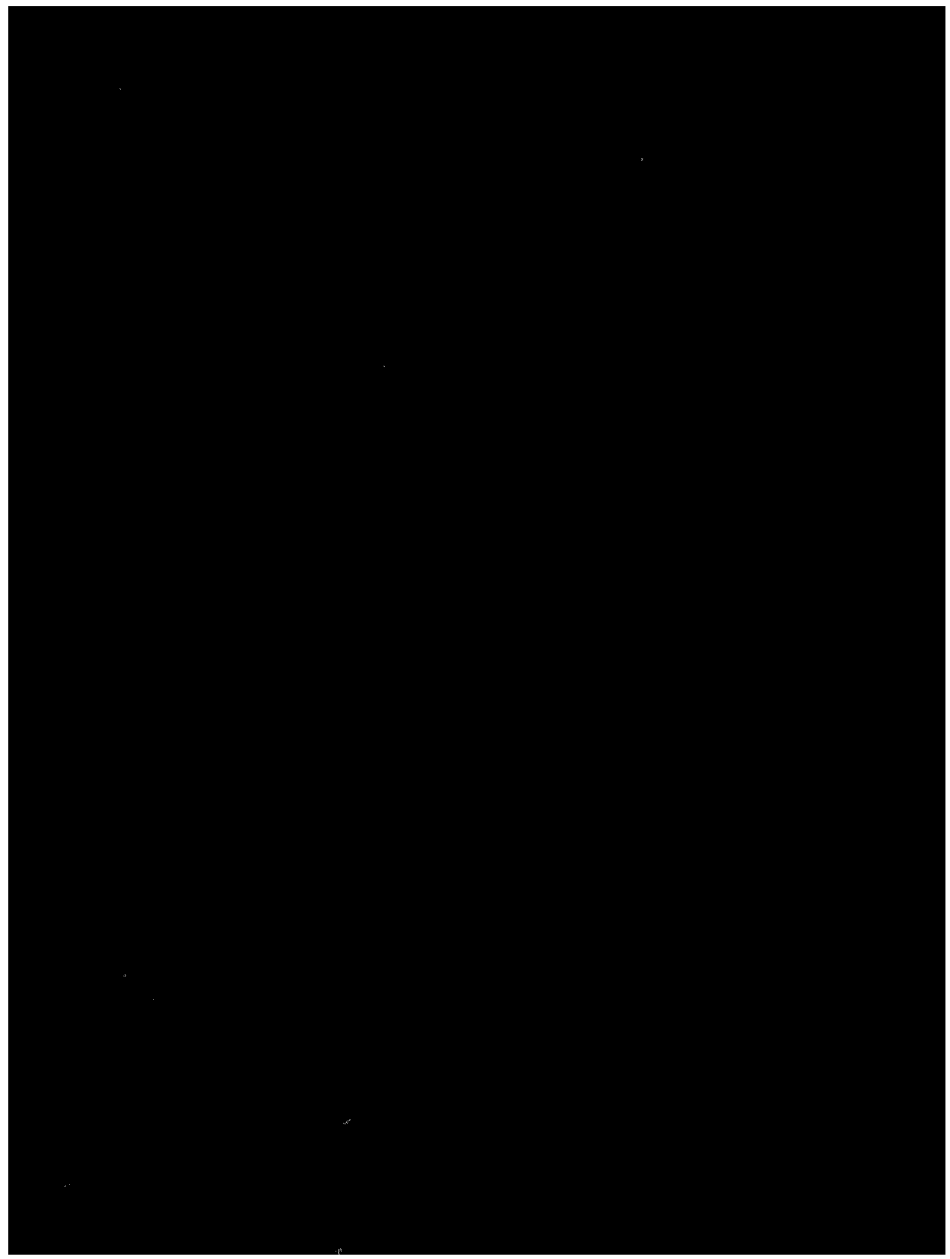

FIG. 11e shows the presence of a 2% Nisin resistant colony within the zone of inhibition during a Nisin efficacy study. A³IS resistant colonies have never been observed in efficacy studies based on zone of inhibition assays, nor has regrowth of cultures occurred following spectrophotometric based A³IS inhibition assays.

Five mls of raw milk is inoculated with 0.1 mls of an overnight culture of *Staphylococcus aureus* (containing approximately $5 \times 10^7$ cfu/ml) followed by the addition of 0.5 mls of A³IS formulation. This mixture is incubated overnight at 37° C. The mixture is then analysed for $H_2O_2$ production and survival of the inoculated *Staphylococcus aureus*. Levels of $H_2O_2$ in excess of 100 mg/l are detected in this milk and few of the inoculated *Staphylococcus* are recovered. The mixture shows no sign of souring which would be expected following overnight incubation at this temperature. By contrast, raw milk to which the A³IS is not added sours and coagulates. This finding indicates A³IS retains activity even in a complex medium such as raw milk

Example 12

A³IS—In-vitro Toxicity/Irritancy Measurement

Toxicity/irritancy is determined using normal human fibroblasts (NHFs ECACC 90011807) and normal human keratinocytes (NHKs CC-2501) grown in Eagles Minimum Essential Medium (EMEM) with, 2 mM L-Glutamine, 10% Foetal Bovine Serum (FBS), incubated at 37° C. in 5% CO2. Three repeats of two dimensional assays using 24 and 12 well plates, utilising both neutral red and 3-(4,5-Dimethyl-thiazol-2-yl)-2,5-diphenyltetrazolium bromide (MTT), Sigma,. 'In Vitro Toxicology Assay Kit' for direct contact cell assays are performed, to assess viability after incubation with test materials for 8 hrs (sodium azide—positive control, concentrations of silver gel, zinc gel, A3IS and fresh media—negative control).

ISO 10993, agar overlay tests for cytotoxicity: in vitro method is also used, employing L929 cells (mouse fibroblasts ECACC 85011425). In brief; a confluent monolayer of cells is incubated, this is then covered with a layer fresh medium (EMEM, 2 mM L-Glutamine, 5% FBS, 2% Penicillin-Streptomycin) containing 1.5 g/l of soft agar and allowed to solidify. One tenth of the surface is covered with test materials (previously described) and incubated for 24 hrs. Post incubation the test material is carefully removed and a vital stain (neutral red) in fresh media added. After incubation this is removed, the cells washed and then the dye extracted from the cells and quantified spectrophotometrically for cell viability.

A three dimensional dermal skin model (Skinethic, France) is also employed to determine the irritant effect of the formulation and controls on differentiated keratinocytes as in the stratum corneum, a cultured skin equivalent. The assay employs a three dimensional epidermal skin model and is carried out at several time points. The reconstituted human epidermis model consists of an airlifted, living, multi-layered epidermal tissue construct, produced in polycarbonate inserts in serum-free and chemically defined medium, featuring normal ultra-structure and functionality equivalent to human epidermis in vivo. Quadruplicate in vitro reconstituted human epidermis tissues, age day 17, (size 0.63 cm$^2$) are dosed topically with 2-10 mg/cm$^2$ of the formulation for 3 and 24 hours and tissue viability assessed using MTT assay, using the German Federal Institute for Risk Assessment (BFR-ZEBET) validated protocol.

Cell culture supernatant from the irritancy assay described previously is analysed using an IL-1 Enzyme-Linked Immuno Sorbent Assay (ELISA) (R&D Systems) and a Lactate Dehydrogenase (LDH) ELISA (R&D Systems), for cytokine and enzyme measurement to assess immunostimulatory and irritant effect of test materials.

Cross sections of the 3D skin models used for the irritancy assay are stained with haematoxylin and eosin (H&E), The Technical Procedure Included:

Fixation: The tissues are mechanically and biochemically stabilised in a fixative. The fixative is neutral buffered formalin, 10% formaldehyde in phosphate buffered saline (PBS).

Embedding: The technique used is wax embedding. The samples are progressively immersed in increasing concentrations (20%, 30%, 40%, 50%, 80% and 100%) of pure ethanol to dehydrate the tissue, followed by a clearing agent, xylene (100%), and finally hot molten paraffin wax (impregnation) and allowed to cool and harden.

Sectioning: The sample tissue is then sectioned into 5 micrometer sections using a microtome. These slices are then placed on a glass slide for staining.

Staining: To view the tissue under a microscope, the sections are stained with hematoxylin and eosin (H&E) to asses the rate of surface epidermal degradation caused by each test material.

FIG. 12$a$ and FIG. 12$b$ show the results of the initial toxicity assessment of A$^3$IS by means of the MTT viability assays on NHFs (Normal Human Fibroblasts) and NHKs (Normal Human Keratinocytes). Percent toxicity was calculated according to the formula: % Toxicity=1−(OD average of test material wells/average OD of corresponding control wells (no test material added))×100. Included in the assay are a 50% concentration of A3IS, a range of concentrations of a commercial silver containing gel and a commercial zinc containing gel product, compared to sodium azide (positive control). For the toxicity assay the concentration of test material used was twice that used for the irritancy assay, a 100 mg per well and the contact time was extended to 8 hrs.

FIG. 12$c$ shows the results of the ISO International Standard, 10993-5 agar overlay assay for cytotoxicity over 24 hrs using neutral red on L929s. Percent toxicity was calculated according to the formula: % Toxicity=1−(OD average of test material wells/average OD of corresponding control wells (sodium azide added))×100. Included in the assay are a 50% concentration of A$^3$IS, a range of concentrations of commercial silver containing gel and commercial zinc containing gel product, compared to sodium azide (positive control). The sodium azide positive control gives 100% toxicity. For the agar overlay toxicity assay the amount of test materials used was similar to that used for the initial direct contact assays of 100 mg per well however the contact time was extended to 24 hrs.

The results of an irritancy assay of the test materials for a range of contact times employing Skinethic® 3D skin model are shown in FIG. 12$d$. This reconstituted human epidermis model consists of an airlifted, living, multi-layered epidermal tissue construct, produced in polycarbonate inserts in serum-free and chemically defined medium, featuring normal ultra-structure and functionality equivalent to human epidermis in vivo. The effects of this direct contact on the 3D skin samples are shown on Haematoxylin/Eosin (H&E) stained cross sections in FIG. 12$e$ and FIG. 12$f$ for the comparative silver containing gel product. FIG. 12$g$ and FIG. 12$h$ show H&E stained cross sections following A$^3$IS formulation direct contact on the 3D skin samples. The results show that the silver formulation causes detachment of the epidermal layer from the basal layer, whereas the sample A$^3$IS formulation exhibits no damage.

Quadruplicate in vitro reconstituted human epidermis tissues, age day 17, (size 0.63 cm$^2$) were dosed topically with 2-10 mg/cm$^2$ of the formulation for 3 and 24 hours and tissue viability assessed using MTT assay, using the German Federal Institute for Risk Assessment (BFR-ZEBET) validated protocol. Percent irritancy was calculated according to the formula: % Irritancy=1−(OD average of test material skins/average OD of corresponding control skins (no test material added))×100. A$^3$IS demonstrates less irritancy in this three dimensional assay than the commercially available products tested.

Example 13

A$^3$IS—Induction of Inflammatory IL-1 Release from Skin Cells

FIG. 13$a$ shows the results of an ELISA assay of the supernatant removed during the 3D irritancy assay over a 48 hour period, measuring and comparing the release of IL-1 when exposed to A$^3$IS formulation, to a sodium azide positive control, and a commercial silver containing gel product. The results indicate that IL-1 is released from the skin cells exposed to the A$^3$IS formulation. FIG. 13$b$ Illustrates the measurement of released Lactate Dehydrogenase (LDH) in the cell media used during the irritancy test protocol. Results show LDH release by cells following exposure to the A$^3$IS formulation, a sodium azide positive control, and a commercially available silver containing gel product. Lactate dehydrogenase is released by cells exposed to destructive compounds. The results indicate that the A$^3$IS formulation is less toxic than commercially available silver containing gel products.

Example 14

A$^3$IS—Terminal Sterilisation

A$^3$IS was filled into glass bottles and plastic tubes. These were then sterilised by Gamma irradiation. Post sterilisation, the samples antibacterial activity was compared to pre sterilisation results. It was found that Gamma irradiation did not reduce activity. There was slight discolouration of the primary container; however the irradiation process did not affect the activity or the colour of the test material FIG. 14 shows the efficacy of A$^3$IS prior to and after gamma irradiation on *S. aureus, E. coli* and *Pseudomonas aeruginosa*.

Example 15

A³IS—Incorporation in a Collagen-GAG (Glycosaminoglycan) Matrix—as an Antibacterial Dressing Picture of A³IS in GAG on *S. aureus* and pictures of the infiltration of GAG (FIG. 15a to FIG. 15c).

Collagen-GAG (glycosaminoglycan) matrix as has been previously described (Wilkins, L., M., et al, 1993. Development of a bilayered Living Skin Construct for Clinical Applications. Organogenesis Inc.) is formulated and A3IS was added to this matrix at a ratio of 1:1.

The mixture is poured onto a sterile surface to form a thin layer of approx 1 mm and dried in an incubator for 24 hrs to form a skin dressing. Once dry, 1 cm sections are cut, and placed onto inoculated agar plates inoculated with *S. aureus*, *E. coli* and *P. acnes*. Antibacterial activity against *S. aureus*, *E. coli* and *P. acnes* is observed. There are clear defined zones of inhibition and no bacterial growth is observed under the dressing.

The test sections are also placed onto a confluent monolayer of NHFs (normal human fibroblasts) in 6 well plates at time $T_0$. It is found that there was little to no toxicity.

The test sections were also co-incubated with NHF cells, in cell culture wells. It was found that in addition to adhering to the bottom of the cell culture wells, as was expected, the NHF cells also infiltrated, attached to and grew on the test sections. This demonstrates that Collagen-GAG matrices incorporating A³IS are suitable matrices for cell attachment and growth (see FIG. 15b and FIG. 15c).

Example 16

A³IS—Incorporation in an Alcoholic Gel

A³IS is mixed with an alcoholic gel consisting of absolute alcohol, ultrez 10 gelling agent, di-isopropanolamine and propylene glycol, which is mixed prior to the addition of A³IS resulting in a clear non-adhesive material. This gel formulation is tested using the well diffusion and surface diffusion bio assay to determine zones of inhibition against *S. aureus, E. coli* and *P. acnes*. Results are shown for *S. aureus* FIG. 16a. It should be noted that the zones of inhibition are artificially low in this situation due to the absorptive property of the gel matrix, thus not allowing free diffusion through the agar matrix but there is a clear zone around the gel matrix.

The gel formulation is put on a short term stability study of 6 weeks, including a freeze thaw test. Results indicated that the gel formulation maintained stability throughout the test period FIG. 16b. Results are shown for *S. aureus*.

Example 17

A³IS—Incorporation onto Commercially Available Wound Dressings

Picture of A³IS in wound dressings FIG. 17

Formulation A³IS was poured onto the surface of a range of commercially available dressings Kaltostat® (Comvita), Kendal® (Telfa) and a Collagen-GAG (glycosaminoglycan) matrix as previously described and allowed to diffuse into the dressing for several hours to form a thin layer of approximately 1 mm. 1 cm2 sections were cut and placed onto agar plates, previously inoculated with *S. aureus, E. coli* and *P. aeruginosa*. The antibacterial efficacy of A³IS impregnated dressings was then compared to Aquacel® (Convatec) and Betadine® (Seton) commercially available dressings that contain elemental silver and iodine FIG. 17. It was found that the A³IS dressings are as effective antimicrobially as Aquacel® (Convatec) and Betadine® (Seton) and a commercially available dressing that use elemental silver and iodine.

Example 18

A³IS—Potent Antimicrobial Activity against Onychomycosis

A case study on the efficacy of A³IS in the treatment of fungal nail infections was carried out on a human volunteer. The infected nail was the big toe nail on the right foot and the infection was localised on the left side of the nail. The infection had been present for a considerable period of time, approximately 2 years. Prior to treatment, a photograph of the infected nail was obtained FIG. 18a. The treatment was carried out once daily in the morning, subsequent to the subject having a shower and toweling dry. A³IS was applied to the surface of the nail over the infected region rather than over the entire nail surface. A³IS was then covered with a bandage whose wadding had been moistened using water and the nail was therefore covered in an occlusive dressing for the rest of the day FIG. 18b. This treatment was carried out daily for a period of three weeks. After a period of two days, another photograph was taken FIG. 18c. It is evident that the infected region of the nail has changed appearance in that it is now darker in colour. During the period of treatment, there was little evidence of further physical alteration except the development of an increasingly larger section of un-infected nail growing out. A further photograph 8 weeks after initiation of the treatment is shown FIG. 18d. In this the band of uninfected nail is clearly visible, indicating that the dermatophytes have been eliminated.

Example 19

Testing the Ability of A³IS Against *T. Rubrum*

Materials and Methods

Anti-fungal A³IS formulations were made in accordance with Table 6

TABLE 6

| Ingredient | Percentage by weight |
| --- | --- |
| Purified water | 13.5 adjusted to make 100% |
| Fructose Powder | 35% |
| Glucose Powder | 38% |
| Maltose Powder | 10% |
| Sucrose Powder | 1.5% |
| Glucose Oxidase Powder | 0.5% enzyme (260 U/mg) pre-dissolved in 1.5% of purified water |
| TOTAL | 100% |

Two test tubes were filled with sabaroud dextrose broth which supports the growth of *T. Rubrum*. The test tubes were inoculated with samples of the actively growing *T. Rubrum* and aged (1 week old) *T. Rubrum*. A³IS was added to one of the test tubes and the other (without A³IS) was used as a control. Both test tubes were placed in an incubator and grown on for a period of two days at 35° C. after which time the photograph of FIG. 19 was taken. The tubes were re-examined after a period of 1 and 2 weeks.

Results and Conclusions

The test tube on the left of FIG. 19 is the control and it is evident that there is significant growth of the organism as indicated by the clearly visible turbidity. The solution is not turbid in the test tube on the right of FIG. 19, thus, no *T. Rubrum* growth is evident.

Thus, after 1 to 2 weeks we found no change in the test tube containing $A^3IS$ and *T. Rubrum*, demonstrating that $A^3IS$ has a significant antifungal effect.

In front of both test tubes are hydrogen peroxide dip sticks and it is evident that there is a significant level of peroxide in the $A^3IS$ whereas there is no evidence of hydrogen peroxide in the control.

In order to determine whether $A^3IS$ kills *T. Rubrum*, samples of the 2 the week old broth where organisms did not exhibit growth were taken. A sample of the broth in which the *T. Rubrum* had been growing, or not growing in the $A^3IS$ treated sample, were then streaked onto the surface of SDA agar in a petri dish. We found no evidence of growth of *T. Rubrum*, no viable *T. Rubrum* cells in the $A^3IS$ treated sample. On this basis, we conclude that $A^3IS$ kills *T. Rubrum*. Thus, we have demonstrated that $A^3IS$ has both fungicidal and sporicidal activity.

Example 20

Zone of Inhibition Assay

A zone of inhibition assay in a petri dish and a TurChub® cell without a nail barrier was carried out against the selected test organism (*T. rubrum*) using $A^3IS$. These investigations were carried out to ensure activity of the tested formulation against the test organism, compatibility of the formulation with the agar and to confirm zones of inhibition were obtainable with prior $A^3IS$ to investigating its nail permeation and efficacy.

Method
  Preparation of Sabouraud Dextrose Agar (Control)
  65 g of powdered Sabouraud dextrose agar was added to 1 L de-ionised water. The mixture was boiled until the agar visibly dissolved. It was then sterilised at 121° C. for 15 minutes in an autoclave. After removing the molten agar from the autoclave it was allowed to cool to 56° C., before transferring 500 ml into a sterile 245 mm Petri dish and 25 ml into sterile 90 mm Petri dishes. The Petri dish was left with the lid slightly ajar (ca. 1 cm opening) for 30 minutes under a laminar flow cabinet before use.
  Preparation of a Suspension of *T. Rubrum*
(i) A 90 mm Sabouraud dextrose agar plate was seeded with *Trichophyton rubrum* by gently removing mycelium and spores using a sterile swab from a slope culture and transferring them onto the surface of the agar.
(ii) The agar plate was then incubated at 25° C. for 7 days.
(iii) The white spores were then washed from the surface of the plate with Ringers solution (20 ml).
(iv) The spore suspension was then filtered through a sterile gauze (Smith+Nephew, Propax, 7.5 cm×7.5 cm 8 ply gauze swab, BP Type 13) to remove mycelium and agar debris.
(v) A viable count of the spore suspension was performed and the spore count adjusted to approximately $1 \times 10^7$ cfu/ml, by diluting or concentrating the spores accordingly in a final volume of 20 ml.
Zone of Inhibition Assay
1 ml of the *T. rubrum* suspension prepared was pipetted onto the surface of a pre-poured 245 mm Sabouraud dextrose agar (SDA) plates and the suspension spread evenly over the surface of the agar with a sterile spreader. The agar plates was then left to dry under a laminar flow cabinet.

The zone of inhibition assay was carried out by applying 20 μl of all the test items separately to the surface of a ¼ antibiotic assay disc (n=2 for each, note; the disc did not contain any antibiotics) and allowed to air dry for a period of 10 min under the laminar flow cabinet (4 discs in total). The disc was then inverted and placed onto the surface of all of the plates pre-seeded with *T. rubrum* and incubated at 25±2° C. for seven days. Following incubation the zone of inhibition for the test items was measured with calipers.
Results The results are shown in FIG. 21. FIG. 21 depicts Disc diffusion Zone of Inhibition assay on SDA against *T. rubrum* with $A^3IS$ active and $A^3IS$ Placebo in accordance with Example 20. The zones of inhibition surrounding $A^3IS$ active are clearly visible in FIG. 21, again demonstrating the antifungal effect of $A^3IS$.

Example 21

A Study of the Efficacy of $A^3IS$ Active and $A^3IS$ Placebo

Materials
Test item 1: $A^3IS$ Active made in accordance with Table 6.
Test item 2: $A^3IS$ Placebo comprises the same combination of the sugars used in $A^3IS$ (Fructose, D-Glucose, Maltose, Sucrose, de-ionised water) without the addition of the enzyme glucose oxidase. The sugars and water are heated to dissolve and then cooled to room temperature.
$A^3IS$ Placebo Formulation

| Ingredient | Percentage by weight |
|---|---|
| Purified water | 15.5% |
| Fructose Powder | 35% |
| Glucose Powder | 38% |
| Maltose Powder | 10% |
| Sucrose Powder | 1.5% |
| TOTAL | 100% |

TurChub® Test Systems (Medpharm)
90 mm and 245 mm sterile Petri dishes (Fisher Scientific, UK)
Human nail (Anonymous donation with informed consent)
Ringer's tablets (Oxoid Ltd., UK)
Sabouraud dextrose agar (Oxoid Ltd., UK)
Sterile gauze, 7.5 cm×7.5 cm
8 ply gauze swab
BP Type13 (Smith+Nephew, Propax, UK)
Sterile swabs (Fisher Scientific, UK)
*T. rubrum* (Clinical isolate)
Water, purified (Milli-Q gradient, Millipore, UK)
Method—TurChub® Zone of Inhibition Experiments Measurements were conducted using TurChub® agar based, distal finger nail model. The TurChub® test system utilises modified Franz cells. In use, the test compositions/formulations are applied to the top receiver well and the composition/formulation must first pass through full thickness human nail plates to show a zone-of inhibition (ZOI) in the receiver well (SDA infected with *T. rubrum*). Turchub cells are designed to test whether formulations pass through human nails prior to contact with the test organism. The TurChub® test system in this example was set up using *T. rubrum* as the test fungus for an infected nail.

*Trichophyton rubrum*—A sabouraud dextrose agar (SDA) slope inoculated with a *T. rubrum* culture which was originally isolated from an onychomycotic patient. The organism was sub-cultured onto fresh SDA slopes at 25° C. for 7 days and reference samples were placed into a glycerol solution and cryogenically frozen. The organism was subcultured on a three monthly basis to maintain viability and has been observed to be a virulent strain. The cultures are stored at 25° C. for seven days after sub-culturing, and then stored 2-8° C. until required.

Preparation of TurChub® Cells

A$^3$IS Active and Placebo were tested for their efficacy vs. *Trichophyton rubrum* after permeation through 5 μm thickness and full thickness distal human nail with and without water using a zone of inhibition measurement in the TurChub® cell test system as previously described in TurChub® test systems.

Step 1: Test Item Efficacy Testing
1. A nail was washed prior to use with 70% ethanol: deionised water, and then rinsed with sterile water.
2. Once the nail was mounted in the TurChub® cells, 50 μl of deionised water was added to cover the nail.
3. Following the addition of water, 0.5 ml of A$^3$IS was added to reservoir of TurChub® cell on top of the 50 μl of water.
4. The cells were incubated for 48 h.
5. The surface of the nails was washed with water and A$^3$IS reapplied as per steps 2 and 3 above.
6. The cells were incubated for a further 48 h.
7. Steps 5 and 6 were repeated.
8. Steps 5 and 6 were repeated.
9. Incubation took place for 24 hrs.
   The same process was repeated as follows:
   wherein no water was added to the surface of the nail.
   all the steps above were repeated for the placebo.
   Negative control—washed nail no test material.

Results and Conclusion

FIG. 22 shows a comparison of the diameter (cm) of the ZOI using a standard disc diffusion assay of A$^3$IS active and placebo with the organism *T. rubrum*, (245 mm square assay plate) (n=2).

The results of the experiment above indicate A$^3$IS active showed significant activity against *T. rubrum* on SDA suggesting compatibility of the drug with the media. No activity was seen with the A$^3$IS placebo. The results of the zone of inhibition assay can be regarded as confirmation of activity of A$^3$IS active against the test organism *T. rubrum* when incubated on standard Sabouraud Dextrose Agar and also confirmation that there was no placebo effect upon application of A$^3$IS placebo.

FIG. 23 shows a comparison of the average length of ZOI using the TurChub® test cell system with the organism *T. rubrum*, after applying 0.5 ml of the A$^3$IS formulations to 5 μm thickness and full thickness (distal) human nail, (n=3). The hatched zone indicates that the maximum zone of inhibition for the cell has been reached (e.g. total kill). Included are blank cells, whereby no formulations were added to the surface of the respective nail samples.

FIGS. 24 to 34 show that a maximum response was observed for A$^3$IS active formulation with and without water for both types of nail used. There was also no established difference in permeation of A$^3$IS active formulation with and without the application of water.

FIG. 25 shows 0.5 mL application of the formulation A$^3$IS active at (T=0, 48 and 96 h) applied to the TurChub® test system with full thickness distal human nail with the organism *T. rubrum*. As can be seen from the image there is a complete zone of inhibition indicating that the formulation penetrates a full thickness human nail.

FIG. 26 shows 0.5 mL application of the formulation A$^3$IS active+water at (T=0, 48 and 96 h) applied to the TurChub® test system with full thickness distal human nail with the organism *T. rubrum*. As can be seen from the image there is a complete zone of inhibition indicating that the hydrated formulation also penetrates a full thickness human nail.

FIG. 27 shows 0.5 mL application of the formulation A$^3$IS placebo at (T=0, 48 and 96 h) applied to the TurChub® test system with full thickness distal human nail with the organism *T. rubrum*. As can be seen from the image there is no zone of inhibition indicating that the placebo formulation is inactive as expected.

FIG. 28 shows 0.5 mL application of the formulation A$^3$IS placebo+water at (T=0, 48 and 96 h) applied to the TurChub® test system with full thickness distal human nail with the organism *T. rubrum*. As can be seen from the image there is no zone of inhibition indicating that the hydrated placebo formulation is inactive as expected.

FIG. 29 shows 0.5 mL application of the formulation A$^3$IS active at (T=0, 48 and 96 h) applied to the TurChub® test system with 5 μM human nail with the organism *T. rubrum*. As can be seen from the image there is a complete zone of inhibition indicating that the formulation penetrates a 5 μM human nail.

FIG. 30 shows 0.5 mL application of the formulation A$^3$IS active+water at (T=0, 48 and 96 h) applied to the TurChub® test system with 5 μM human nail with the organism *T. rubrum*. As can be seen from the image there is a complete zone of inhibition indicating that the hydrated formulation penetrates a 5 μM human nail.

FIG. 31 shows 0.5 mL application of the formulation A$^3$IS placebo at (T=0, 48 and 96 h) applied to the TurChub® test system with 5 μM human nail with the organism *T. rubrum*. As can be seen from the image there is no zone of inhibition indicating that the placebo formulation is inactive as expected.

FIG. 32 shows 0.5 mL application of the formulation A$^3$, S placebo+water at (T=0, 48 and 96 h) applied to the TurChub® test system with 5 μM human nail with the organism *T. rubrum*. As can be seen from the image there is no zone of inhibition indicating that the hydrated placebo formulation is inactive as expected.

FIG. 33 shows untreated control—TurChub® test system with full thickness distal human nail with the organism *T. rubrum*. As can be seen from the image there is no zone of inhibition as expected.

FIG. 34 shows untreated control—TurChub® test system with 5 μM human nail with the organism *T. rubrum*. As can be seen from the image there is no zone of inhibition as expected.

In conclusion, the TurChub® ZOI study was successfully carried out for A$^3$IS Active antifungal formulations. From the results for both 5 μm thickness and full thickness human nail, the formulations can be ranked as follows from highest to lowest efficacy:
1. A$^3$IS active=A$^3$IS active+water
2. A$^3$IS placebo=A$^3$IS placebo+water=untreated control In conclusion, the results clearly indicate that formulation A$^3$IS active showed a high efficacy against *T. rubrum* after permeation through 5 μm thickness and full thickness distal nail with and without water, as total kill of the organism was observed in the TurChub® nail model.

Example 22

Additional 2-Tier Storage-Stable Formulations

The following formulations were made in accordance with the protocol of Example 3 (in 50 g batches). Each formulation was tested for the immediate presence of hydrogen peroxide using the protocols previously described. The compositions of each of the formulations prepared are outlined in the tables below. Ideally, 0.5% glucose oxidase enzyme (ideally at least 5600 U/g) pre-dissolved in water.

Formulation No: 1

| Ingredient | % w/w |
|---|---|
| Water | 10 |
| Glucose | 79.5 |
| Fructose | 7.5 |
| Maltose | 2.2 |
| Sucrose | 0.3 |
| Glucose Oxidase | 0.5 |

Formulation No: 2

| Ingredient | % w/w |
|---|---|
| Water | 20 |
| Glucose | 69.5 |
| Fructose | 7.5 |
| Maltose | 2.2 |
| Sucrose | 0.3 |
| Glucose Oxidase | 0.5 |

Formulation No: 3

| Ingredient | % w/w |
|---|---|
| Water | 10 |
| Glucose | 20 |
| Fructose | 52 |
| Maltose | 15.4 |
| Sucrose | 2.1 |
| Glucose Oxidase | 0.5 |

Formulation No: 4

| Ingredient | % w/w |
|---|---|
| Water | 20 |
| Glucose | 10 |
| Fructose | 52 |
| Maltose | 15.4 |
| Sucrose | 2.1 |
| Glucose Oxidase | 0.5 |

Formulation No: 5

| Ingredient | % w/w |
|---|---|
| Water | 18 |
| Glucose | 30 |
| Fructose | 40 |
| Maltose | 10 |
| Sucrose | 1.5 |
| Glucose Oxidase | 0.5 |

Formulation No: 6

| Ingredient | % w/w |
|---|---|
| Water | 20 |
| Glucose | 40 |
| Fructose | 29.5 |
| Maltose | 10 |
| Sucrose | 0 |
| Glucose Oxidase | 0.5 |

Formulation No: 7

| Ingredient | % w/w |
|---|---|
| Water | 20 |
| Glucose | 40 |
| Fructose | 38 |
| Maltose | 0 |
| Sucrose | 1.5 |
| Glucose Oxidase | 0.5 |

Formulation No: 8

| Ingredient | % w/w |
|---|---|
| Water | 20 |
| Glucose | 30 |
| Fructose | 0 |
| Maltose | 48 |
| Sucrose | 1.5 |
| Glucose Oxidase | 0.5 |

Formulation No: 9

| Ingredient | % w/w |
|---|---|
| Water | 20 |
| Glucose | 40 |
| Fructose | 39.5 |
| Maltose | 0 |
| Sucrose | 0 |
| Glucose Oxidase | 0.5 |

Formulation No: 10

| Ingredient | % w/w |
|---|---|
| Water | 20 |
| Glucose | 60 |
| Fructose | 0 |
| Maltose | 19.5 |
| Sucrose | 0 |
| Glucose Oxidase | 0.5 |

Results

All batches were found to have both initial hydrogen peroxide content and antibacterial activity indicative of the sustained release of peroxide over a period of time.

H2O2 Generation mg\l:

| Formulation No. | Day 0 | Day 09 | Day 20 |
|---|---|---|---|
| 1 | ≥10 mg\l | ≥10 mg\l | ≥10 mg\l |
| 2 | ≥10 mg\l | ≥10 mg\l | ≥10 mg\l |
| 3 | ≥10 mg\l | ≥10 mg\l | ≥10 mg\l |
| 4 | ≥10 mg\l | ≥10 mg\l | ≥10 mg\l |

| Formulation No. | Day 0 | Day 09 | Day 20 |
| --- | --- | --- | --- |
| 5 | ≥10 mg\l | ≥10 mg\l | ≥10 mg\l |
| 6 | ≥10 mg\l | ≥10 mg\l | ≥10 mg\l |
| 7 | ≥10 mg\l | ≥10 mg\l | ≥10 mg\l |
| 8 | ≥10 mg\l | ≥10 mg\l | ≥10 mg\l |
| 9 | ≥10 mg\l | ≥10 mg\l | ≥10 mg\l |
| 10 | ≥10 mg\l | ≥10 mg\l | ≥10 mg\l |

The invention claimed is:

1. A storage-stable antimicrobial formulation for the treatment of fungal nail infections, comprising;
   glucose oxidase in an amount sufficient to provide an activity of at least 10 U per 100 g of the formulation;
   D-glucose from 20 to 85% by weight based on the weight of the total formulation;
   additional sugars selected from one or more of sucrose, fructose or maltose from 5 to 70% by weight based on the weight of the total formulation;
   water from 10 to 20% by weight based on the weight of the total formulation;
   with a pH from approximately 4 to 8;
   wherein the formulation provides a two-stage hydrogen peroxide release in which
   (a) storage-stable endogenously produced hydrogen peroxide is bioavailable within the formulation at a level of at least 10 mg per liter for immediate release; and
   (b) sustained release of further hydrogen peroxide for at least a twenty-four hour period occurs upon administration or application of the formulation.

2. A storage-stable antimicrobial formulation for the treatment of fungal nail infections as claimed in claim 1, wherein the formulation has antifungal and sporocidal effects which penetrate into and through the nail plate.

3. The formulation as claimed in claim 1 for the treatment of fungal nail infections caused by *Trichophyton rubrum* or *Aspergillus niger*.

4. The formulation as claimed in claim 1 in a form suitable for topical administration.

5. The formulation as claimed in claim 1 wherein the storage-stable endogenously produced hydrogen peroxide is bioavailable within the formulation at a level of at least 75 mg per liter for immediate release.

6. The formulation as claimed in claim 1 wherein the level of sustained release hydrogen peroxide produced upon administration or application of the formulation is at least 10 mg per liter.

7. The formulation as claimed in claim 1 further comprising a buffering agent.

8. The formulation of claim 7 wherein said buffering agent is selected from carbonic acid-bicarbonate, phosphoric acid and disodium hydrogen phosphate.

9. The formulation as claimed in claim 1 wherein the additional sugars are present from 10 to 70% by weight based on the weight of the total formulation.

10. The formulation as claimed in claim 1 wherein the additional sugars are a combination of sucrose, fructose and maltose.

11. The formulation as claimed in claim 1 wherein fructose is present from 8 to 50% w/w %, maltose is present from 4 to 15 w/w %, sucrose is present from 0.5 to 3 w/w % and the D-glucose, is present from 10 to 85 w/w %.

12. The formulation as claimed in claim 1 further comprising at least one viscosity modifying ingredient.

13. The formulation as claimed in claim 1 in a form suitable for delivery as part of a tissue, bandage or dressing.

14. A composition for combined therapy for the treatment of fungal nail infections comprising (i) the formulation of claim 1 and (ii) an antimicrobial agent for the treatment of fungal nail infections.

15. The composition for combined therapy according to claim 14 wherein the antimicrobial agent is selected from one or more of Griseofulvin, Ketoconazole, Itraconazole, Terbinafine, Clotrimazole, Amorolfine or Ciclopirox.

16. The formulation of claim 1 wherein the level of sustained release hydrogen peroxide produced upon administration or application of the formulation is at least 20 mg per liter.

* * * * *